(12) United States Patent
Burshtein et al.

(10) Patent No.: US 10,583,177 B2
(45) Date of Patent: Mar. 10, 2020

(54) FORMULATIONS FOR ORAL ADMINISTRATION OF ACTIVE AGENTS

(71) Applicant: Entera Bio Ltd., Jerusalem (IL)

(72) Inventors: Gregory Burshtein, Modiin (IL); Ariel Rothner, Jerusalem (IL); Phillip M. Schwartz, Jerusalem (IL); Hillel Galitzer, Yad Binyamin (IL)

(73) Assignee: Entera Bio Ltd., Jerusalem (IL)

( * ) Notice: Subject to any disclaimer, the term of this patent is extended or adjusted under 35 U.S.C. 154(b) by 0 days.

(21) Appl. No.: 15/549,436

(22) PCT Filed: Feb. 9, 2016

(86) PCT No.: PCT/IL2016/050155
§ 371 (c)(1),
(2) Date: Aug. 8, 2017

(87) PCT Pub. No.: WO2016/128974
PCT Pub. Date: Aug. 18, 2016

(65) Prior Publication Data
US 2018/0021272 A1  Jan. 25, 2018

Related U.S. Application Data

(60) Provisional application No. 62/113,629, filed on Feb. 9, 2015, provisional application No. 62/113,625, filed on Feb. 9, 2015, provisional application No. 62/113,638, filed on Feb. 9, 2015, provisional application No. 62/113,673, filed on Feb. 9, 2015, provisional application No. 62/113,604, filed on Feb. 9, 2015, provisional application No. 62/113,619, filed on Feb. 9, 2015, provisional application No. 62/113,600, filed on Feb. 9, 2015.

(51) Int. Cl.
| | |
|---|---|
| A61K 38/29 | (2006.01) |
| A61K 38/22 | (2006.01) |
| A61K 31/19 | (2006.01) |
| A61K 31/05 | (2006.01) |
| A61K 31/20 | (2006.01) |
| A61K 9/00 | (2006.01) |
| A61K 31/166 | (2006.01) |
| A61K 38/55 | (2006.01) |
| A61K 9/20 | (2006.01) |
| A61K 9/28 | (2006.01) |
| A61K 45/06 | (2006.01) |

(52) U.S. Cl.
CPC ............ *A61K 38/29* (2013.01); *A61K 9/0053* (2013.01); *A61K 9/20* (2013.01); *A61K 9/2009* (2013.01); *A61K 9/2013* (2013.01); *A61K 9/2086* (2013.01); *A61K 9/28* (2013.01); *A61K 9/2886* (2013.01); *A61K 31/05* (2013.01); *A61K 31/166* (2013.01); *A61K 31/19* (2013.01); *A61K 31/20* (2013.01); *A61K 38/22* (2013.01); *A61K 38/55* (2013.01); *A61K 45/06* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 5,360,793 A | * | 11/1994 | Brooks ................ A61K 9/0065 424/689 |
| 6,531,152 B1 | | 3/2003 | Lerner et al. |
| 6,632,451 B2 | | 10/2003 | Penhasi et al. |
| 8,110,547 B2 | | 2/2012 | Lee et al. |
| 8,673,352 B2 | | 3/2014 | Sowden |
| 9,186,412 B2 | | 11/2015 | Kidron et al. |
| 10,010,503 B2 | | 7/2018 | Kidron et al. |
| 2005/0054557 A1 | | 3/2005 | Goldberg |

(Continued)

FOREIGN PATENT DOCUMENTS

| | | |
|---|---|---|
| JP | 2005-281231 | 10/2005 |
| JP | 2006-111558 | 4/2006 |

(Continued)

OTHER PUBLICATIONS

International Search Report and the Written Opinion dated May 19, 2016 From the International Searching Authority Re. Application No. PCT/IL2016/050155.
International Search Report and the Written Opinion dated May 22, 2016 From the International Searching Authority Re. Application No. PCT/IL2016/050153.
International Search Report and the Written Opinion dated May 23, 2016 From the International Searching Authority Re. Application No. PCT/IL2016/050151.
International Search Report and the Written Opinion dated May 24, 2016 From the International Searching Authority Re. Application No. PCT/IL2016/050152.

(Continued)

*Primary Examiner* — Jeffrey T. Palenik

(57) ABSTRACT

A pharmaceutical composition for oral administration is disclosed herein, comprising a therapeutically active agent, SNAC and at least one antacid compound. Further disclosed herein is a pharmaceutical composition unit dosage form for oral administration of a therapeutically active agent is provided herein, the unit dosage form comprising: a core comprising the therapeutically active agent and SNAC (sodium 8-N-(2-hydroxybenzoyl)aminocaprylate); and an external layer comprising at least one protective agent selected from the group consisting of an antacid compound and a protease inhibitor. Methods and uses utilizing the aforementioned pharmaceutical compositions, as well as methods and uses utilizing co-administration, by oral administration, of at least one antacid composition, and a composition comprising the therapeutically active agent and SNAC, are further disclosed herein, for use in treating a condition treatable by oral administration of the therapeutically active agent.

23 Claims, 7 Drawing Sheets

(56) References Cited

U.S. PATENT DOCUMENTS

| | | | |
|---|---|---|---|
| 2006/0233881 A1 | 10/2006 | Sowden | |
| 2006/0234913 A1 | 10/2006 | Arbit et al. | |
| 2007/0087957 A1 | 4/2007 | Kidron | |
| 2007/0155664 A1 | 7/2007 | Ranklove et al. | |
| 2007/0178155 A1* | 8/2007 | Jiang | A61K 9/0065 424/466 |
| 2010/0285098 A1* | 11/2010 | Haley | A61K 9/0056 424/435 |
| 2010/0303901 A1 | 12/2010 | Shimoni et al. | |
| 2011/0142800 A1 | 6/2011 | Kidron et al. | |
| 2011/0250238 A1 | 10/2011 | Sangalli et al. | |
| 2013/0224300 A1 | 8/2013 | Maggio | |
| 2018/0028622 A1 | 2/2018 | Burshtein et al. | |
| 2018/0036234 A1 | 2/2018 | Burshtein et al. | |
| 2018/0036382 A1 | 2/2018 | Burshtein et al. | |
| 2018/0050096 A1 | 2/2018 | Burshtein et al. | |
| 2019/0209657 A1 | 7/2019 | Burshtein et al. | |

FOREIGN PATENT DOCUMENTS

| | | |
|---|---|---|
| WO | WO 00/48589 | 8/2000 |
| WO | WO 00/50386 | 8/2000 |
| WO | WO 00/59863 | 10/2000 |
| WO | WO 01/32130 | 5/2001 |
| WO | WO 01/32596 | 5/2001 |
| WO | WO 03/015822 | 2/2003 |
| WO | WO 03/045306 | 6/2003 |
| WO | WO 03/045331 | 6/2003 |
| WO | WO 2005/002549 | 1/2005 |
| WO | WO 2006/076692 | 7/2006 |
| WO | WO 2006/084164 | 8/2006 |
| WO | WO 2007/121471 | 10/2007 |
| WO | WO 2009/080764 | 7/2009 |
| WO | WO 2010/020978 | 2/2010 |
| WO | WO 2012/080471 | 6/2012 |
| WO | WO 2013/067309 | 5/2013 |
| WO | WO 2013/189988 | 12/2013 |
| WO | WO 2016/128970 | 8/2016 |
| WO | WO 2016/128971 | 8/2016 |
| WO | WO 2016/128972 | 8/2016 |
| WO | WO 2016/128973 | 8/2016 |
| WO | WO 2016/128974 | 8/2016 |
| WO | WO 2018/033927 | 2/2018 |

OTHER PUBLICATIONS

International Search Report and the Written Opinion dated May 24, 2016 From the International Searching Authority Re. Application No. PCT/IL2016/050154.
Aggarwal et al. "Parathyroid Hormone and Its Effects on Dental Tissues", Oral Diseases, 18(1): 48-54, Published Online Sep. 6, 2011.
Aspenberg "Parathyroid Hormone and Fracture Healing", Acta Orthopaedica, 84(1): 4-6, 2013.
Bashutski et al. "Teriparatide and Osseous Regeneration in the Oral Cavity", The New England Journal of Medicine, 363(25): 2397-2405, Dec. 16, 2010.
Bilezikian et al. "Hypoparathyroidism in the Adult: Epidemiology, Diagnosis, Pathophysiology, Target Organ Involvement, Treatment, and Challenges for Future Research", Journal of Bone and Mineral Research, 26(10): 2317-2337, Oct. 2011.
De Vos "finical Pharmacokinetics of Slow Release Mesalazine", Clinical Pharmacokinetics, 39(2): 85-97, Aug. 2000.
Gafni et al. "Daily Parathyroid Hormone 1-34 Replacement Therapy for Hypoparathyroidism Induces Changes in Bone Turnover and Structure", Journal of Bone and Mineral Research, 27(8): 1811-1820, Aug. 2012.
Giannotti et al. "Current Medical Treatment Strategies Concerning Fracture Healing", Clinical Cases in Mineral and Bone Metabolism, 10(2): 116-120, 2013.
Grover et al. "Teriparatide: A Novel Means to Ultimately Achieve True Regeneration!!!", Journal of Clinical and Diagnostic Research, 7(8): 1820-1823, Aug. 2013.
Maher et al. "Overcoming Poor Permeability: Translating Permeation Enhancers for Oral Peptide Delivery", Drug Discovery Today: Technologies, 9(1): e1131-e119, Aug. 31, 2012. p. e114, Right col., Para 2-3.
Malhotra et al. "Tensile Type of Stress Fracture Neck of Femur: Role of Teriparatide in the Process of Healing in a High Risk Patient for Impaired Healing of Fracture", Clinical Cases in Mineral and Bone Metabolism, 10(3): 210-212, 2013.
Martin "Bone Biology and Anabolic Therapies for Bone: Current Status and Future Prospects", Journal of Bone Metabolism, 21(1): 8-20, Epub Feb. 28, 2014.
Mitani "Effective Treatment of a Steroid-Induced Femoral Neck Fracture Nonunion With a Once-Weekly Administration of Teriparatide in a Rheumatoid Patient: A Case Report", Archives of Osteoporosis, 8(1-2): 131, Epub Mar. 29, 2013.
Moon et al. "Parathyroid Hormone 1-34(Teriparatide) Treatment in Pelvic Insufficiency Fractures. A Report of Two Cases", Journal of Bone Metabolism, 19(2): 147-151, 2012.
Peichl et al. "Parathyroid Hormone 1-84 Accelerates Fracture-Healing in Pubic Bones of Elderly Osteoporotic Women", the Journal of Bone & Joint Surgery, 93(17): 1583-1587, Sep. 7, 2011.
Puig-Domingo et al. "Successful Treatment of Vitamin D Unresponsive Hypoparathyroidism With Multipulse Subcutaneous Infusion of Teriparatide", European Journal of Endocrinology, 159:653-657, 2008.
Qi et al. "Effect of Casein and Protamine on the Enzymatic Degradation and the Orally Hypoglycemic Action of Insulin", Acta Pharmaceutica Sinica, 39(10): 844-848, 2004. English Abstract.
Qi et al. "Gastrointestinal Absorption Enhancement of Insulin by Administration of Enteric Microspheres and SNAC to Rats", Journal of Microencapsulation, 21(1): 37-45, Feb. 2004.
Riek et al. "The Pharmacological Management of Osteoporosis", Missouri Medicine, 108(2): 118-123, Mar.-Apr. 2011.
Rubin et al. "Therapy of Hypoparathyroidism With Intact Parathyroid Hormone", Osteoporosis International, 21(11): 1927-1934, Nov. 2010.
Sani et al. "Oral Protein-Drug Delivery Systems Suitable for Systemic Circulation", International Journal of Modern Biology and Medicine, 5(1): 5-16, Published Feb. 28, 2014.
Setchell et al. "Pharmacokinetics of a Slow-Release Formulation of Soybean Isoflavones in Healthy Postmenopausal Women", Journal of Agricultural and Food Chemistry, 53(6): 1938-1944, Published on Web Feb. 18, 2005.
Shah et al. "Regulating Drug Release Behavior and Kinetics From Matrix Tablets Based on Fine Particle-Sized Ethyl Cellulose Ether Derivatives: An In Vitro and In Vivo Evaluation", The Scientific World Journal, 2012(Art.ID 842348): 1-8, Published Online Apr. 29, 2012.
Shailesh et al. "Preparation and In Vitro Evaluation of Ethylcellulose Coated Egg Albumin Microspheres of Diltiazem Hydrochloride", Journal of Young Pharmacists, JYP, 2(1): 27-34, Jan. 2010.
Sheyn et al. "PTH Promotes Allograft Integration in a Calvarial Bone Defect", Molecular Pharmaceutics, 10(12): 4462-4471, Dec. 2, 2013.
Werle et al. "Chitosan-Aprotinin Coated Liposomes for Oral Peptide Delivery: Development, Characterisation and In Vivo Evaluation", International Journal of Pharmaceutics, 370(1): 26-32, Mar. 31, 2009. Abstract.
Werle et al. "Oral Protein Delivery: A Patent Review of Academic and Industrial Approaches", Recent Patents on Drug Delivery & Formulation, 3(2): 94-104, Jun. 1, 2009. p. 99, Right col., 2nd Para—p. 100, Left col.
Winer et al. "Effects of Once Versus Twice-Daily Parathyroid Hormone 1-34 Therapy in Children With Hypoparathyroidism", Journal of Clinical Endocrinology and Metabolism, 93(9): 3389-3395, Published Online May 20, 2008.
Winer et al. "Long-Term Treatment of Hypoparathyroidism: A Randomized Controlled Study Comparing Parathyroid Hormone-(1-34) Versus Calcitriol and Calcium", The Journal of Clinical Endocrinology & Metabolism, 88(9): 4214-4220, 2003.
Winer et al. "Synthetic Human Parathyroid Hormone 1-34 Replacement Therapy: A Randomized Crossover Trial Comparing Pump Versus Injections in the Treatment of Chronic Hypoparathyroid-

(56) References Cited

OTHER PUBLICATIONS ism", Journal of Clinical Endocrinology and Metabolism, 97(2): 391-399, Published Online Nov. 16, 2011.
International Preliminary Report on Patentability dated Aug. 24, 2017 From the International Bureau of WIPO Re. Application No. PCT/2016/050153. (8 Pages).
International Preliminary Report on Patentability dated Aug. 24, 2017 From the International Bureau of WIPO Re. Application No. PCT/2016/050154. (9 Pages).
Restriction Official Action dated Apr. 6, 2018 From U.S. Appl. No. 15/549,418. (5 pages).
Restriction Official Action dated Apr. 9, 2018 From U.S. Appl. No. 15/549,394. (7 pages).
Berkowitz et al. "Oral Heparin Administration with a Novel Drug Delivery Agent (SNAC) in Healthy Volunteers and Patients Undergoing Elective Total Hip Arthroplasty", Journal of Thrombosis and Haemostasis, 1: 1914-1919, Mar. 5, 2003.
International Search Report and the Written Opinion dated Nov. 28, 2017 From the International Searching Authority Re. Application No. PCT/IL2017/050920.
Bonlokke et al. p. 1, Line 4, p. 9, Line 26, p. 18, Line 16, p. 32, Line 9, p. 40, Line 21, p. 46, Line 6, Claims 16, 19, Expls.9, 11.
Engel et al. "An Innovative Smart Oral Delivery Technology for Proteins and Peptides", ONdrug Delivery, 69: 8-11, Jul. 25, 2016. p. 9, Left and Mid cols., p. 10, Left col., Third Para, Left and Mid cols., Fig.3.
Pharma Tips "Multiple Unit Tablets", Pharma Tips, Pharmaceutics, 5 P., Jan. 16, 2011.
Official Action dated Jan. 3, 2019 From the US Patent and Trademark Office Re. U.S. Appl. No. 15/549,425. (47 pages).
Brixen et al. "Teriparatide (Biosynthetic Human Parathyroid Hormone 1-34): A New Paradigm m the Treatment of Osteoporosis", Basic & clinical pharmacology & toxicology 94(6): 260-270, Jun. 2004.
Roche "The Complete Guide for Protease Inhibition", Roche Applied Science, 16 Pages, 2004.
Swihart et al. "Relating Body Size to the Rate of Home Range Use in Mammals", Ecology, 69(2): 393-399, Apr. 1988.
"The Amino Acid Sequence of Soybean Trypsin Inhibitor (Kunitz)", The Journal of Biochemistry, 71(1): 165-167. Jan. 25, 1972.
Official Action dated Feb. 8, 2019 From the US Patent and Trademark Office Re. U.S. Appl. No. 15/549,394. (34 pages).
Official Action dated Jan. 28, 2019 From the US Patent and Trademark Office Re. U.S. Appl. No. 15/549,418. (26 pages).
Bukata et al. "Orthopedic Uses of Teriparatide", Current Osteoporos Reports, 8(1): 28-33, Mar. 2010.
International Preliminary Report on Patentability dated Feb. 28, 2019 From the International Bureau of WIPO Re. Application No. PCT/IL2017/050920. (11 Pages).
Official Action dated Jan. 14, 2019 From the US Patent and Trademark Office Re. U.S. Appl. No. 15/549,442. (45 pages).
Cusano et al. "Use of Parathyroid Hormone in Hypoparathyroidism",Journal of Endocrinological Investigation, 36(11): 1121-1127, Dec. 2013.
Marine-Mammal "Blue Whale", retrieved from marinemammalcenter. org, 2 Pages, Jan. 10, 2018.
MGI "Mouse Facts", retrieved from informatics.jax.org, 2 Pages, Jan. 10, 2018.
Official Action dated Aug. 10, 2018 From the US Patent and Trademark Office Re. U.S. Appl. No. 15/549,394. (35 pages).
Official Action dated Sep. 21, 2018 From the US Patent and Trademark Office Re. U.S. Appl. No. 15/549,418. (36 Pages).
Supplementary European Search Report and the European Search Opinion dated Oct. 11, 2018 From the European Patent Office Re. Application No. 16748831.1. (9 Pages).
Supplementary European Search Report and the European Search Opinion dated Oct. 11, 2018 From the European Patent Office Re. Application No. 16748832.9. (9 Pages).
Supplementary European Search Report and the European Search Opinion dated Oct. 2018 From the European Patent Office Re. Application No. 16748833.7. (7 Pages).
Supplementary European Search Report and the European Search Opinion dated Oct. 18, 2018 From the European Patent Office Re. Application No. 16748834.5. (9 Pages).
Bastian et al. "Systemic Inflammation and Fracture Healing", Journal of Leukocyte Biology, 89(5): 669-673, May 2011.
Baumgarten et al. "Pressure Ulcers in Elderly Hip Fracture Patients Across the Continuum of Care", Journal of American Geriatrics Society, 57(5): 863-870, May 2009.
Della Rocca et al. "Parathyroid Hormone: Is There a Role in Fracture Healing?", Journal of Orthopaedic Trauma, 24(3): S31-S35, Mar. 2010, 5 pages.
Everyday "Teriparatide", The Everyday Health Web Page, Retrieved from everydayhealth.com, 5 Pages, Available Online 2010.— updated on Jun. 15, 2018.
Fallat et al. "Perfomring Surgery on Smokers: What You Should Know", Podiatry Today, 26(4): 30-38, Published Online Mar. 25, 2013.
Le Tourneau et al. "Dose Escalation Methods in Phase I Cancer Clinical Trials", JNCI: Journal of the National Cancer Institute, 101(10): 708-720, May 2009.
Spags "A Girl's Awkward Twerking on the Side of Road Distracted a Driver and Made for a Nasty Motorcycle Crash", Barstool Sports, Published Online on Apr. 17, 2017.
Suzman et al. "Bone-targeting Agents in Prostrate Cancer", Cancer and Metastasis Reviews, 33(0): 619-628, Sep. 2014.
Supplementary Partial European Search Report and the European Search Opinion dated Oct. 18, 2018 From the European Patent Office Re. Application No. 16748835.2. (12 Pages).
Abbas et al. "Clinical Pharmokokinetic and Pharmacodynamic Interaction Studies to Evaluate Effects of Antacid (Cimetidine and Maalox) Pretreatment on the Absorption of Heparin and its Delivery Agent, SNAC,Following Oral Administration in Healthy Subjects", Blood American Society of Hematology, XP009508315, 98(11/Pt. 2): 86b, # 3975, Nov. 16, 2001.
Applicant-Initiated Interview Summary dated Jul. 29, 2019 From the US Patent and Trademark Office Re. U.S. Appl. No. 15/549,442. (4 pages).
Supplementary European Search Report and the European Search Opinion dated Jul. 17, 2019 From the European Patent Office Re. Application No. 16748835.2. (14 Pages).
Official Action dated Jul. 12, 2019 From the US Patent and Tradmark Office Re. U.S. Appl. No. 15/549,425. (29 Pages).
Di Prospera "Understanding Oral Solid Dose Form (OSD) Manufacturing", Presentation at TechTank slides, 38 Pages, Mar. 18, 2014.
Sakai et al. "Species Differences in the Pharmacokinetic Parameters of Cytochrome P450 Probe Substrates between Experimental Animals, such as Mice, Rats, Dogs, Monkeys, and Microminipigs, and Humans", Journal of Drug Metabolism and Toxicology, 5(6): 1-12, 2014.
Official Action dated Jun. 28, 2019 From the US Patent and Trademark Office Re. U.S. Appl. No. 15/549,442. (28 Pages).
Notification of Office Action and Search Report dated Nov. 18, 2019 From the National Intellectual Property Administration of the People's Republic of China Re. Application No. 201680016126.5 and Its Translation Into English, (15 Pages).
Office Action dated Dec. 22, 2019 From the Israel Patent Office Re. Application No. 253802 and Its Translation Into English. (7 Pages).
Office Action dated Dec. 23, 2019 From the Israel Patent Office Re. Application No. 253804 and Its Translation Into English. (9 Pages).
Office Action dated Dec. 24, 2019 From the Israel Patent Office Re. Application No. 253803 and Its Translation Into English. (6 Pages).
Official Action dated Dec. 20, 2019 From the US Patent and Trademark Office Re. Application No. 15/549,418. (33 pages).
Cafesso "Intramuscular Injection", Retrieved from healthline.com, 3 Pages, 2013.
Drugs.com "Drug Dosage", Retrieved from drugs.com, 2 Pages, 2010.

* cited by examiner

FORMULATIONS FOR ORAL ADMINISTRATION OF ACTIVE AGENTS

RELATED APPLICATIONS

This application is a National Phase of PCT Patent Application No. PCT/IL2016/050155 having International filing date of Feb. 9, 2016, which claims the benefit of priority under 35 USC § 119(e) of U.S. Provisional Patent Application Nos. 62/113,600, 62/113,629, 62/113,604, 62/113,673, 62/113,638, 62/113,625 and 62/113,619, all filed on Feb. 9, 2015. The contents of the above applications are all incorporated by reference as if fully set forth herein in their entirety.

FIELD AND BACKGROUND OF THE INVENTION

The present invention, in some embodiments thereof, relates to drug delivery, and more particularly, but not exclusively, to formulations and/or systems for oral administration of therapeutically active agents such as, for example, therapeutically active polypeptides (e.g., proteins).

Oral administration of peptide pharmaceuticals is problematic due to degradation of peptides and/or proteins in the digestive system and poor absorption of large molecules.

U.S. Patent Application Publication No. 2007/0087957 describes compositions for oral administration of a protein, the compositions comprising a protein and an omega-3 fatty acid, as well as the use of such compositions for oral administration of insulin.

Qi & Ping [*J Microencapsulation* 2004, 21:37-45] describe administration of enteric microspheres containing insulin with SNAC (sodium 8-N-(2-hydroxybenzoyl)aminocaprylate). The enteric microspheres are for protecting the insulin from digestive enzymes of the stomach and small intestine, and the SNAC is for enhancing absorption.

U.S. Patent Application Publication No. 2011/0142800 describes compositions for oral administration of a protein, comprising a protein having a molecular weight of up to 100,000 Da, a protease inhibitor, and an absorption enhancer, such as SNAC, N-(10-[2-hydroxybenzoyl]amino)decanoic acid (SNAD), 8-[N-(2-hydroxy-4-methoxybenzoyl)amino]caprylic acid (4-MOAC), 8-[N-(2-hydroxy-5-chlorobenzoyl)amino]caprylic acid (5-CNAC) and 4-[(4-chloro-2-hydroxy-benzoyl)amino]butanoic acid (4-CNAB) and sodium salts thereof.

International Patent Application Publication WO 00/48589 describes solid oral dosage forms comprising a heparin drug in admixture with SNAC or SNAD for facilitating absorption and/or enhancing bioavailability of the heparin drug, wherein the heparin drug is reported to protect the SNAC or SNAD from precipitation during transit through acidic regions of the gastrointestinal tract.

U.S. Pat. No. 8,110,547 describes compositions for buccal administration of parathyroid hormone (PTH). The composition comprises PTH or a fragment or analog thereof, as well as a delivery agent such as 4-MOAC, SNAC, SNAD, 5-CNAC and 4-CNAB.

Parathyroid hormone (PTH) is secreted by the parathyroid gland as a polypeptide containing 84 amino acids. PTH has been reported to enhance bone growth when administered intermittently, with circulating levels returning to control levels within 3 hours [Martin, *J Bone Metab* 2014, 21:8-20]. In contrast, prolonged elevated PTH levels enhance release of calcium from bones (bone resorption).

Additional background art includes Qi et al. [*Acta Pharm Sinica* 2004, 39:844-848]; International Patent Application Publications WO 00/50386, WO 01/32130, WO 01/32596, WO 03/045306 and WO 2007/121471; Japanese Patent Application Nos. 2005281231 and 2006111558; and U.S. Patent Application Publication Nos. 2006/0234913 and 2013/0224300.

SUMMARY OF THE INVENTION

According to an aspect of some embodiments of the invention, there is provided a pharmaceutical composition unit dosage form for oral administration of a therapeutically active agent, the unit dosage form comprising:

a core comprising the therapeutically active agent and SNAC (sodium 8-N-(2-hydroxybenzoyl)aminocaprylate); and an external layer comprising at least one protective agent selected from the group consisting of an antacid compound and a protease inhibitor.

According to an aspect of some embodiments of the invention, there is provided a use of a unit dosage form described herein in the preparation of a medicament for use in the treatment of a condition treatable by oral administration of the therapeutically active agent in a subject in need thereof.

According to an aspect of some embodiments of the invention, there is provided a method of treating a condition treatable by oral administration of a therapeutically active agent in a subject in need thereof, the method comprising orally administering to the subject a unit dosage form described herein to a subject in need thereof.

According to an aspect of some embodiments of the invention, there is provided a pharmaceutical composition for oral administration of a therapeutic active agent, the composition comprising a therapeutically active agent, SNAC (sodium 8-N-(2-hydroxybenzoyl)aminocaprylate), and at least one antacid compound.

According to an aspect of some embodiments of the invention, there is provided a use of a composition described herein in the preparation of a medicament for use in the treatment of a condition treatable by oral administration of the therapeutically active agent in a subject in need thereof.

According to an aspect of some embodiments of the invention, there is provided a method of treating a condition treatable by oral administration of a therapeutically active agent in a subject in need thereof, the method comprising orally administering to the subject a composition described herein to a subject in need thereof.

According to an aspect of some embodiments of the invention, there is provided a method of treating a condition treatable by oral administration of a therapeutically active agent in a subject in need thereof, the method comprising co-administering to the subject, by oral administration, an antacid composition comprising at least one antacid compound and/or at least one gastric acid secretion inhibitor, and a composition comprising the therapeutically active agent and SNAC (sodium 8-N-(2-hydroxybenzoyl)aminocaprylate).

According to an aspect of some embodiments of the invention, there is provided a composition comprising a therapeutically active agent and SNAC (sodium 8-N-(2-hydroxybenzoyl)aminocaprylate), for use in the treatment of a condition treatable by oral administration of the therapeutically active agent in a subject in need thereof, wherein the treatment comprises co-administering an antacid composition comprising at least one antacid compound and/or at least one gastric acid secretion inhibitor.

According to an aspect of some embodiments of the invention, there is provided a use of a composition comprising a therapeutically active agent and SNAC (sodium 8-N-(2-hydroxybenzoyl)aminocaprylate) in the preparation of a medicament for use in the treatment of a condition treatable by oral administration of the therapeutically active agent in a subject in need thereof, wherein the treatment comprises co-administering an antacid composition comprising at least one antacid compound and/or at least one gastric acid secretion inhibitor.

According to some embodiments of the invention, the external layer is devoid of the therapeutically active agent.

According to some embodiments of the invention, the external layer is devoid of SNAC.

According to some embodiments of the invention, the external layer comprises at least one protease inhibitor.

According to some embodiments of the invention, the unit dosage form is coated with an enteric coating.

According to some embodiments of the invention, the external layer comprises at least one antacid compound.

According to some embodiments of the invention, the core comprises at least one antacid compound.

According to some embodiments of the invention, the unit dosage form is in a form of a tablet comprising the core and the external layer.

According to some embodiments of the invention, at least 90 weight percents of the tablet consists of ingredients selected from the group consisting of the therapeutically active agent, SNAC, and the at least one protective agent.

According to some embodiments of the invention, the core and/or the external layer further comprises a pharmaceutically acceptable carrier.

According to some embodiments of the invention, the unit dosage form is formulated such that absorption of the therapeutically active agent following oral administration of the unit dosage form is characterized by a bioavailability of the therapeutically active agent which is at least 10% higher than a bioavailability of the therapeutically active agent following oral administration of the core without the external layer.

According to some embodiments of the invention, the composition further comprises at least one protease inhibitor.

According to some embodiments of the invention, the at least one antacid compound is selected from the group consisting of calcium carbonate, calcium gluconate, calcium citrate, sodium carbonate, sodium bicarbonate, sodium gluconate, sodium citrate, sodium hydroxide, potassium carbonate, potassium bicarbonate, potassium gluconate, potassium citrate, potassium hydroxide, magnesium carbonate, magnesium gluconate, magnesium citrate, magnesium hydroxide, magnesium oxide, aluminum carbonate, aluminum gluconate, aluminum citrate, and aluminum hydroxide.

According to some embodiments of the invention, at least 90 weight percents of the composition consists of ingredients selected from the group consisting of the therapeutically active agent, SNAC, and the at least one antacid compound.

According to some embodiments of the invention, the composition is formulated such that absorption of the therapeutically active agent following oral administration of the composition is characterized by a bioavailability of the therapeutically active agent which is at least 10% higher than a bioavailability of the therapeutically active agent following oral administration of a composition comprising the therapeutically active agent and the SNAC (sodium 8-N-(2-hydroxybenzoyl)aminocaprylate) without the at least one antacid compound.

According to some embodiments of the invention, the composition is in a form of a homogeneous mixture.

According to some embodiments of the invention, the composition is formulated as a unit dosage form.

According to some embodiments of the invention, the unit dosage form comprises at least 50 mg of SNAC.

According to some embodiments of the invention, the unit dosage form is a solid unit dosage form.

According to some embodiments of the invention, the composition is formulated as a tablet.

According to some embodiments of the invention, the unit dosage form is soluble in gastric fluid.

According to some embodiments of the invention, the unit dosage form dissolves in gastric fluid in no more than 60 minutes.

According to some embodiments of the invention, the unit dosage form is for use in the treatment of a condition treatable by oral administration of the therapeutically active agent in a subject in need thereof.

According to some embodiments of the invention, the composition is for use in the treatment of a condition treatable by oral administration of the therapeutically active agent in a subject in need thereof.

According to some embodiments of the invention, the co-administering comprises administering the antacid composition prior to or concomitantly with the composition comprising the therapeutically active agent and SNAC.

According to some embodiments of the invention, at least one of the antacid composition and the composition comprising the therapeutically active agent and SNAC further comprises at least one protease inhibitor.

According to some embodiments of the invention, the at least one antacid compound and/or at least one gastric acid secretion inhibitor is selected from the group consisting of calcium carbonate, calcium gluconate, calcium citrate, sodium carbonate, sodium bicarbonate, sodium gluconate, sodium citrate, sodium hydroxide, potassium carbonate, potassium bicarbonate, potassium gluconate, potassium citrate, potassium hydroxide, magnesium carbonate, magnesium gluconate, magnesium citrate, magnesium hydroxide, magnesium oxide, aluminum carbonate, aluminum gluconate, aluminum citrate, aluminum hydroxide, cimetidine, famotidine, nizatidine, ranitidine, omeprazole, lansoprazole, dexlansoprazole, esomeprazole, rabeprazole and ilaprazole.

According to some embodiments of the invention, the antacid composition and the composition comprising the therapeutically active agent and SNAC are each soluble in gastric fluid.

According to some embodiments of the invention, each of the aforementioned compositions dissolves in gastric fluid in no more than 60 minutes.

According to some embodiments of the invention, absorption of the therapeutically active agent following the co-administering is characterized by a bioavailability of the therapeutically active agent which is at least 10% higher than a bioavailability of the therapeutically active agent following oral administration of the composition comprising the therapeutically active agent and the SNAC (sodium 8-N-(2-hydroxybenzoyl)aminocaprylate) without co-administering the antacid composition.

According to some embodiments of the invention, the at least one protease inhibitor comprises at least one trypsin inhibitor.

According to some embodiments of the invention, the at least one trypsin inhibitor is selected from the group consisting of is lima bean trypsin inhibitor, aprotinin, soybean trypsin inhibitor and ovomucoid trypsin inhibitor.

According to some embodiments of the invention, the at least one trypsin inhibitor comprises soybean trypsin inhibitor.

According to some embodiments of the invention, the therapeutically active agent has a molecular weight in a range of 0.5 kDa to 100 kDa.

According to some embodiments of the invention, the therapeutically active agent is a polypeptide.

According to some embodiments of the invention, the polypeptide is selected from the group consisting of a parathyroid hormone, insulin, a glucagon, an interferon, a growth hormone, an erythropoietin, a calcitonin, an omentin, a motilin, a leptin, a peptide YY, a GLP-1, a GLP-2, a granulocyte colony stimulating factor (G-CSF), an antibody, an interleukin, an erythropoietin, a vasopressin, a vasoactive intestinal peptide, a pituitary adenylate cyclase-activating peptide (PACAP), a blood clotting factor, an endomorphin, a TNF inhibitor, disitertide, octreotide, davunetide, icatibant, glucocerebrosidase, a gonadotropin releasing hormone, acyline, and a GLP-1 agonist.

According to some embodiments of the invention, the polypeptide is selected from the group consisting of parathyroid hormone and a fragment thereof.

According to some embodiments of the invention, the polypeptide comprises teriparatide.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 8:
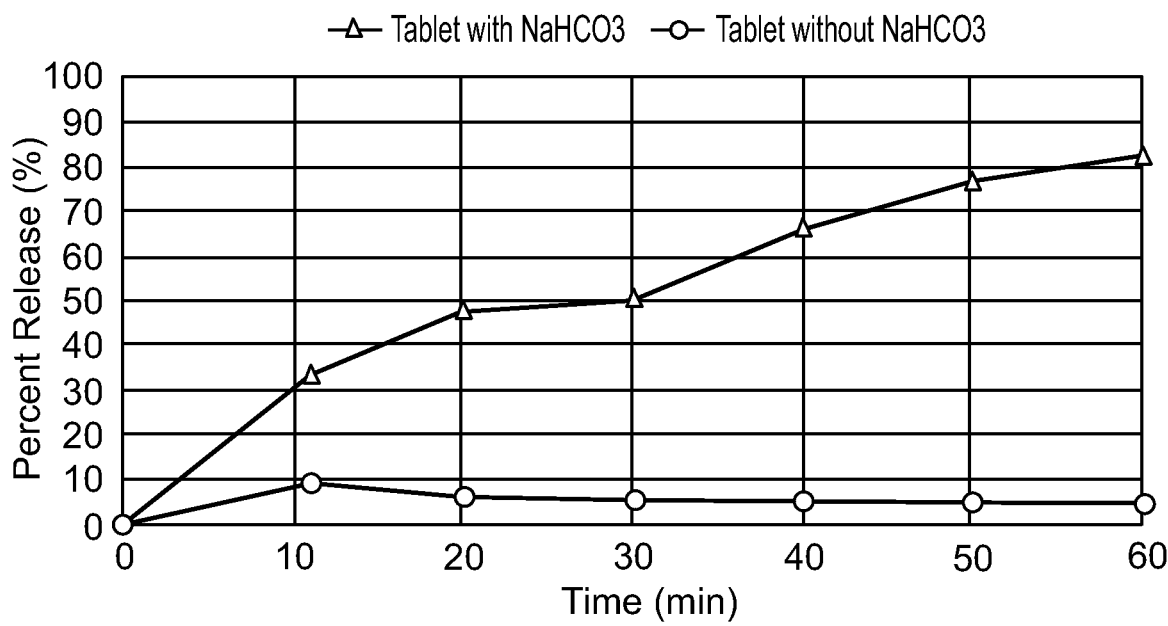
Figure 9:
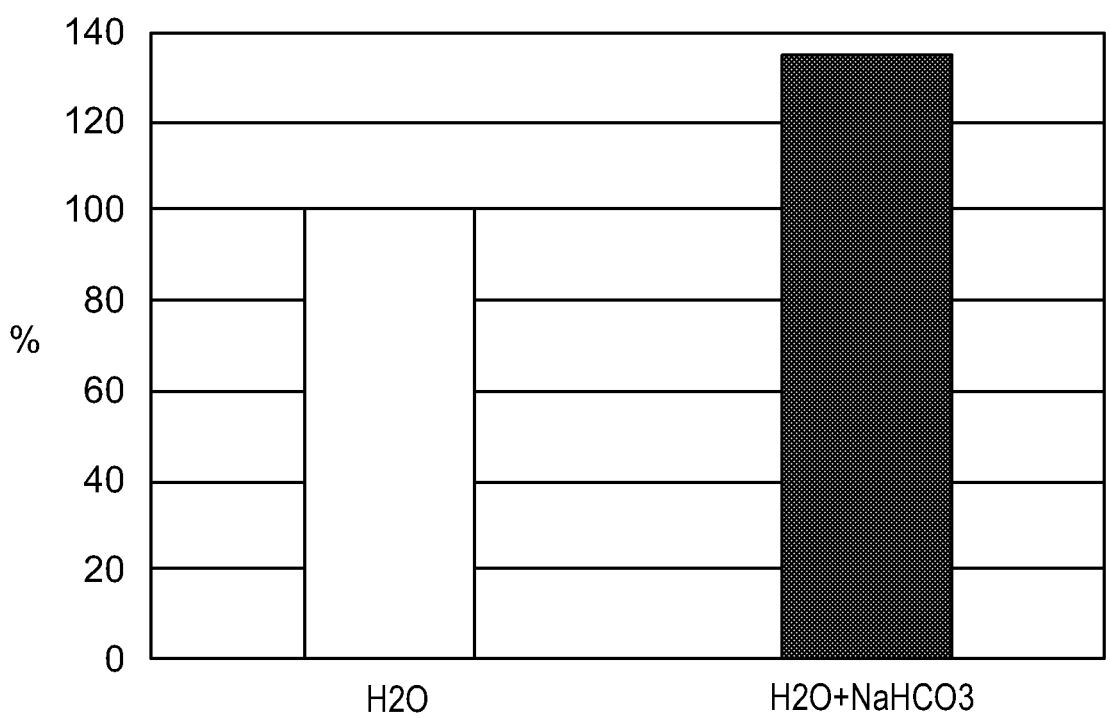

FIG. 8 presents a graph showing the release of SNAC, as a function of time, from an exemplary tablet formulation comprising sodium bicarbonate and from a control tablet formulation without sodium bicarbonate; and FIG. 9 presents a bar graph showing relative absorption of teriparatide from an exemplary oral formulation co-administered with 150 ml of water (H2O) or with an aqueous solution of 3 mg/ml sodium bicarbonate (H2O+NaCO3) (absorption upon co-administration with water defined as 100%).

DESCRIPTION OF SPECIFIC EMBODIMENTS OF THE INVENTION

The present invention, in some embodiments thereof, relates to drug delivery, and more particularly, but not exclusively, to formulations and/or systems for oral administration of therapeutically active agents such as, for example, therapeutically active polypeptides (e.g., proteins).

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While investigating the enhancement of absorption of therapeutically active agents by SNAC (sodium 8-N-(2-hydroxybenzoyl)aminocaprylate) upon oral administration, the present inventors have uncovered that such compositions are significantly affected by inactivation of the SNAC, an absorption enhancer, upon contact with stomach acid, which converts SNAC from a soluble carboxylate salt to an insoluble carboxylic acid. The inactivation of SNAC reduces the absorption of the therapeutically active agent, thereby reducing the efficacy of the composition. Furthermore, many therapeutically active agents are at least partially inactivated upon contact with stomach acid, which further reduces the efficacy of such compositions. In addition, protease inhibitors used to protect therapeutically active agents from proteolysis may also be at least partially inactivated upon contact with stomach acid, which may further reduce the efficacy of such compositions.

The inventors have further uncovered that the ability of protease inhibitors to protect therapeutically active agents against protease activity in the digestive system is limited, because much of the therapeutically active agent is inactivated by proteases before the proteases are inhibited by the protease inhibitor.

In order to overcome the abovementioned problems, the present inventors have designed compositions and unit dosage forms utilizing an agent for protecting the SNAC and/or the therapeutically active agent from stomach acid, thereby allowing increased absorption of the therapeutically active agent (e.g., via protection of the therapeutically active agent) and/or by absorption over a longer period of time (e.g., by protection of SNAC). Such a protective agent may be, for example, an antacid and/or an enteric coating.

The present inventors have further designed unit dosage forms so as to release a protective agent prior to release of the compound which the protective agent is intended to protect, for example, releasing an antacid for reducing acidity in a vicinity of an orally administered composition prior to exposure of SNAC and/or a therapeutically active agent to stomach acid, and/or releasing a protease inhibitor for inhibiting proteases prior to exposure of a therapeutically active agent to proteases.

According to one aspect of embodiments of the invention, there is provided a pharmaceutical composition unit dosage form for oral administration of a therapeutically active agent, the unit dosage form comprising a core and an external layer. The core comprises the therapeutically active agent and SNAC (sodium 8-N-(2-hydroxybenzoyl)aminocaprylate); and the external layer comprises at least one protective agent.

Herein, the term "protective agent" refers to an agent capable of protecting the therapeutically active agent and/or SNAC against enzymes and/or acid in the gastrointestinal tract. For example, a protease inhibitor can protect a therapeutically active agent from activity of a protease, and an antacid can protect SNAC (e.g., by reducing conversion of SNAC from a carboxylate salt to a carboxylic acid form) and/or a therapeutically active agent from stomach acid.

In some of any of the embodiments described herein, the protective agent is a protease inhibitor.

Herein throughout, the term "protease inhibitor" refers to a compound which reduces a proteolytic activity of a protease, for example, a proteolytic activity which inactivates a therapeutically active agent described herein. The term "protease inhibitor" encompasses, for example, both large molecules (e.g., proteins) and small molecules, as well as both naturally occurring compounds and synthetic compounds.

In some of any of the embodiments described herein, the protective agent is an antacid compound.

In some of any of the embodiments described herein, the unit dosage form comprises at least one protective agent which is an antacid compound and at least one protective agent which is a protease inhibitor.

Herein throughout, the term "antacid compound" refers to any pharmaceutically acceptable compound capable of neutralizing stomach acid (e.g., HCl in aqueous solution), preferably wherein one mole of antacid compound is capable of neutralizing at least 0.5 mole of HCl, and more preferably capable of neutralizing at least 1 mole of HCl. The therapeutically active agent, SNAC and protease inhibitors described herein are excluded from the scope of the phrase "antacid compound", even though they may exhibit some ability to neutralize stomach acid, in some embodiments of the invention.

Examples of antacid compounds which may be used in any one of the embodiments described herein relating to one or more antacid compounds (in accordance with any of the aspects of embodiments of the invention described herein), include, without limitation, calcium carbonate, calcium gluconate, calcium citrate, sodium carbonate, sodium bicarbonate, sodium gluconate, sodium citrate, sodium hydroxide, potassium carbonate, potassium bicarbonate, potassium gluconate, potassium citrate, potassium hydroxide, magnesium carbonate, magnesium gluconate, magnesium citrate, magnesium hydroxide, magnesium oxide, aluminum carbonate, aluminum gluconate, aluminum citrate, and aluminum hydroxide.

The unit dosage form may have any shape suitable for orally administered pharmaceutical dosage forms, including, without limitation, any 3-dimensional shape having a substantially rectangular (including substantially square), substantially circular and/or substantially oval cross-section along at least one axis. For example, the unit dosage form may have a substantially box-like shape, having a substantially rectangular cross-section (optionally with rounded corners) along 3 axes; a substantially cylindrical shape, having substantially circular and/or substantially oval cross-section along one axis, and a substantially rectangular cross-section (optionally with rounded corners) along 2 axes; or a substantially spherical or ovoid shape, having a substantially circular and/or substantially oval cross-section along 3 axes.

In some of any one of the embodiments described herein, the external layer comprises one or more protease inhibitors and one or more antacid compounds. In some such embodiments, the external layer consists essentially of one or more protease inhibitors and one or more antacid compounds. Alternatively, in some such embodiments, the external layer comprises a combination of one or more excipients with the protease inhibitor(s) and antacid compound(s).

In some of any one of the embodiments described herein, the external layer comprises one or more protease inhibitors, and is devoid of antacid compounds. In some such embodiments, the external layer consists essentially of one or more protease inhibitors. Alternatively, in some such embodiments, the external layer comprises a combination of one or more excipients with the protease inhibitor(s).

In some of any one of the embodiments described herein, the external layer comprises one or more antacid compounds, and is devoid of protease inhibitors. In some such embodiments, the external layer consists essentially of one or more antacid compounds. Alternatively, in some such embodiments, the external layer comprises a combination of one or more excipients with the antacid compound(s).

Herein throughout, the phrase "devoid of" encompasses the presence of minute amounts of the indicated substance (for example, less than 0.1 weight percent, optionally less than 0.05 weight percent, optionally less than 0.02 weight percent, and optionally less than 0.01 weight percent) as well as the complete absence of the indicated substance.

In some of any one of the embodiments described herein, a concentration (as a weight percentage) of therapeutically active agent in the external layer is lower than a concentration of the therapeutically active agent in the core. In some of any one of the embodiments described herein, a concentration (as a weight percentage) of therapeutically active agent in the external layer is less than 50% of a concentration of the therapeutically agent in the core. In some embodiments, the concentration in the external layer is less than 20% of the concentration in the core. In some embodiments, the concentration in the external layer is less than 10% of the concentration in the core. In some embodiments, the concentration in the external layer is less than 5% of the concentration in the core. In some embodiments, the concentration in the external layer is less than 2% of the concentration in the core. In some embodiments, the concentration in the external layer is less than 1% of the concentration in the core. In some embodiments, the external layer is devoid of the therapeutically active agent.

In some of any one of the embodiments described herein, a concentration (as a weight percentage) of SNAC in the external layer is lower than a concentration of SNAC in the core. In some of any one of the embodiments described herein, a concentration (as a weight percentage) of SNAC in the external layer is less than 50% of a concentration of SNAC in the core. In some embodiments, the concentration in the external layer is less than 20% of the concentration in the core. In some embodiments, the concentration in the external layer is less than 10% of the concentration in the core. In some embodiments, the concentration in the external layer is less than 5% of the concentration in the core. In some embodiments, the concentration in the external layer is less than 2% of the concentration in the core. In some embodiments, the concentration in the external layer is less than 1% of the concentration in the core. In some embodiments, the external layer is devoid of SNAC. In some embodiments, the external layer is devoid of the therapeutically active agent and devoid of SNAC.

In some of any one of the embodiments described herein, the external layer covers the whole surface of the core.

In some of any one of the embodiments described herein, the external layer does not cover the whole surface of the core. In some embodiments wherein the external layer does not cover the whole surface of the core, the external layer is separated into a plurality of unconnected layers (e.g., 2 layers, 3 layers, 4 layers, or more than 4 layers), each of the unconnected layers covering a different region of the surface of the core. In such embodiments, the phrase "external layer" refers collectively to all such unconnected layers. In some embodiments, the external layer is separated into two unconnected layers which cover opposite sides of the core. In alternative embodiments wherein the external layer does not cover the whole surface of the core, the external layer is in a form of a single continuous layer.

In some of any one of the embodiments described herein, the external layer covers at least 30% of the surface area of the core. In some embodiments, the external layer covers at least 40% of the surface area of the core. In some embodiments, the external layer covers at least 50% of the surface area of the core. In some embodiments, the external layer covers at least 60% of the surface area of the core. In some embodiments, the external layer covers at least 70% of the surface area of the core. In some embodiments, the external layer covers at least 80% of the surface area of the core. In some embodiments, the external layer covers at least 90% of the surface area of the core.

In some embodiments of any one of the embodiments described herein, the protease inhibitor(s) and/or antacid compound(s) in the external layer are distributed homogeneously throughout the external layer.

In some embodiments of any one of the embodiments described herein, the protease inhibitor(s) and/or antacid compound(s) in the external layer are distributed inhomogeneously throughout the external layer.

In some such embodiments, the protease inhibitor(s) and/or antacid compound(s) are within particles (e.g., microspheres containing the protease inhibitor(s) and/or antacid compound(s)), and the external layer further comprises a material (e.g., a filler and/or binder) between the particles.

Alternatively or additionally, in some embodiments, the external layer comprises two or more layers (e.g., concentric layers), wherein each layer within the external layer has a different composition. For example, the external layer may optionally comprise a first layer which comprises one of the protease inhibitor(s) and/or antacid compound(s), a second layer which comprises another of the protease inhibitor(s) and/or antacid compound(s), and optionally one or more additional layers, each comprising different inhibitor(s) and/or antacid compound(s).

In some embodiments of any one of the embodiments described herein, the core further comprises one or more protease inhibitors and/or antacid compounds, in addition to a therapeutically active agent and SNAC.

In some embodiments of any one of the embodiments described herein, the core consists essentially of the therapeutically active agent and SNAC or a combination of the therapeutically active agent, SNAC and the protease inhibitor(s) and/or antacid compound(s).

In some embodiments of any one of the embodiments described herein, the core comprises a combination of one or more excipients with the therapeutically active agent and SNAC (and optionally the protease inhibitor(s) and/or antacid compound(s)).

In some embodiments of any one of the embodiments described herein, the core comprises a therapeutically active agent, SNAC and one or more antacid compounds. In some embodiments, the core consists essentially of a combination of the therapeutically active agent, SNAC and the antacid compound(s). Alternatively, in some embodiments, the core comprises a combination of one or more excipients with the therapeutically active agent, SNAC and antacid compound(s).

In some embodiments of any one of the embodiments described herein, the core comprises a therapeutically active agent, SNAC and one or more protease inhibitors. In some embodiments, the core consists essentially of a combination of the therapeutically active agent, SNAC and the protease inhibitor(s). Alternatively, in some embodiments, the core comprises a combination of one or more excipients with the therapeutically active agent, SNAC and protease inhibitor(s).

In some embodiments of any one of the embodiments described herein, the therapeutically active agent and/or SNAC in the core are distributed homogeneously throughout the core.

In some embodiments of any one of the embodiments described herein, the therapeutically active agent and/or SNAC in the core are distributed inhomogeneously throughout the core.

In some such embodiments, the therapeutically active agent and/or SNAC are within particles (e.g., microspheres containing the therapeutically active agent and/or SNAC), and the core comprises a material (e.g., a filler and/or binder) between the particles.

Alternatively or additionally, in some embodiments, the core comprises an inner portion and an outer portion (e.g., configured concentrically), wherein each portion within the core has a different composition. For example, the core may optionally comprise an outer portion which comprises the therapeutically active agent and an inner portion which comprises SNAC, or vice versa.

In some of any one of the embodiments described herein, the unit dosage form further comprises a coating which coats the outer surface of the external layer described herein, and optionally also a region of a core surface which is not covered by an external layer (in embodiments wherein the external layer does not cover the whole core). In some embodiments, the coating is formed from material which dissolves in at least a portion of the gastrointestinal tract.

In some embodiments of any one of the embodiments described herein, the coating is an enteric coating, that is, a coating which dissolves under conditions in the intestines (e.g., in an aqueous environment having a pH of at least 5.5 and/or in the presence of colonic bacteria), thereby exposing the external layer, but does not dissolve under conditions in the stomach (e.g., in an aqueous environment having a pH in a range of from 1 to 3.5). An enteric coating may optionally dissolve in the duodenum, optionally in the jejunum, optionally in the ileum, and optionally in the colon. Many enteric coatings are known in the art, and the skilled person will be readily capable of selecting and preparing a suitable enteric coating for dissolving in a pre-determined region of the intestines.

In some embodiments of any one of the embodiments described herein, the coating dissolves under conditions in the stomach (e.g., in an aqueous environment, optionally only when a low pH is present), thereby exposing the external layer. Such a coating is optionally adapted for altering an appearance of the unit dosage form (e.g., for aesthetic enhancement and/or labeling), to provide flavor and/or mask flavor, and/or to protect the external layer and/or core (e.g., from mechanical insult, air, light and/or liquids).

Dissolution of the unit dosage form in the gastrointestinal system initially comprises primarily dissolution of the external layer (optionally after dissolution of a coating, if present), thereby releasing the protease inhibitor(s) and/or antacid compound(s) in the external layer prior to release of therapeutically active agent and SNAC from the core.

Figure 3:
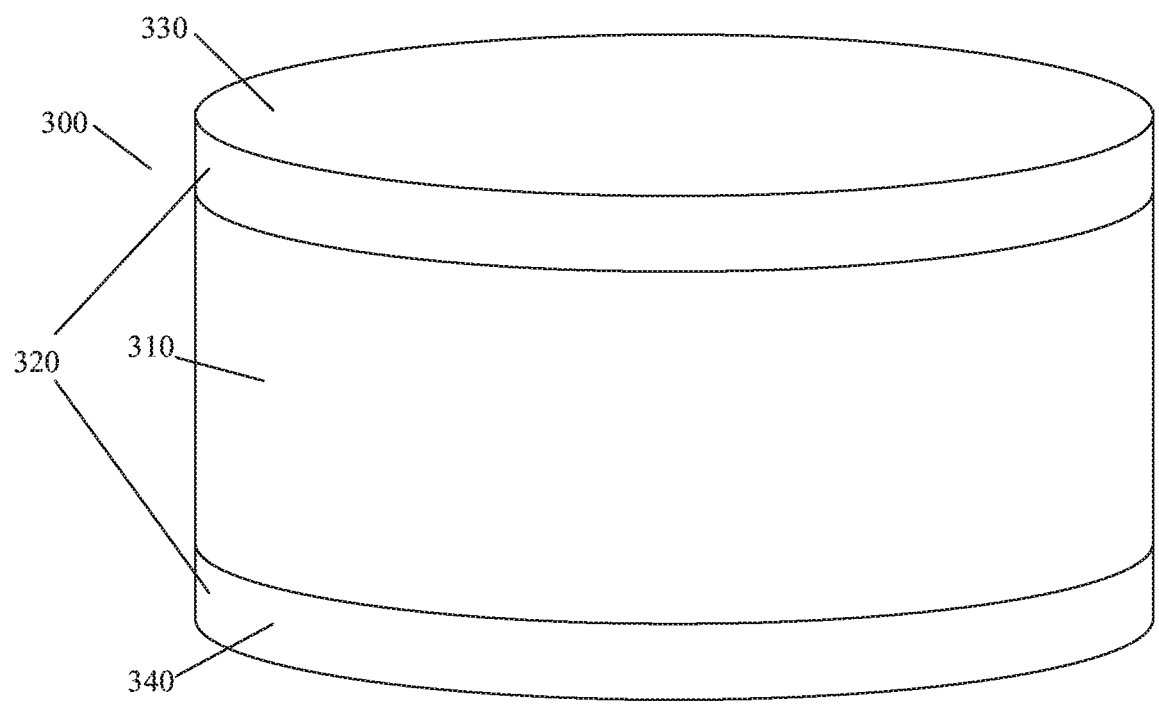
FIG. 3 depicts an exemplary tablet according to some embodiments of the invention.
Figure 4:
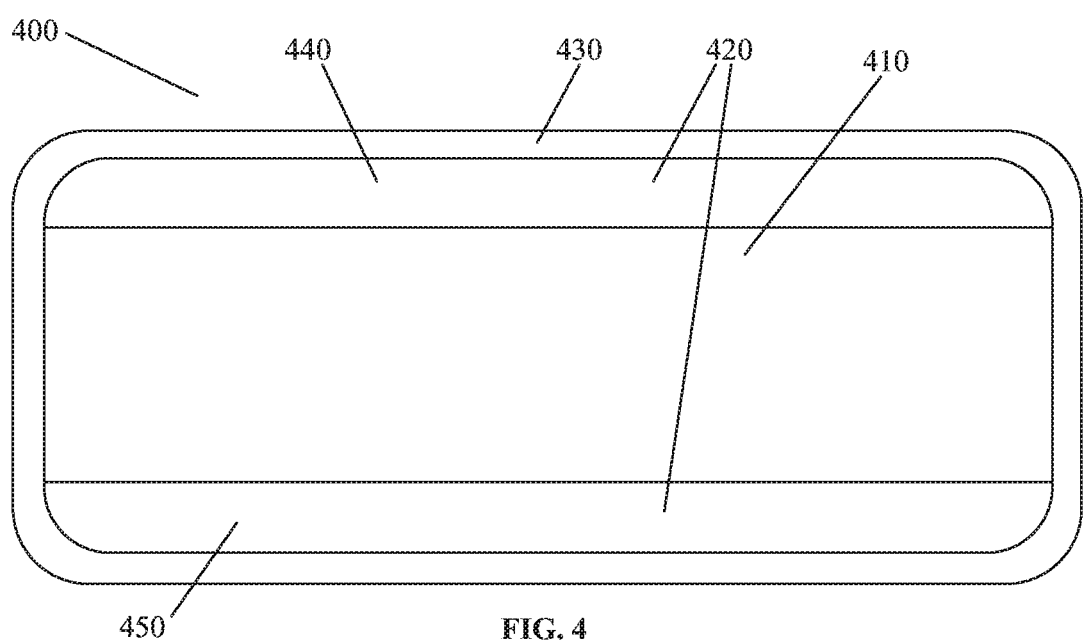
FIG. 4 depicts an exemplary coated tablet according to some embodiments of the invention.

In some embodiments of any one of the embodiments described herein, the unit dosage form is formulated as a tablet. In some embodiments, the unit dosage form is formulated as a multi-layered tablet (e.g., a 3-layered tablet), in which the external layer forms an upper layer and a lower layer, and the core is formulated as a middle layer sandwiched between the upper layer and a lower layer. Exemplary tablets are shown in FIGS. 3 and 4 herein. Any of the multi-layered tablets described herein may optionally prepared according to any technique known in the art for preparing multi-layered tablets (e.g., 3-layered tablet), including, without limitation a technique described by Shende et al. [*Int J Drug Delivery* 2012, 4:418-426], the contents of which are incorporated herein by reference.

In some embodiments of any one of the embodiments described herein, the unit dosage form consists primarily of the combination of therapeutically active agent, SNAC, and at least one protective agent (protease inhibitor(s) and/or antacid compound(s)) described herein, that is, at least 50 weight percents of the unit dosage form consists of ingredients selected from the group consisting of a therapeutically active agent, SNAC and at least one protective agent. In some embodiments, at least 60 weight percents of the unit dosage form consists of a therapeutically active agent, SNAC and at least one protective agent. In some embodiments, at least 70 weight percents of the unit dosage form consists of a therapeutically active agent, SNAC and at least one protective agent. In some embodiments, at least 80 weight percents of the unit dosage form consists of a therapeutically active agent, SNAC and at least one protective agent. In some embodiments, at least 90 weight percents of the unit dosage form consists of a therapeutically active agent, SNAC and at least one protective agent. In some embodiments, at least 95 weight percents of the unit dosage form consists of a therapeutically active agent, SNAC and at least one protective agent. In some embodiments, at least 98 weight percents of the unit dosage form consists of a therapeutically active agent, SNAC and at least one protective agent. In some embodiments, the unit dosage form is formulated as a tablet.

In some embodiments of any one of the embodiments described herein, the external layer and core described herein consist primarily of the combination of therapeutically active agent, SNAC, and at least one protective agent (protease inhibitor(s) and/or antacid compound(s)) described herein, that is, at least 50 weight percents of the total weight of the external layer and core consists of ingredients selected from the group consisting of a therapeutically active agent, SNAC and at least one protective agent. In some embodiments, at least 60 weight percents of the total weight of the external layer and core consists of a therapeutically active agent, SNAC and at least one protective agent. In some embodiments, at least 70 weight percents of the total weight of the external layer and core consists of a therapeutically active agent, SNAC and at least one protective agent. In some embodiments, at least 80 weight percents of the total weight of the external layer and core consists of a therapeutically active agent, SNAC and at least one protective agent. In some embodiments, at least 90 weight percents of the total weight of the external layer and core consists of a therapeutically active agent, SNAC and at least one protective agent. In some embodiments, at least 95 weight percents of the total weight of the external layer and core consists of a therapeutically active agent, SNAC and at least one protective agent. In some embodiments, at least 98 weight percents of the total weight of the external layer and core consists of a therapeutically active agent, SNAC and at least one protective agent. In some embodiments, the external layer and core are formulated as parts of a tablet. In some embodiments, the tablet is a multi-layered tablet (e.g., 3-layered tablet).

Figure 1A:
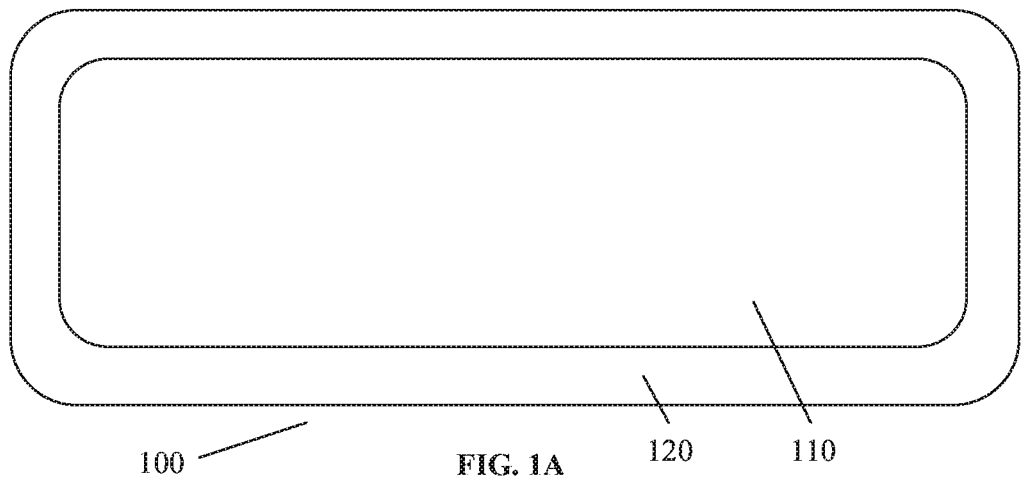
FIGS. 1A-1C depict exemplary unit dosage forms according to some embodiments of the invention.
Figure 1B:
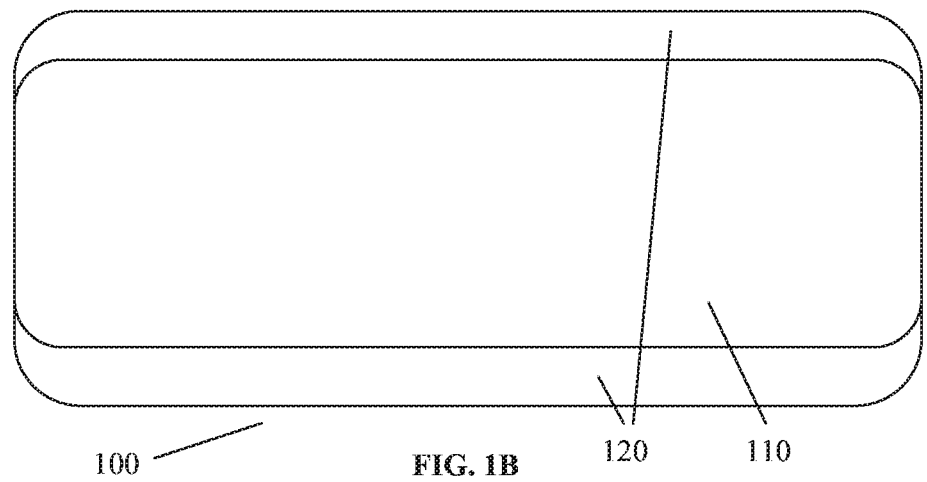
Figure 1C:
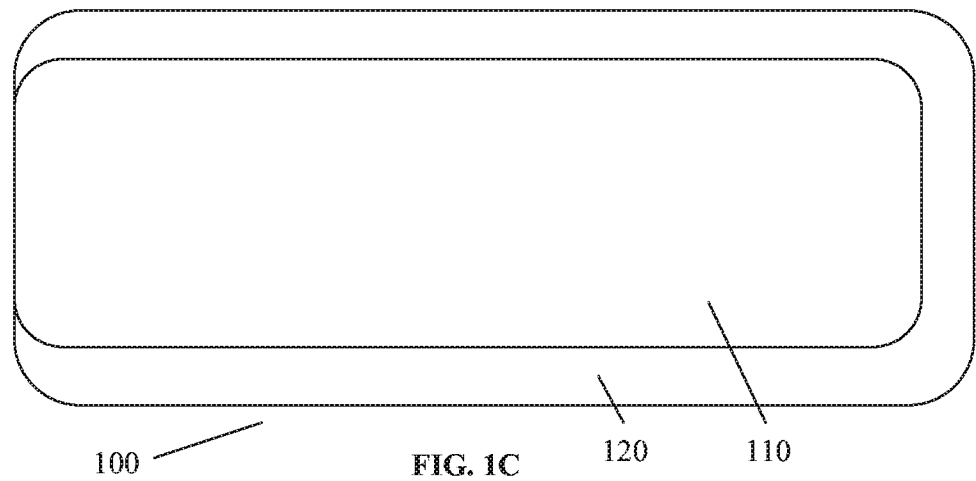

Referring now to the drawings, FIGS. 1A-1C show the structure, in cross-section, of an exemplary unit dosage form 100 according to some related embodiments of the invention. Unit dosage form 100 comprises a core 110 and an external layer 120. The embodiments shown in FIGS. 1A-1C differ only in that FIG. 1A shows exemplary embodiments in which external layer 120 covers all of core 110; FIG. 1B shows exemplary embodiments in which external layer 120 is separated into unconnected layers which cover different regions of core 110 (such that external layer 120 does not cover all of core 110); and FIG. 1C shows exemplary embodiments in which external layer 120 is a single continuous layer which does not cover all of core 110. Unit dosage form 100 is optionally substantially rectangular in cross-section (as depicted in FIGS. 1A-1C) along at least one axis. However, the cross-section may have a differently shape (e.g., substantially circular and/or substantially oval), and it is to be understood that the shapes depicted in FIGS. 1A-1C are not intended to be limiting.

External layer 120 comprises one or more protease inhibitors and/or antacid compounds, in accordance with any of one of the embodiments described herein relating to a composition of an external layer, and optionally consists essentially of one or more protease inhibitors and/or antacid compounds (e.g., in accordance with one of the respective embodiments described herein). Alternatively, external layer 120 comprises a combination of one or more excipients with the protease inhibitor(s) and/or antacid compound(s) (e.g., in accordance with one of the respective embodiments described herein).

In some embodiments, external layer 120 comprises one or more protease inhibitors (e.g., in accordance with one of the respective embodiments described herein), is optionally devoid of antacid compounds, and optionally consists essentially of one or more protease inhibitors (e.g., in accordance with one of the respective embodiments described herein). Alternatively, external layer 120 comprises a combination of one or more excipients with the protease inhibitor(s) (e.g., in accordance with one of the respective embodiments described herein).

In some embodiments, external layer 120 comprises one or more antacid compounds (e.g., in accordance with one of the respective embodiments described herein), is optionally devoid of protease inhibitors, and optionally consists essentially of one or more antacid compounds (e.g., in accordance with one of the respective embodiments described herein). Alternatively, external layer 120 comprises a combination of one or more excipients with the antacid compound(s) (e.g., in accordance with one of the respective embodiments described herein).

In some embodiments, a concentration (as a weight percentage) of therapeutically active agent in external layer 120 is less than a concentration of the therapeutically agent in core 110 (e.g., in accordance with one of the respective embodiments described herein). In some embodiments, external layer 120 is devoid of the therapeutically active agent.

In some embodiments, a concentration (as a weight percentage) of SNAC in external layer 120 is less than a concentration of SNAC in core 110 (e.g., in accordance with one of the respective embodiments described herein). In some embodiments, external layer 120 is devoid of SNAC. In some embodiments, external layer 120 is devoid of the therapeutically active agent and devoid of SNAC.

Figure 2A:
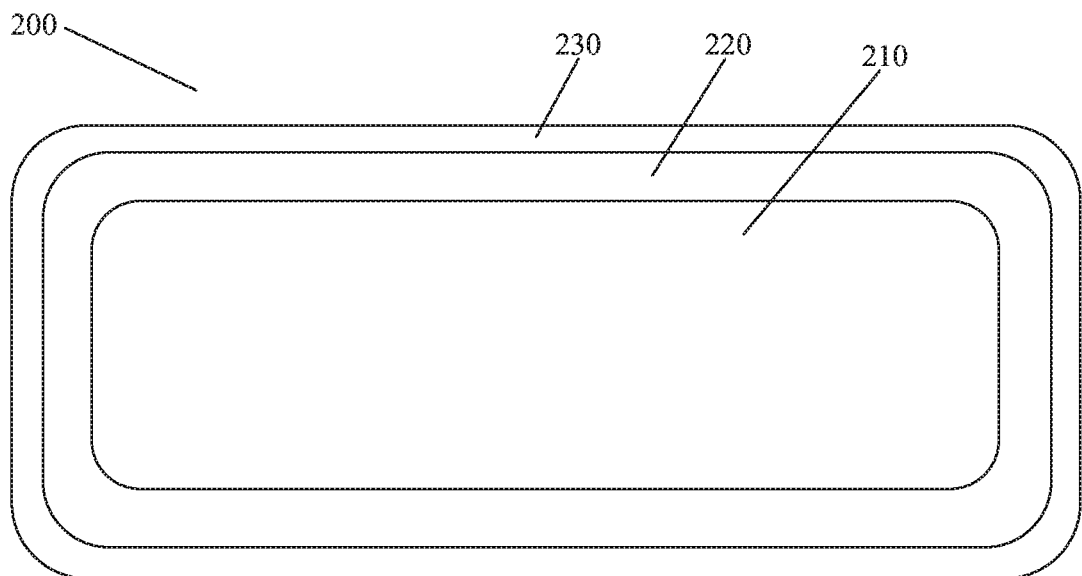
FIGS. 2A-2C depict exemplary coated unit dosage forms according to some embodiments of the invention.
Figure 2B:
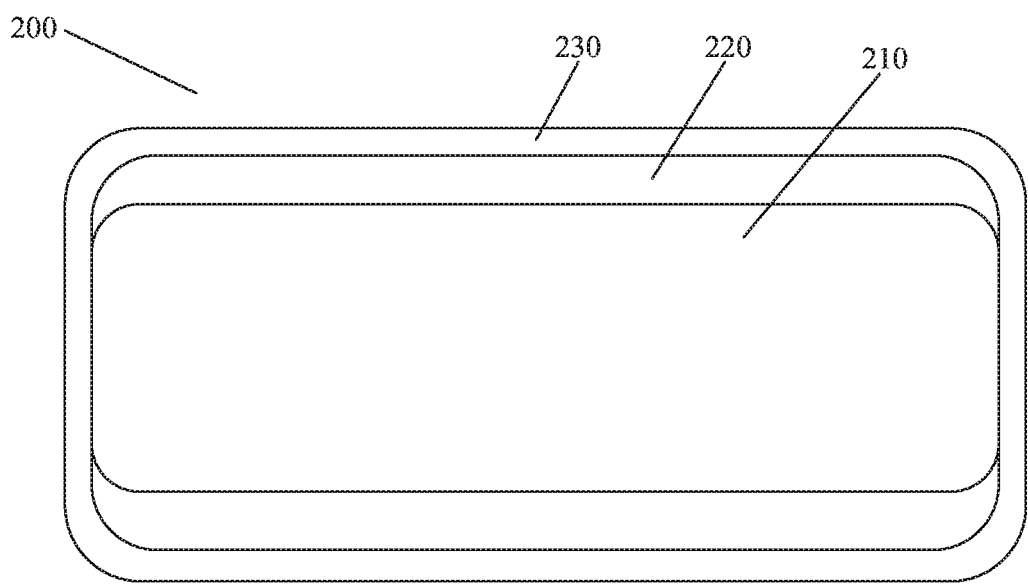
Figure 2C:
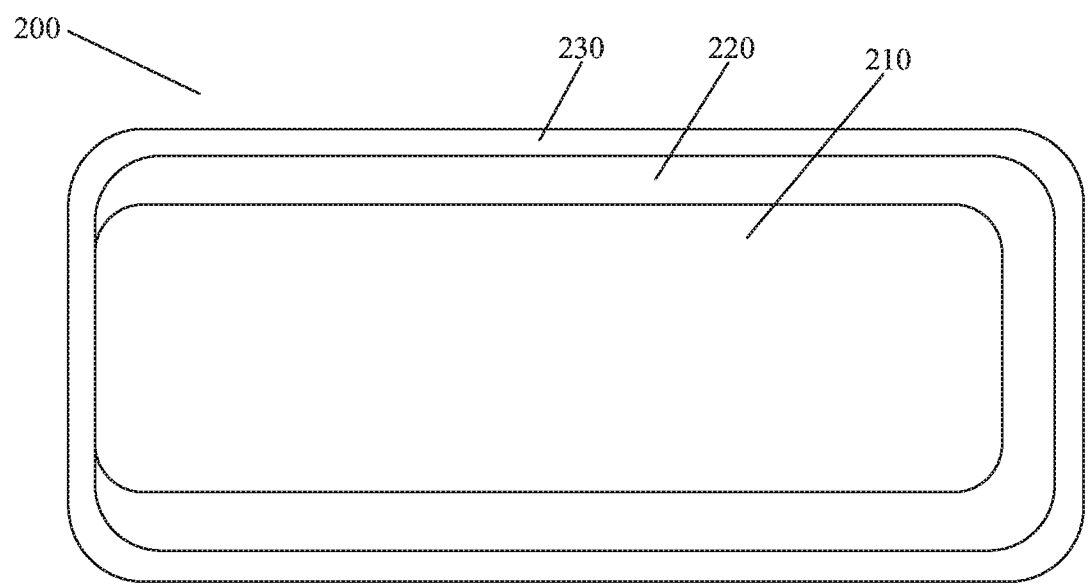

FIGS. 2A-2C show the structure, in cross-section, of an exemplary unit dosage form 200 according to some related embodiments of the invention. Unit dosage form 200 as shown in FIGS. 2A-2C, corresponds to unit dosage form 100 (in any one of the respective embodiments described herein) as shown, respectively, in FIGS. 1A-1C, differing from unit dosage form 100 in that unit dosage form 200 further comprises coating 230. Unit dosage form 200 comprises a core 210 and an external layer 220, which correspond, respectively, to core 110 and an external layer 120 of unit dosage form 100, as described herein, in any one of the respective embodiments.

The embodiments shown in FIGS. 2A-2C differ only in that FIG. 2A shows exemplary embodiments in which external layer 220 covers all of core 210; FIG. 2B shows exemplary embodiments in which external layer 220 is separated into unconnected layers which cover different regions of core 210 (such that external layer 220 does not cover all of core 210); and FIG. 2C shows exemplary embodiments in which external layer 220 is a single continuous layer which does not cover all of core 210.

Unit dosage form 200 is optionally substantially rectangular in cross-section (as depicted in FIGS. 2A-2C) along at least one axis. However, the cross-section may have a differently shape (e.g., substantially circular and/or substantially oval), and it is to be understood that the shapes depicted in FIGS. 2A-2C are not intended to be limiting.

Coating 230 has a composition in accordance with any one of the embodiments described herein relating to a coating, and is optionally formed from material which dissolves in at least a portion of the gastrointestinal tract (e.g., in accordance with one of the respective embodiments described herein).

In some embodiments of any one of the embodiments described herein, coating 230 is an enteric coating, as described herein (e.g., in accordance with one of the respective embodiments).

In some embodiments of any one of the embodiments described herein, coating 230 dissolves under conditions in the stomach (e.g., in accordance with one of the respective embodiments described herein), thereby exposing external layer 220. Coating 230 is optionally adapted for altering an appearance of unit dosage form 200 (e.g., for aesthetic enhancement and/or labeling), to provide flavor and/or mask flavor, and/or to protect external layer 220 and/or core 210 (e.g., from mechanical insult, air, light and/or liquids), e.g., in accordance with one of the respective embodiments described herein).

In some embodiments of any one of the embodiments described herein, coating 230 is an enteric coating (e.g., in accordance with one of the respective embodiments described herein), external layer 220 comprises one or more protease inhibitors (e.g., in accordance with one of the respective embodiments described herein), and core 210 comprises a therapeutically active agent and SNAC, and optionally one or more protease inhibitors (e.g., in accordance with one of the respective embodiments described herein). In some such embodiments, unit dosage form 200 is formulated as a tablet (e.g., optionally as depicted in FIG. 4).

In embodiments wherein coating 230 is an enteric coating, dissolution of the unit dosage form 200 in the gastrointestinal system comprises dissolution of enteric coating 230 in the intestines, followed primarily by dissolution of external layer 220, thereby releasing the protease inhibitor(s) in the external layer prior to release of therapeutically active agent and SNAC from core 210.

In some of any of the embodiments wherein coating 230 is an enteric coating, external layer 220 and/or core 210 is devoid of an antacid.

In some embodiments of any one of the embodiments described herein, coating 230 is a coating which dissolves under gastric conditions (e.g., in accordance with one of the respective embodiments described herein), external layer 220 comprises one or more antacid compounds (e.g., in accordance with one of the respective embodiments described herein), and core 210 comprises a therapeutically active agent and SNAC, and optionally one or more antacid compounds (e.g., in accordance with one of the respective embodiments described herein). In such embodiments, initial dissolution of the unit dosage form 200 in the gastrointestinal tract primarily comprises dissolution of coating 230 and external layer 220 in the stomach, thereby releasing the antacid compound(s) in the external layer and reducing an acidity in the stomach (e.g., in a vicinity of the unit dosage form) prior to release of therapeutically active agent and SNAC from core 210.

In some embodiments of any one of the embodiments wherein coating 230 is a coating which dissolves under gastric conditions, external layer 220 and/or core 210 is devoid of a protease inhibitor.

In some embodiments of any one of the embodiments described herein, unit dosage form 200 is formulated as a coated tablet. In some embodiments, the unit dosage form 200 is formulated as a coated multi-layered tablet (e.g., 3-layered tablet), in which external layer 220 forms an upper layer and a lower layer, and core 210 is formulated as a middle layer sandwiched between the upper layer and a lower layer. An exemplary coated tablet is shown in FIG. 4. Any of the coated multi-layered tablets described herein may optionally prepared using any technique known in the art for preparing multi-layered tablets, followed by coating the tablet using any tablet-coating technique known in the art.

FIG. 3 shows the structure of an exemplary unit dosage form according to some embodiments of the invention, in a form of tablet 300. Tablet 300 comprises a core 310 and an external layer 320, which correspond, respectively, to core 110 and external layer 120 of unit dosage form 100, as described herein in any one of the respective embodiments (e.g., with respect to FIG. 1B).

Tablet 300 is optionally has a substantially circular or substantially oval cross-section in cross-section (as depicted in FIG. 3). However, the tablet may have a differently shape, and it is to be understood that the shape depicted in FIG. 3 is not intended to be limiting.

External layer 320 includes layer 330 on an obverse face (e.g., a circular or oval face) and layer 340 on a reverse face (e.g., a circular or oval face) of tablet 300. Layers 330 and 340 are optionally unconnected, such that external layer 320 is separated into two unconnected layers, corresponding to external layer 120 in FIG. 1B).

External layer 320 optionally covers at least 50% of a surface area of core 310, optionally at least 60%, optionally at least 70%, optionally at least 80%, and optionally at least 90% of the surface of core 310.

External layer 320 comprises one or more protease inhibitors and/or antacid compounds, as described for external layer 120 according to any one of the respective embodiments described herein. In some embodiments, external layer 320 comprises one or more antacid compounds (e.g., in accordance with one of the respective embodiments described herein).

In some embodiments of any one of the embodiments described herein, external layer 320 is devoid of protease inhibitors. Optionally, external layer 320 consists essentially of one or more antacid compounds. Alternatively, external layer 320 comprises a combination of one or more excipients with the antacid compound(s) (e.g., in accordance with one of the respective embodiments described herein).

In some embodiments of any one of the embodiments described herein, external layer 320 comprises one or more protease inhibitors in addition to one or more antacid compounds (e.g., in accordance with one of the respective embodiments described herein). Optionally, external layer 320 consists essentially of one or more protease inhibitors and one or more antacid compounds. Alternatively, external layer 320 comprises a combination of one or more excipients with the protease inhibitor(s) and antacid compound(s) (e.g., in accordance with one of the respective embodiments described herein).

Core 310 comprises the therapeutically active agent of the tablet and SNAC, and optionally further comprises one or more protease inhibitors and/or antacid compounds, as described for core 110 according to any one of the respective embodiments described herein. In some embodiments, core 310 comprises one or more antacid compounds (e.g., in accordance with one of the respective embodiments described herein).

Initial dissolution of tablet 300 in the gastrointestinal system primarily comprises dissolution of external layer 320, thereby releasing the protease inhibitor(s) and/or antacid compound(s) in the external layer prior to release of the therapeutically active agent and SNAC from core 310.

FIG. 4 shows the structure, in cross-section, of an exemplary unit dosage form according to some embodiments of the invention, in a form of coated tablet 400. Tablet 400 corresponds to tablet 300 (in any one of the respective embodiments described herein), differing in that tablet 400 further comprises enteric coating 430. Tablet 400 comprises a core 410, an external layer 420, and an enteric coating 430, which correspond, respectively, to core 210, external layer 220 and coating 230 of unit dosage form 200, as described herein, in any one of the respective embodiments (e.g., with respect to FIG. 2B).

Enteric coating 430 may optionally be an enteric coating according to any one of the embodiments described herein relating to an enteric coating, for example, with respect to coating 230 (e.g., in accordance with one of the respective embodiments).

Tablet 400 optionally has a substantially circular or substantially oval cross-section in cross-section (as depicted in FIG. 4). However, the tablet may have a differently shape, and it is to be understood that the shape depicted in FIG. 4 is not intended to be limiting.

External layer 420 includes layer 440 on an obverse face (e.g., a circular or oval face) and layer 450 on a reverse face (e.g., a circular or oval face) of tablet 400. Layers 440 and 450 are optionally unconnected, such that external layer 420 is separated into two unconnected layers, corresponding to external layer 220 in FIG. 2B).

External layer 420 optionally covers at least 50% of a surface area of core 410, optionally at least 60%, optionally at least 70%, optionally at least 80%, and optionally at least 90% of the surface of core 410.

External layer 420 comprises one or more protease inhibitors and/or antacid compounds, as described for external layer 120 and/or external layer 220 according to any one of the respective embodiments described herein. In some embodiments of any one of the embodiments described herein, external layer 420 is devoid of antacid compounds. Optionally, external layer 420 consists essentially of one or more protease inhibitors. Alternatively, external layer 420 comprises a combination of one or more excipients with the protease inhibitor(s).

Core 410 comprises the therapeutically active agent of the tablet and SNAC, and optionally further comprises one or more protease inhibitors and/or antacid compounds, as described for core 110 and/or core 210 according to any one of the respective embodiments described herein. In some embodiments, core 410 comprises one or more protease inhibitors. In some embodiments, core 410 is devoid of antacid compounds.

Dissolution of tablet 400 in the gastrointestinal system comprises dissolution of enteric coating 430 in the intestines, followed primarily by dissolution of external layer 420, thereby releasing the protease inhibitor(s) in the external layer prior to release of therapeutically active agent and SNAC from core 410.

Figure 5:
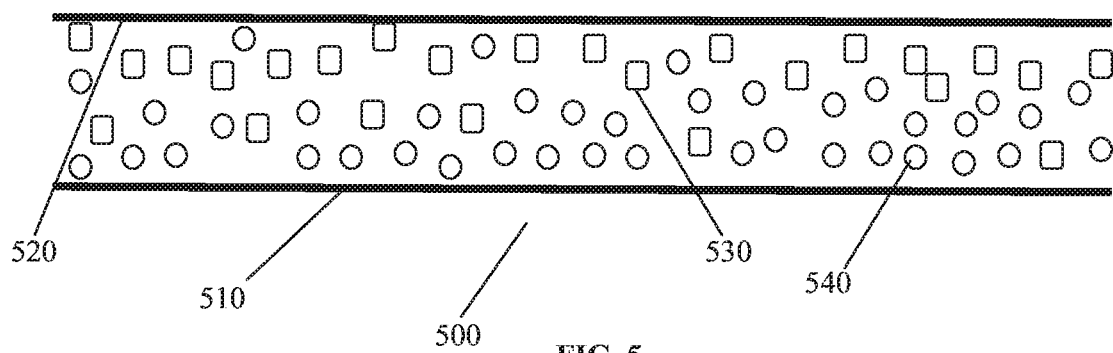
FIG. 5 depicts an exemplary external layer of a unit dosage form according to some embodiments of the invention.

FIG. 5 shows a composition of an exemplary external layer 500 according to some of any one of the embodiments of the invention. External layer 500 corresponds to any external layer described herein (e.g., external layer 120, 220, 320 and/or 420), in any one of the respective embodiments described herein, and has an inner face 510 which faces a core as described herein, and an outer face 520, which faces a coating described herein and/or surface of a unit dosage device described herein. External layer 500 comprises a first compound 530 (optionally a single compound, and optionally a combination of compounds) depicted as rectangles, and a second compound 540 (optionally a single compound, and optionally a combination of compounds) depicted as circles. Additional compounds (not shown) may optionally also be comprised by external layer 500.

The distribution of compounds 530 and 540 is optionally inhomogeneous, such that compound 530 is more concentrated in the vicinity of outer face 520 than in the vicinity of inner face 510, and/or compound 540 is more concentrated in the vicinity of inner face 510 than in the vicinity of outer face 520, as depicted in FIG. 5. Thus, a gradient in concentration exists between faces 510 and 520. In some embodiments, dissolution of external layer 500 results in dissolution of compound 530 preceding dissolution of compound 540.

Alternatively, the distribution of compounds 530 and 540 is homogeneous, such that no gradient in concentration exists between faces 510 and 520.

In some of any of the embodiments described herein, compound 530 is one or more antacid compounds (e.g., in accordance with one of the respective embodiments described herein), and compound 540 is one or more protease inhibitor(s) and/or excipient(s) (e.g., in accordance with one of the respective embodiments described herein).

In some of any of the embodiments described herein, compound 530 is one or more protease inhibitors (e.g., in accordance with one of the respective embodiments described herein), and compound 540 is one or more antacid compound(s) and/or excipient(s) (e.g., in accordance with one of the respective embodiments described herein).

Figure 6:
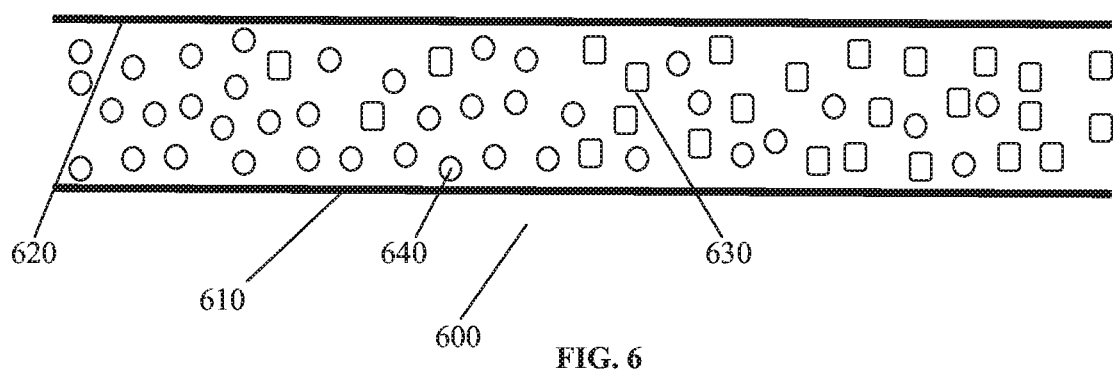
FIG. 6 depicts an exemplary external layer of a unit dosage form according to some embodiments of the invention.

FIG. 6 shows a composition of an exemplary external layer 600 according to some of any one of the embodiments of the invention. External layer 600 corresponds to any external layer described herein (e.g., external layer 120, 220, 320, 420 and/or 520), in any one of the respective embodiments described herein, and has an inner face 610 which faces a core as described herein, and an outer face 620, which faces a coating described herein and/or surface of a unit dosage device described herein. External layer 600 comprises a first compound 630 (optionally a single compound, and optionally a combination of compounds) depicted as rectangles, and a second compound 640 (optionally a single compound, and optionally a combination of compounds) depicted as circles. Additional compounds (not shown) may optionally also be comprised by external layer 600.

As depicted in FIG. 6, the distribution of compounds 630 and 640 is optionally inhomogeneous, such that compound 630 is more concentrated in the vicinity of one or more regions of the unit dosage form surface (e.g., the right-hand side of FIG. 6) than in the vicinity of other regions of the unit dosage form surface (e.g., the left-hand side of FIG. 6), and/or compound 540 is more concentrated in the vicinity of one or more regions of the unit dosage form surface (e.g., the left-hand side of FIG. 6) than in the vicinity of other regions of the unit dosage form surface (e.g., the right-hand side of FIG. 6). Thus, a gradient in concentration exists in the plane of external layer 600.

Alternatively, the distribution of compounds 630 and 640 is homogeneous, such that no gradient in concentration exists in the plane of external layer 600.

In some of any of the embodiments described herein, compound 630 is one or more antacid compounds (e.g., in accordance with one of the respective embodiments described herein), and compound 640 is one or more protease inhibitor(s) and/or excipient(s) (e.g., in accordance with one of the respective embodiments described herein).

In some of any of the embodiments described herein, compound 630 is one or more protease inhibitors (e.g., in accordance with one of the respective embodiments described herein), and compound 640 is one or more antacid compound(s) and/or excipient(s) (e.g., in accordance with one of the respective embodiments described herein).

Figure 7:
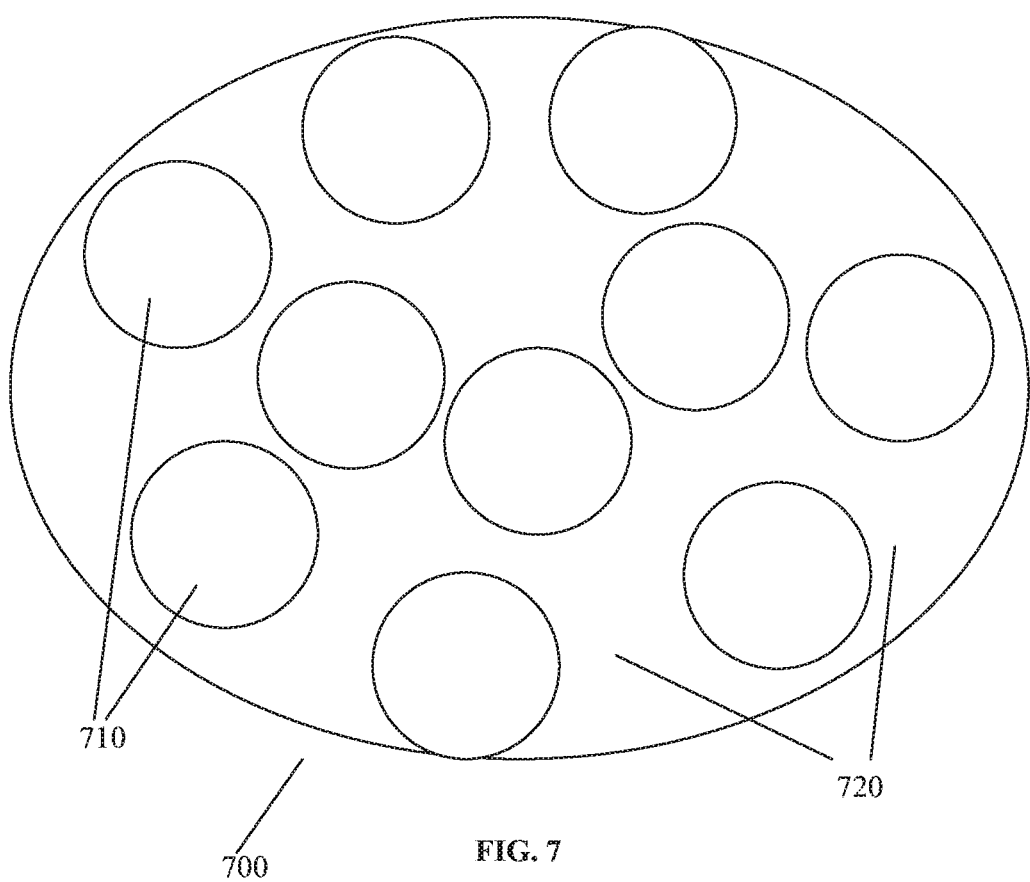
FIG. 7 depicts an exemplary core of a unit dosage form according to some embodiments of the invention.

FIG. 7 shows a composition of an exemplary core 700 according to some of any one of the embodiments of the invention. Core 700 corresponds to any external layer described herein (e.g., core 110, 210, 310 and/or 410), in any one of the respective embodiments described herein, and may optionally be combined with any external layer described herein.

As depicted in FIG. 7, the distribution of one or more compounds in core 700 is optionally inhomogeneous, such that the one or more compounds are concentrated within particles 710 separated at least in part by an interstitial material 720.

Particles 710 optionally comprise the therapeutically active agent and/or SNAC (e.g., in accordance with one of the respective embodiments described herein), at a concentration which is higher than a concentration of the therapeutically active agent and/or SNAC in interstitial material 720. Particles 710 may include different species of particles, having different compositions (e.g., one species comprising SNAC, and one species comprising a therapeutically active agent). Particles 710 are optionally in a form of granules and/or microspheres.

Interstitial material 720 is optionally devoid of therapeutically active agent and/or SNAC. Interstitial material 720 optionally comprises on or more excipients (e.g., in accordance with one of the respective embodiments described herein), such as a filler and/or binder, and optionally consists essentially of one or more excipients.

Alternatively, the distribution of compounds in core 700 is homogeneous.

In some embodiments of any one of the embodiments described herein, at least 50 weight percents of a core described herein (e.g., any one of cores 110, 210, 310 and 410) consists of SNAC. In some embodiments, at least 60 weight percents of a core described herein (e.g., any one of cores 110, 210, 310 and 410) consists of SNAC. In some embodiments, at least 70 weight percents of a core described herein (e.g., any one of cores 110, 210, 310 and 410) consists of SNAC. In some embodiments, at least 80 weight percents of a core described herein (e.g., any one of cores 110, 210, 310 and 410) consists of SNAC. In some embodiments, at least 90 weight percents of a core described herein (e.g., any one of cores 110, 210, 310 and 410) consists of SNAC.

Without being bound by any particular theory, it is believed that compositions (e.g., unit dosage forms and/or cores described herein) having a large proportion of SNAC, which is a salt, tend to be readily soluble in aqueous solution, including in gastric fluid, as is desirable according to some embodiments of the invention.

In some embodiments of any one of the embodiments described herein, the unit dosage form (e.g., any one of unit dosage form 100, unit dosage form 200, and tablet 300) is soluble in gastric fluid. In some such embodiments, the unit dosage form does not comprise an enteric coating, thereby facilitating dissolution in gastric fluid. In some embodiments, the unit dosage form dissolves in gastric fluid in no more than 60 minutes. In some embodiments, the unit dosage form dissolves in gastric fluid in no more than 50 minutes. In some embodiments, the unit dosage form dissolves in gastric fluid in no more than 40 minutes. In some embodiments, the unit dosage form dissolves in gastric fluid in no more than 30 minutes. In some embodiments, the unit dosage form dissolves in gastric fluid in no more than 20 minutes. In some embodiments, the unit dosage form dissolves in gastric fluid in no more than 15 minutes. In some embodiments, the unit dosage form dissolves in gastric fluid in no more than 10 minutes. In some embodiments, the unit dosage form dissolves in gastric fluid in no more than 5 minutes.

In some embodiments of any one of the embodiments described herein, the unit dosage form (e.g., any one of unit dosage form 100, unit dosage form 200, and tablet 300) is not soluble in gastric fluid.

Herein throughout, the phrases "soluble in gastric fluid", "dissolves in gastric fluid" and the like refer to solubility of a composition in simulated gastric fluid without pepsin, at pH 2.0, under conditions according to USP 23 Apparatus 2 (paddle) (e.g., 800 ml volume, 50 rotations per minute). Dissolution is indicated by absence of visible composition at the bottom of the fluid. However, visible material suspended in the liquid is not excluded by the terms "soluble" and "dissolution". The phrase "soluble in gastric fluid" refers herein to dissolution within a period of 6 hours. A liquid composition miscible with simulated gastric fluid is considered herein to be "soluble in gastric fluid", wherein the dissolution is the mixing of the liquid composition with the simulated gastric fluid.

In some embodiments of any one of the embodiments described herein, the unit dosage form is formulated such that absorption of the therapeutically active agent following oral administration of the unit dosage form is characterized by a bioavailability of the therapeutically active agent which is at least 10% higher than a bioavailability of the therapeutically active agent following oral administration of a unit dosage form composition consisting of the core of the aforementioned unit dosage form, without the external layer described herein. In some embodiments, the bioavailability is at least 20% higher than (120% of the level of) the bioavailability upon oral administration of the core. In some embodiments, the bioavailability is at least 50% higher than (150% of the level of) the bioavailability upon oral administration of the core. In some embodiments, the bioavailability is at least twice (200% of the level of) the bioavailability upon oral administration of the core. In some embodiments, the bioavailability is at least four-fold (400% of the level of) the bioavailability upon oral administration of the core. In some embodiments, the bioavailability is at least ten-fold (1000% of the level of) the bioavailability upon oral administration of the core. In some embodiments, the bioavailability is at least twenty-fold (2000% of the level of) the bioavailability upon oral administration of the core.

Without being bound by any particular theory, it is believed that the protective agent significantly enhances bioavailability by protecting SNAC and thereby increasing the amount of active SNAC which remains available for enhancing absorption of the therapeutically active agent; and/or by protecting the therapeutically active agent and thereby increasing the amount of therapeutically active agent which remains active upon absorption. It is further believed that the protective agent lengthens the period of time during which significant absorption of the therapeutically active agent occurs (e.g., resulting in a broader peak of plasma levels of the agent as a function of time), by lengthening the time during which the SNAC and/or therapeutically active agent remains in active form in the gastrointestinal tract, in addition to increasing the magnitude of absorption (by enhancing bioavailability).

Compositions Comprising Antacid:

According to an aspect of some embodiments of the invention, there is provided a pharmaceutical composition for oral administration of a therapeutically active agent, the composition comprising a therapeutically active agent (e.g., as described herein), SNAC and at least one antacid compound.

In some embodiments, the composition is in a form of a homogeneous mixture, such that the antacid compound is uniformly dispersed among the SNAC and therapeutically active agent (and optionally any additional ingredient present).

In some embodiments, the composition further comprises at least one protease inhibitor (e.g., one or more protease inhibitors as described herein).

In some embodiments, the composition is formulated as a unit dosage form. The unit dosage form may be formulated in any form suitable for oral administration, including solid and/or liquid forms. In some embodiments, the unit dosage form is a solid unit dosage form. In some embodiments, the composition is formulated as a tablet. In some embodiments, the unit dosage form (e.g., solid unit dosage form) is soluble in gastric fluid. In some embodiments, the unit dosage form dissolves in gastric fluid in no more than 60 minutes. In some embodiments, the unit dosage form dissolves in gastric fluid in no more than 50 minutes. In some embodiments, the unit dosage form dissolves in gastric fluid in no more than 40 minutes. In some embodiments, the unit dosage form dissolves in gastric fluid in no more than 30 minutes. In some embodiments, the unit dosage form dissolves in gastric fluid in no more than 20 minutes. In some embodiments, the unit dosage form dissolves in gastric fluid in no more than 15 minutes. In some embodiments, the unit dosage form dissolves in gastric fluid in no more than 10 minutes. In some embodiments, the unit dosage form dissolves in gastric fluid in no more than 5 minutes.

In some embodiments, the unit dosage form (e.g., solid unit dosage form) is not soluble in gastric fluid.

In some embodiments of any one of the embodiments described herein, the composition consists primarily of the combination of therapeutically active agent, SNAC, and at least one antacid compound described herein, that is, at least 50 weight percents of the composition consists of ingredients selected from the group consisting of a therapeutically active agent, SNAC and at least one antacid compound. In some embodiments, at least 60 weight percents of the composition consists of a therapeutically active agent, SNAC and at least one antacid compound. In some embodiments, at least 70 weight percents of the composition consists of a therapeutically active agent, SNAC and at least one antacid compound. In some embodiments, at least 80 weight percents of the composition consists of a therapeutically active agent, SNAC and at least one antacid compound. In some embodiments, at least 90 weight percents of the composition consists of a therapeutically active agent, SNAC and at least one antacid compound. In some embodiments, at least 95 weight percents of the composition consists of a therapeutically active agent, SNAC and at least one antacid compound. In some embodiments, at least 98 weight percents of the composition consists of a therapeutically active agent, SNAC and at least one antacid compound. In some embodiments, the composition is formulated as a tablet.

In some embodiments of any one of the embodiments described herein, the composition optionally further comprises at least one protease inhibitor, and at least 50 weight percents of the composition consists of ingredients selected from the group consisting of a therapeutically active agent, SNAC, at least one antacid compound and at least one protease inhibitor. In some embodiments, at least 60 weight percents of the composition consists of a therapeutically active agent, SNAC, at least one antacid compound and at least one protease inhibitor. In some embodiments, at least 70 weight percents of the composition consists of a therapeutically active agent, SNAC, at least one antacid compound and at least one protease inhibitor. In some embodiments, at least 80 weight percents of the composition consists of a therapeutically active agent, SNAC, at least one antacid compound and at least one protease inhibitor. In some embodiments, at least 90 weight percents of the composition consists of a therapeutically active agent, SNAC, at least one antacid compound and at least one protease inhibitor. In some embodiments, at least 95 weight percents of the composition consists of a therapeutically active agent, SNAC, at least one antacid compound and at least one protease inhibitor. In some embodiments, at least 98 weight percents of the composition consists of a therapeutically active agent, SNAC, at least one antacid compound and at least one protease inhibitor. In some embodiments, the composition is formulated as a tablet.

In some embodiments of any one of the embodiments described herein, at least 50 weight percents the composition consists of SNAC. In some embodiments, at least 60 weight percents of composition consists of SNAC. In some embodiments, at least 70 weight percents of composition consists of SNAC. In some embodiments, at least 80 weight percents of composition consists of SNAC. In some embodiments, at least 90 weight percents of composition consists of SNAC.

In some embodiments of any one of the embodiments described herein, the composition is formulated such that a bioavailability of the therapeutically active agent upon oral administration of the composition is at least 10% higher than a bioavailability of the therapeutically active agent upon oral administration of a composition comprising the therapeutically active agent and SNAC without the at least one antacid compound (e.g., being identical in all aspects except for the absence of the antacid compound(s)). In some embodiments, the bioavailability is at least 20% higher than (120% of the level of) the bioavailability upon oral administration of a composition comprising the therapeutically active agent and SNAC without the at least one antacid compound. In some embodiments, the bioavailability is at least 50% higher than (150% of the level of) the bioavailability upon oral administration of a composition comprising the therapeutically active agent and SNAC without the at least one antacid compound. In some embodiments, the bioavailability is at least twice (200% of the level of) the bioavailability upon oral administration of a composition comprising the therapeutically active agent and SNAC without the at least one antacid compound. In some embodiments, the bioavailability is at least four-fold (400% of the level of) the bioavailability upon oral administration of a composition comprising the therapeutically active agent and SNAC without the at least one antacid compound. In some embodiments, the bioavailability is at least ten-fold (1000% of the level of) the bioavailability upon oral administration of a composition comprising the therapeutically active agent and SNAC without the at least one antacid compound. In some embodiments, the bioavailability is at least twenty-fold (2000% of the level of) the bioavailability upon oral administration of a composition comprising the therapeutically active agent and SNAC without the at least one antacid compound.

Co-Administration of Antacid with SNAC and Therapeutically Effective Agent:

An antacid compound may be utilized advantageously in combination with a therapeutically active agent and SNAC, without necessarily combining all of the ingredients in a single composition.

According to another aspect of embodiments of the invention, there is provided a method of treating a condition treatable by oral administration of a therapeutically active agent in a subject in need thereof, the method comprising co-administering to the subject, an antacid composition comprising at least one antacid compound, as defined herein (e.g., at least one antacid compound described herein), and/or at least one gastric acid secretion inhibitor; and a composition comprising the therapeutically active agent (e.g., as described herein) and SNAC.

As used herein, the phrase "gastric acid secretion inhibitor" refers to any agent which reduces secretion of acid into the stomach, although it does not necessarily have any effect on acid which has already been secreted. Examples of gastric acid secretion inhibitors which may be used in any of the embodiments described herein relating to an antacid composition include, without limitation, $H_2$ receptor antagonists, such as cimetidine, famotidine, nizatidine and ranitidine; and proton pump inhibitors, such as omeprazole, lansoprazole, dexlansoprazole, esomeprazole, rabeprazole and ilaprazole.

According to another aspect of embodiments of the invention, there is provided a use of a composition comprising a therapeutically active agent and SNAC in the preparation of a medicament for use in the treatment of a condition treatable by oral administration of the therapeutically active agent in a subject in need thereof, wherein the treatment comprises co-administering an antacid composition comprising at least one antacid compound, as defined herein (e.g., at least one antacid compound described herein), and/or at least one gastric acid secretion inhibitor, with the medicament.

According to another aspect of embodiments of the invention, there is provided a composition comprising a therapeutically active agent and SNAC, for use in the treatment of a condition treatable by oral administration of the therapeutically active agent in a subject in need thereof, wherein the treatment comprises co-administering an antacid composition comprising at least one antacid compound, as defined herein (e.g., at least one antacid compound described herein), and/or at least one gastric acid secretion inhibitor, with the composition.

In some embodiments of any one of the embodiments described herein relating to co-administering an antacid composition, the antacid composition is optionally any antacid composition known in the art (e.g., a commercially available antacid composition).

In some embodiments of any one of the embodiments described herein relating to co-administering an antacid composition, the co-administering comprises administering the antacid composition prior to or concomitantly with the composition comprising the therapeutically active agent and SNAC.

In some embodiments of any one of the embodiments described herein relating to co-administering an antacid composition concomitantly with the composition comprising the therapeutically active agent and SNAC, the antacid composition comprises at least one antacid compound, as defined herein (e.g., in accordance with any of the respective embodiments described herein).

In some embodiments of any one of the embodiments described herein relating to co-administering an antacid composition comprising at least one gastric acid secretion inhibitor, the co-administering comprises administering the antacid composition prior to the composition comprising the therapeutically active agent and SNAC (e.g., in accordance with any of the respective embodiments described herein).

Without being bound by any particular theory, it is believed that antacid compounds as defined herein (compounds capable of neutralizing stomach acid) are generally effective at reducing acidity in the stomach and/or in a region thereof immediately (as neutralization of acid occurs as a relatively rapid chemical reaction) but may have a limited long-term effect due to secretion of additional acid into the stomach, and are therefore particularly effective when administered concomitantly with or shortly (e.g., no more than 90 minutes) prior to the composition comprising the therapeutically active agent and SNAC.

It is further believed that gastric acid secretion inhibitors are generally effective at reducing stomach acidity for a relatively long duration (due to long-term inhibition of gastric acid secretion) but may have a limited effect on acidity immediately after administration due to an absence of a significant effect on acid which is already present in the stomach, and are therefore particularly effective when administered prior to the composition comprising the therapeutically active agent and SNAC.

Herein, the term "concomitantly" refers to an events (e.g., administration of an antacid composition) being within a time period of from 5 minutes before to 5 minutes after another event (e.g., administration of a composition comprising a therapeutically active agent and SNAC), and in some embodiments, within a time period of from one minute before to one minute after the other event.

In some embodiments, concomitant co-administration is effected by swallowing the two compositions simultaneously.

In some embodiments of any one of the embodiments described herein relating to co-administering at least one antacid composition, administering the antacid composition prior to the composition comprising the therapeutically active agent and SNAC comprises administering the antacid composition no more than 5 days prior to the composition comprising the therapeutically active agent and SNAC. In some embodiments, the antacid composition is administered no more than 4 days prior to the composition comprising the therapeutically active agent and SNAC. In some embodiments, the antacid composition is administered no more than 3 days prior to the composition comprising the therapeutically active agent and SNAC. In some embodiments, the antacid composition is administered no more than 2 days prior to the composition comprising the therapeutically active agent and SNAC. In some embodiments, the antacid composition is administered no more than 1 day (24 hours) prior to the composition comprising the therapeutically active agent and SNAC. In some embodiments, the antacid composition comprises a proton-pump inhibitor.

In some embodiments of any one of the embodiments described herein relating to co-administering at least one antacid composition, the antacid composition is administered at least about 1 day (e.g., at least about 24 hours) prior to the composition comprising the therapeutically active agent and SNAC, for example, from about 1 to about 5 days (e.g., about 2 days to about 4 days, optionally about 3 days) prior to the composition comprising the therapeutically active agent and SNAC. In some embodiments, the antacid composition comprises a proton-pump inhibitor.

In some of any of the embodiments described herein in which the antacid composition is optionally administered at least 12 hours prior to the composition comprising the therapeutically active agent and SNAC, the antacid composition comprises a proton-pump inhibitor.

In some embodiments of any one of the embodiments described herein relating to co-administering at least one antacid composition, administering the antacid composition prior to the composition comprising the therapeutically active agent and SNAC comprises administering the antacid composition no more than 16 hours prior to the composition comprising the therapeutically active agent and SNAC. In some embodiments, the antacid composition is administered no more than 12 hours prior to the composition comprising the therapeutically active agent and SNAC. In some embodiments, the antacid composition is administered no more than 10 hours prior to the composition comprising the therapeutically active agent and SNAC. In some embodiments, the antacid composition is administered no more than 8 hours prior to the composition comprising the therapeutically active agent and SNAC. In some embodiments, the antacid composition is administered no more than 6 hours prior to the composition comprising the therapeutically active agent and SNAC. In some embodiments, the antacid composition is administered no more than 4 hours prior to the composition comprising the therapeutically active agent and SNAC. In some embodiments, the antacid composition comprises an $H_2$ receptor antagonist.

In some embodiments of any one of the embodiments described herein relating to co-administering at least one antacid composition, the antacid composition is administered at least about 2 hours prior to the composition comprising the therapeutically active agent and SNAC, for example, from about 2 to about 10 hours (e.g., 2 to 8 hours, 2 to 6 hours, 2 to 4 hours) prior to the composition comprising the therapeutically active agent and SNAC. In some embodiments, the antacid composition comprises an $H_2$ receptor antagonist or a proton pump inhibitor, as described herein. In some embodiments, the antacid composition comprises an $H_2$ receptor antagonist, as described herein.

In some of any of the embodiments described herein in which the antacid composition is optionally administered at least 2 hours prior to, but less than 12 hours prior to, the composition comprising the therapeutically active agent and SNAC, the antacid composition comprises an $H_2$ receptor antagonist, as described herein.

In some embodiments of any one of the embodiments described herein relating to co-administering at least one antacid composition, administering the antacid composition prior to the composition comprising the therapeutically active agent and SNAC comprises administering the antacid composition no more than 90 minutes prior to the composition comprising the therapeutically active agent and SNAC. In some embodiments, the antacid composition is administered no more than 60 minutes prior to the composition comprising the therapeutically active agent and SNAC. In some embodiments, the antacid composition is administered no more than 30 minutes prior to the composition comprising the therapeutically active agent and SNAC. In some embodiments, the antacid composition is administered no more than 20 minutes prior to the composition comprising the therapeutically active agent and SNAC. In some embodiments, the antacid composition is administered no more than 10 minutes prior to the composition comprising the therapeutically active agent and SNAC. In some embodiments, the antacid composition comprises an antacid compound (as defined herein).

In some embodiments of any one of the embodiments described herein relating to co-administering at least one antacid composition, the composition comprising the therapeutically active agent and SNAC is essentially the same as any one of the compositions described herein comprising a therapeutically active agent, SNAC and antacid compound(s), with the exception that no antacid compound is present.

In some embodiments, the composition comprising the therapeutically active agent and SNAC and/or the antacid composition further comprises at least one protease inhibitor (e.g., one or more protease inhibitors as described herein).

In some embodiments, the composition comprising the therapeutically active agent and SNAC and/or the antacid composition is formulated as a unit dosage form. The unit dosage form may be formulated in any form suitable for oral administration, including solid and/or liquid forms. In some embodiments, the unit dosage form (e.g., a unit dosage form of the composition comprising the therapeutically active agent and SNAC) is a solid unit dosage form. In some embodiments, the unit dosage form (e.g., a unit dosage form of the composition comprising the therapeutically active agent and SNAC) is formulated as a tablet.

In some embodiments, the composition comprising the therapeutically active agent and SNAC and the antacid composition (e.g., in solid form) are each soluble in gastric fluid (as defined herein). In some embodiments, the compositions each dissolve in gastric fluid in no more than 60 minutes. In some embodiments, the compositions each dissolve in gastric fluid in no more than 50 minutes. In some embodiments, the compositions each dissolve in gastric fluid in no more than 40 minutes. In some embodiments, the compositions each dissolve in gastric fluid in no more than 30 minutes. In some embodiments, the compositions each dissolve in gastric fluid in no more than 20 minutes. In some embodiments, the compositions each dissolve in gastric fluid in no more than 15 minutes. In some embodiments, the compositions each dissolve in gastric fluid in no more than 10 minutes. In some embodiments, the compositions each dissolve in gastric fluid in no more than 5 minutes.

In some embodiments, neither the composition comprising the therapeutically active agent and SNAC nor the antacid composition (e.g., in solid form) are soluble in gastric fluid (as defined herein).

In some embodiments of any one of the embodiments described herein relating to co-administering at least one antacid composition, absorption of the therapeutically active agent following the co-administration is characterized by a bioavailability of the therapeutically active agent which is at least 10% higher than a bioavailability of the therapeutically active agent following oral administration of the composition comprising the therapeutically active agent and SNAC without co-administering the antacid composition. In some embodiments, the bioavailability is at least 20% higher than (120% of the level of) the bioavailability without co-administering the antacid composition. In some embodiments, the bioavailability is at least 50% higher than (150% of the level of) the bioavailability without co-administering the antacid composition. In some embodiments, the bioavailability is at least twice (200% of the level of) the bioavailability without co-administering the antacid composition. In some embodiments, the bioavailability is at least four-fold (400% of the level of) the bioavailability without co-administering the antacid composition. In some embodiments, the bioavailability is at least ten-fold (1000% of the level of) the bioavailability without co-administering the antacid composition. In some embodiments, the bioavailability is at least twenty-fold (2000% of the level of) the bioavailability without co-administering the antacid composition.

Antacid Compound(s):

Any one or more of the antacid compounds described herein may be used in any one of the embodiments described herein which utilize an antacid compound.

In some embodiments, the at least one antacid compound is selected from the group consisting of calcium carbonate, calcium gluconate, calcium citrate, sodium carbonate, sodium bicarbonate, sodium gluconate, sodium citrate, sodium hydroxide, potassium carbonate, potassium bicarbonate, potassium gluconate, potassium citrate, potassium hydroxide, magnesium carbonate, magnesium gluconate, magnesium citrate, magnesium oxide and magnesium hydroxide.

In some embodiments, the at least one antacid compound is selected from the group consisting of calcium carbonate, calcium gluconate, sodium carbonate, sodium bicarbonate, sodium citrate, sodium hydroxide, potassium carbonate, potassium bicarbonate, potassium citrate, potassium hydroxide, magnesium carbonate, magnesium hydroxide, magnesium oxide, aluminum carbonate, and aluminum hydroxide.

In some embodiments, the at least one antacid compound the at least one antacid compound is selected from the group consisting of calcium carbonate, calcium citrate, sodium bicarbonate, sodium hydroxide, magnesium carbonate, magnesium citrate, magnesium hydroxide, magnesium oxide, aluminum carbonate, and aluminum hydroxide.

In some embodiments, the at least one antacid compound is selected from the group consisting of calcium carbonate, sodium carbonate, sodium bicarbonate, potassium bicarbonate, magnesium carbonate, magnesium hydroxide, magnesium oxide and aluminum hydroxide.

In some embodiments of any one of the embodiments described herein relating to an antacid compound, a total amount of antacid compound(s) in a core of a unit dosage form described herein and/or in a unit dosage form described herein, and/or in an antacid composition co-administered as described herein, is such that the at least one antacid compound comprises at least 0.00001 molar equivalent of base. In some embodiments, the at least one antacid compound comprises at least 0.00003 molar equivalent of base. In some embodiments, the at least one antacid compound comprises at least 0.0001 molar equivalent of base. In some embodiments, the at least one antacid compound comprises at least 0.0003 molar equivalent of base. In some embodiments, the at least one antacid compound comprises at least 0.001 molar equivalent of base. In some embodiments, the at least one antacid compound comprises at least 0.002 molar equivalent of base. In some embodiments, the at least one antacid compound comprises at least 0.003 molar equivalent of base. In some embodiments, the at least one antacid compound comprises at least 0.005 molar equivalent of base. In some embodiments, the at least one antacid compound comprises at least 0.01 molar equivalent of base. In some embodiments, the at least one antacid compound comprises no more than 0.03 molar equivalent of base.

Herein, 1 molar equivalent of base refers to an amount of a basic compound (e.g., an antacid compound described herein) capable of neutralizing 1 mole of HCl (e.g., in an aqueous solution). In determining molar equivalents of base in antacid compounds described herein, each mole of hydroxide ion and/or bicarbonate ion is considered to be capable of neutralizing 1 mole of HCl, each mole of carbonate ion is considered to be capable of neutralizing 2 moles of HCl, and each mole of citrate ion (if fully deprotonated) is considered to be capable of neutralizing 3 moles of HCl.

In some embodiments of any one of the embodiments described herein relating to an antacid compound, a total amount of antacid compound(s) in a core of a unit dosage form described herein and/or in a unit dosage form described herein, and/or in an antacid composition co-administered as described herein, is at least 0.5 mg. In some embodiments, the amount of antacid compound(s) is at least 1 mg. In some embodiments, the amount of antacid compound(s) is at least 2 mg. In some embodiments, the amount of antacid compound(s) is at least 5 mg. In some embodiments, the amount of antacid compound(s) is at least 10 mg. In some embodiments, the amount of antacid compound(s) is at least 25 mg. In some embodiments, the amount of antacid compound(s) is at least 50 mg. In some embodiments, the amount of antacid compound(s) is at least 100 mg. In some embodiments, the amount of antacid compound(s) is at least 200 mg. In some embodiments, the amount of antacid compound(s) is at least 300 mg. In some embodiments, the amount of antacid compound(s) is at least 400 mg. In some embodiments, the amount of antacid compound(s) is at least 500 mg.

Protease Inhibitor(s):

In some embodiments of any one of the embodiments described herein, the at least one protease inhibitor included in any of the compositions (including composition unit dosage forms) described herein comprises at least one trypsin inhibitor. In some embodiments, the at least one protease inhibitor consists essentially of one or more trypsin inhibitor(s).

Examples of trypsin inhibitor which may be utilized in any one of the embodiments described herein include, without limitation, lima bean trypsin inhibitor, aprotinin, soybean trypsin inhibitor, ovomucoid trypsin inhibitor and any combination thereof. In some embodiments, the at least one trypsin inhibitor comprises soybean trypsin inhibitor (SBTI). In some embodiments, the at least one trypsin inhibitor (an optionally the at least one protease inhibitor) consists essentially of SBTI.

In some embodiments of any of the embodiments described herein, the at least one protease inhibitor comprises at least one serpin. In some embodiments, the at least one protease inhibitor consists essentially of one or more serpin(s).

Examples of serpins which may be utilized in any one of the embodiments described herein, include, without limitation, alpha 1-antitrypsin, antitrypsin-related protein, alpha 1-antichymotrypsin, kallistatin, protein C inhibitor, cortisol binding globulin, thyroxine-binding globulin, angiotensinogen, centerin, protein Z-related protease inhibitor, vaspin, monocyte/neutrophil elastase inhibitor, plasminogen activator inhibitor-2, squamous cell carcinoma antigen-1 (SCCA-1), squamous cell carcinoma antigen-2 (SCCA-2), maspin, proteinase inhibitor 6 (PI-6), megsin, serpin B8 (PI-8), serpin B9 (PI-9), bomapin, yukopin, hurpin/headpin, antithrombin, heparin cofactor II, plasminogen activator inhibitor 1, glia-derived nexin, pigment epithelium derived factor, alpha 2-antiplasmin, complement 1-inhibitor, 47 kDa heat shock protein (HSP47), neuroserpin and pancpin.

In some embodiments of any of the embodiments described herein, the at least one protease inhibitor comprises at least one cysteine protease inhibitor. In some embodiments, the at least one protease inhibitor consists essentially of one or more cysteine protease inhibitor(s).

Examples of cysteine protease inhibitors which may be utilized in any one of the embodiments described herein include, without limitation, type 1 cystatins, type 2 cystatins, human cystatins C, D, S, SN, and SA, cystatin E/M, cystatin F, and type 3 cystatins (including kininogens).

In some embodiments of any of the embodiments described herein, the at least one protease inhibitor comprises at least one threonine protease inhibitor. In some embodiments, the at least one protease inhibitor consists essentially of one or more threonine protease inhibitor(s).

Examples of threonine protease inhibitors which may be utilized in any one of the embodiments described herein include, without limitation, bortezomib, MLN-519, ER-807446 and TMC-95A.

In some embodiments of any of the embodiments described herein, the at least one protease inhibitor comprises at least one aspartic protease inhibitor. In some embodiments, the at least one protease inhibitor consists essentially of one or more aspartic protease inhibitor(s).

Examples of aspartic protease inhibitors which may be utilized in any one of the embodiments described herein include, without limitation, $\alpha_2$-macroglobulin, pepstatin A, aspartic protease inhibitor 11, aspartic protease inhibitor 1, aspartic protease inhibitor 2, aspartic protease inhibitor 3, aspartic protease inhibitor 4, aspartic protease inhibitor 5, aspartic protease inhibitor 6, aspartic protease inhibitor 7, aspartic protease inhibitor 8, aspartic protease inhibitor 9, pepsin inhibitor Dit33, and protease A inhibitor 3.

In some embodiments of any of the embodiments described herein, the at least one protease inhibitor comprises at least one metalloprotease inhibitor. In some embodiments, the at least one protease inhibitor consists essentially of one or more metalloprotease inhibitor(s).

Examples of metalloprotease inhibitors which may be utilized in any one of the embodiments described herein, include, without limitation, angiotensin-1-converting enzyme inhibitory peptide, antihemorrhagic factor BJ46a, beta-casein, proteinase inhibitor CeKI, venom metalloproteinase inhibitor DM43, carboxypeptidase A inhibitor, smpI, IMPI, alkaline proteinase, latexin, carboxypeptidase inhibitor, antihemorrhagic factor HSF, testican-3, SPOCK3, TIMP1, metalloproteinase inhibitor 1, metalloproteinase inhibitor 2, TIMP2, metalloproteinase inhibitor 3, TIMP3, metalloproteinase inhibitor 4, TIMP4, putative metalloproteinase inhibitor tag-225, tissue inhibitor of metalloprotease, WAP, kazal inhibitor, immunoglobulin, and kunitz and NTR domain-containing protein 1.

Examples of protease inhibitors which may be utilized in any one of the embodiments described herein also include, without limitation, AEBSF-HCl, ε-aminocaproic acid, α1antichymotypsin, antipain, antithrombin III, α1-antitrypsin, APMSF (4-amidinophenyl-methane sulfonyl-fluoride), sprotinin, benzamidine, chymostatin, DFP (diisopropylfluoro-phosphate), leupeptin, 4-(2-Aminoethyl)-benzenesulfonyl fluoride hydrochloride, PMSF (phenylmethyl sulfonyl fluoride), TLCK (1-chloro-3-tosylamido-7-amino-2-heptanone), TPCK (1-chloro-3-tosylamido-4-phenyl-2-butanone), pentamidine isothionate, pepstatin, guanidium, α2-macroglobulin, a chelating agent of zinc, and iodoacetate.

In some embodiments of any one of the embodiments described herein relating to a unit dosage form, the amount of a protease inhibitor in a unit dosage form described herein is at least about 0.1 mg. In some embodiments, the amount of a protease inhibitor in a unit dosage form described herein is at least about 0.2 mg. In some embodiments, the amount of a protease inhibitor in a unit dosage form described herein is at least about 0.3 mg. In some embodiments, the amount of a protease inhibitor in a unit dosage form described herein is at least about 0.4 mg. In some embodiments, the amount of a protease inhibitor in a unit dosage form described herein is at least about 0.6 mg. In some embodiments, the amount of a protease inhibitor in a unit dosage form described herein is at least about 0.8 mg. In some embodiments, the amount of a protease inhibitor in a unit dosage form described herein is at least about 1 mg. In some embodiments, the amount of a protease inhibitor in a unit dosage form described herein is at least about 1.5 mg. In some embodiments, the amount of a protease inhibitor in a unit dosage form described herein is at least about 2 mg. In some embodiments, the amount of a protease inhibitor in a unit dosage form described herein is at least about 2.5 mg. In some embodiments, the amount of a protease inhibitor in a unit dosage form described herein is at least about 3 mg. In some embodiments, the amount of a protease inhibitor in a unit dosage form described herein is at least about 5 mg. In some embodiments, the amount of a protease inhibitor in a unit dosage form described herein is at least about 7 mg. In some embodiments, the amount of a protease inhibitor in a unit dosage form described herein is at least about 10 mg. In some embodiments, the amount of a protease inhibitor in a unit dosage form described herein is at least about 12 mg. In some embodiments, the amount of a protease inhibitor in a unit dosage form described herein is at least about 15 mg. In some embodiments, the amount of a protease inhibitor in a unit dosage form described herein is at least about 20 mg. In some embodiments, the amount of a protease inhibitor in a unit dosage form described herein is at least about 30 mg. In some embodiments, the amount of a protease inhibitor in a unit dosage form described herein is at least about 50 mg. In some embodiments, the amount of a protease inhibitor in a unit dosage form described herein is at least about 70 mg. In some embodiments, the amount of a protease inhibitor in a unit dosage form described herein is at least about 100 mg.

In some embodiments of any one of the embodiments described herein relating to a unit dosage form, the amount of a protease inhibitor in a unit dosage form described herein is in a range of from 0.1 to 1 mg. In some embodiments, the amount of a protease inhibitor in a unit dosage form described herein is in a range of from 0.2 to 1 mg. In some embodiments, the amount of a protease inhibitor in a unit dosage form described herein is in a range of from 0.3 to 1 mg. In some embodiments, the amount of a protease inhibitor in a unit dosage form described herein is in a range of from 0.5 to 1 mg.

In some embodiments of any one of the embodiments described herein relating to a unit dosage form, the amount of a protease inhibitor in a unit dosage form described herein is in a range of from 0.1 to 2 mg. In some embodiments, the amount of a protease inhibitor in a unit dosage form described herein is in a range of from 0.2 to 2 mg. In some embodiments, the amount of a protease inhibitor in a unit dosage form described herein is in a range of from 0.3 to 2 mg. In some embodiments, the amount of a protease inhibitor in a unit dosage form described herein is in a range of from 0.5 to 2 mg. In some embodiments, the amount of a protease inhibitor in a unit dosage form described herein is in a range of from 1 to 2 mg.

In some embodiments of any one of the embodiments described herein relating to a unit dosage form, the amount of a protease inhibitor in a unit dosage form described herein is in a range of from 1 to 10 mg. In some embodiments, the amount of a protease inhibitor in a unit dosage form described herein is in a range of from 2 to 10 mg. In some embodiments, the amount of a protease inhibitor in a unit dosage form described herein is in a range of from 3 to 10 mg. In some embodiments, the amount of a protease inhibitor in a unit dosage form described herein is in a range of from 5 to 10 mg.

In some embodiments of any one of the embodiments described herein relating to a unit dosage form, the amount of a protease inhibitor in a unit dosage form described herein is in a range of from 1 to 20 mg. In some embodiments, the amount of a protease inhibitor in a unit dosage form described herein is in a range of from 2 to 20 mg. In some embodiments, the amount of a protease inhibitor in a unit dosage form described herein is in a range of from 3 to 20 mg. In some embodiments, the amount of a protease inhibitor in a unit dosage form described herein is in a range of from 5 to 20 mg. In some embodiments, the amount of a protease inhibitor in a unit dosage form described herein is in a range of from 10 to 20 mg.

In some embodiments of any one of the embodiments described herein relating to a unit dosage form, the amount of a protease inhibitor in a unit dosage form described herein is in a range of from 10 to 100 mg. In some embodiments, the amount of a protease inhibitor in a unit dosage form described herein is in a range of from 20 to 100 mg. In some embodiments, the amount of a protease inhibitor in a unit dosage form described herein is in a range of from 30 to 100 mg. In some embodiments, the amount of a protease inhibitor in a unit dosage form described herein is in a range of from 50 to 100 mg.

In some embodiments of any one of the embodiments described herein relating to a unit dosage form, the amount of a protease inhibitor in a unit dosage form described herein is in a range of from 10 to 200 mg. In some embodiments, the amount of a protease inhibitor in a unit dosage form described herein is in a range of from 20 to 200 mg. In some embodiments, the amount of a protease inhibitor in a unit dosage form described herein is in a range of from 30 to 200 mg. In some embodiments, the amount of a protease inhibitor in a unit dosage form described herein is in a range of from 50 to 200 mg. In some embodiments, the amount of a protease inhibitor in a unit dosage form described herein is in a range of from 100 to 200 mg.

In some embodiments of any one of the embodiments described herein relating to a unit dosage form, the amount of a protease inhibitor in a unit dosage form described herein is at least about 10 kallikrein inactivator units (k.i.u.). In some embodiments, the amount of a protease inhibitor in a unit dosage form described herein is at least about 12 k.i.u. In some embodiments, the amount of a protease inhibitor in a unit dosage form described herein is at least about 15 k.i.u. In some embodiments, the amount of a protease inhibitor in a unit dosage form described herein is at least about 20 k.i.u. In some embodiments, the amount of a protease inhibitor in a unit dosage form described herein is at least about 30 k.i.u. In some embodiments, the amount of a protease inhibitor in a unit dosage form described herein is at least about 40 k.i.u. In some embodiments, the amount of a protease inhibitor in a unit dosage form described herein is at least about 50 k.i.u. In some embodiments, the amount of a protease inhibitor in a unit dosage form described herein is at least about 70 k.i.u. In some embodiments, the amount of a protease inhibitor in a unit dosage form described herein is at least about 100 k.i.u. In some embodiments, the amount of a protease inhibitor in a unit dosage form described herein is at least about 150 k.i.u. In some embodiments, the amount of a protease inhibitor in a unit dosage form described herein is at least about 200 k.i.u. In some embodiments, the amount of a protease inhibitor in a unit dosage form described herein is at least about 300 k.i.u. In some embodiments, the amount of a protease inhibitor in a unit dosage form described herein is at least about 500 k.i.u. In some embodiments, the amount of a protease inhibitor in a unit dosage form described herein is at least about 700 k.i.u. In some embodiments, the amount of a protease inhibitor in a unit dosage form described herein is at least about 1000 k.i.u. In some embodiments, the amount of a protease inhibitor in a unit dosage form described herein is at least about 1500 k.i.u. In some embodiments, the amount of a protease inhibitor in a unit dosage form described herein is at least about 3000 k.i.u. In some embodiments, the amount of a protease inhibitor in a unit dosage form described herein is at least about 4000 k.i.u. In some embodiments, the amount of a protease inhibitor in a unit dosage form described herein is at least about 5000 k.i.u.

Herein and in the art, a "kallikrein inactivating unit" (k.i.u) refers to an amount of protease inhibitor that has the ability to inhibit 2 units of kallikrein by 50% (e.g., in aqueous solution at an optimal pH and solution volume for activity of the protease inhibitor).

In some embodiments of any one of the embodiments described herein relating to a composition and/or unit dosage form comprising a protease inhibitor and therapeutically active agent, a weight ratio of protease inhibitor to therapeutically active agent is in a range of from 1:1 to 5:1 (protease inhibitor: therapeutically active agent). In some embodiments, a weight ratio of protease inhibitor to therapeutically active agent is in a range of from 5:1 to 10:1. In some embodiments, a weight ratio of protease inhibitor to therapeutically active agent is in a range of from 10:1 to 20:1. In some embodiments, a weight ratio of protease inhibitor to therapeutically active agent is in a range of from 20:1 to 30:1. In some embodiments, a weight ratio of protease inhibitor to therapeutically active agent is in a range of from 30:1 to 40:1. In some embodiments, a weight ratio of protease inhibitor to therapeutically active agent is in a range of from 40:1 to 50:1. In some embodiments, a weight ratio of protease inhibitor to therapeutically active agent is in a range of from 50:1 to 75:1. In some embodiments, a weight ratio of protease inhibitor to therapeutically active agent is in a range of from 75:1 to 100:1. In some embodiments, a weight ratio of protease inhibitor to therapeutically active agent is in a range of from 100:1 to 200:1. In some embodiments, a weight ratio of protease inhibitor to therapeutically active agent is in a range of from 200:1 to 300:1. In some embodiments, a weight ratio of protease inhibitor to therapeutically active agent is in a range of from 300:1 to 400:1. In some embodiments, a weight ratio of protease inhibitor to therapeutically active agent is in a range of from 400:1 to 500:1. In some embodiments, the protease inhibitor is soybean trypsin inhibitor.

SNAC:

In some embodiments of any one of the embodiments described herein, the SNAC may optionally be replaced with a similar compound, such as SNAD (sodium 10-N-(2-hydroxybenzoyl)aminodecanoic acid). As shown below, the structure of SNAD differs from that of SNAC only in the length of the fatty acid moiety.

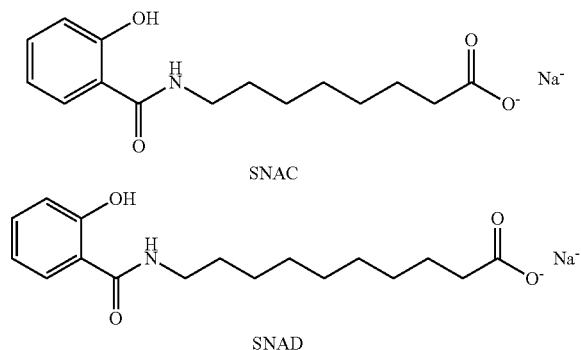

In some embodiments of any one of the embodiments described herein, the SNAC may optionally be replaced with a similar compound, wherein the caprylic acid moiety of SNAC is replaced by another fatty acid moiety at least 6 carbon atoms in length, for example, from 6 to 20 carbon atoms in length, optionally from 6 to 18 carbon atoms in length, optionally from 6 to 16 carbon atoms in length, optionally from 6 to 14 carbon atoms in length, optionally from 6 to 12 carbon atoms in length and optionally from 6 to 10 carbon atoms in length. The fatty acid moiety may be saturated (e.g., as are caprylic acid in SNAC and decanoic acid in SNAD) or unsaturated (i.e., comprising at least one unsaturated carbon-carbon bond).

In some embodiments of any one of the embodiments described herein, a concentration of SNAC in a composition described herein or in a core of a unit dosage form described herein is in a range of from 2.5 to 99.4 weight percents. In some of the aforementioned embodiments, the concentration of SNAC is in a range of from 2.5 to 10 weight percents. In some of the aforementioned embodiments, the concentration of SNAC is in a range of from 8 to 15 weight percents. In some of the aforementioned embodiments, the concentration of SNAC is in a range of from 10 to 20 weight percents. In some of the aforementioned embodiments, the concentration of SNAC is in a range of from 15 to 30 weight percents. In some of the aforementioned embodiments, the concentration of SNAC is in a range of from 20 to 40 weight percents. In some of the aforementioned embodiments, the concentration of SNAC is in a range of from 30 to 50 weight percents. In some of the aforementioned embodiments, the concentration of SNAC is in a range of from 40 to 60 weight percents. In some of the aforementioned embodiments, the concentration of SNAC is in a range of from 50 to 70 weight percents. In some of the aforementioned embodiments, the concentration of SNAC is in a range of from 2.5 to 10 weight percents. In some of the aforementioned embodiments, the concentration of SNAC is in a range of from 2.5 to 10 weight percents. In some of the aforementioned embodiments, the concentration of SNAC is in a range of from 70 to 99.4 weight percents.

In some embodiments of any one of the embodiments described herein, a weight ratio of SNAC to the therapeutically active agent in a composition described herein or in a core of a unit dosage form described herein is in a range of from 5:1 to 10:1 (SNAC: therapeutically active agent). In some embodiments, the ratio is about 7.5:1. In some embodiments, the composition or core further comprises a protease inhibitor. In some of the aforementioned embodiments wherein the composition comprises a protease inhibitor, a weight ratio of protease inhibitor to therapeutically active agent is in a range of from 1:1 to 5:1 (protease inhibitor: therapeutically active agent), optionally about 3:1. In some embodiments, a weight ratio of protease inhibitor to therapeutically active agent is in a range of from 5:1 to 10:1, optionally about 7.5:1. In some embodiments, a weight ratio of protease inhibitor to therapeutically active agent is in a range of from 10:1 to 20:1, optionally about 15:1. In some embodiments, a weight ratio of protease inhibitor to therapeutically active agent is in a range of from 20:1 to 30:1, optionally about 25:1. In some embodiments, a weight ratio of protease inhibitor to therapeutically active agent is in a range of from 30:1 to 40:1, optionally about 35:1. In some embodiments, a weight ratio of protease inhibitor to therapeutically active agent is in a range of from 40:1 to 50:1, optionally about 45:1. In some embodiments, a weight ratio of protease inhibitor to therapeutically active agent is in a range of from 50:1 to 75:1, optionally about 62.5:1. In some embodiments, a weight ratio of protease inhibitor to therapeutically active agent is in a range of from 75:1 to 100:1, optionally about 87.5:1. In some embodiments, a weight ratio of protease inhibitor to therapeutically active agent is in a range of from 100:1 to 200:1, optionally about 150:1. In some embodiments, a weight ratio of protease inhibitor to therapeutically active agent is in a range of from 200:1 to 300:1, optionally about 250:1. In some embodiments, a weight ratio of protease inhibitor to therapeutically active agent is in a range of from 300:1 to 400:1, optionally about 350:1. In some embodiments, a weight ratio of protease inhibitor to therapeutically active agent is in a range of from 400:1 to 500:1, optionally about 450:1. In some embodiments, the protease inhibitor is soybean trypsin inhibitor.

In some embodiments of any one of the embodiments described herein, a weight ratio of SNAC to therapeutically active agent in a composition described herein or in a core of a unit dosage form described herein is in a range of from 10:1 to 20:1 (SNAC: therapeutically active agent). In some embodiments, the ratio is about 15:1. In some embodiments, the composition or core further comprises a protease inhibitor. In some of the aforementioned embodiments wherein the composition comprises a protease inhibitor, a weight ratio of protease inhibitor to therapeutically active agent is in a range of from 1:1 to 5:1 (protease inhibitor: therapeutically active agent), optionally about 3:1. In some embodiments, a weight ratio of protease inhibitor to therapeutically active agent is in a range of from 5:1 to 10:1, optionally about 7.5:1. In some embodiments, a weight ratio of protease inhibitor to therapeutically active agent is in a range of from 10:1 to 20:1, optionally about 15:1. In some embodiments, a weight ratio of protease inhibitor to therapeutically active agent is in a range of from 20:1 to 30:1, optionally about 25:1.

In some embodiments, a weight ratio of protease inhibitor to therapeutically active agent is in a range of from 30:1 to 40:1, optionally about 35:1. In some embodiments, a weight ratio of protease inhibitor to therapeutically active agent is in a range of from 40:1 to 50:1, optionally about 45:1. In some embodiments, a weight ratio of protease inhibitor to therapeutically active agent is in a range of from 50:1 to 75:1, optionally about 62.5:1. In some embodiments, a weight ratio of protease inhibitor to therapeutically active agent is in a range of from 75:1 to 100:1, optionally about 87.5:1. In some embodiments, a weight ratio of protease inhibitor to therapeutically active agent is in a range of from 100:1 to 200:1, optionally about 150:1. In some embodiments, a weight ratio of protease inhibitor to therapeutically active agent is in a range of from 200:1 to 300:1, optionally about 250:1. In some embodiments, a weight ratio of protease inhibitor to therapeutically active agent is in a range of from 300:1 to 400:1, optionally about 350:1. In some embodiments, a weight ratio of protease inhibitor to therapeutically active agent is in a range of from 400:1 to 500:1, optionally about 450:1. In some embodiments, the protease inhibitor is soybean trypsin inhibitor.

In some embodiments of any one of the embodiments described herein, a weight ratio of SNAC to therapeutically active agent in a composition described herein or in a core of a unit dosage form described herein is in a range of from 20:1 to 30:1 (SNAC: therapeutically active agent). In some embodiments, the ratio is about 25:1. In some embodiments, the composition or core further comprises a protease inhibitor. In some of the aforementioned embodiments wherein the composition comprises a protease inhibitor, a weight ratio of protease inhibitor to therapeutically active agent is in a range of from 1:1 to 5:1 (protease inhibitor: therapeutically active agent), optionally about 3:1. In some embodiments, a weight ratio of protease inhibitor to therapeutically active agent is in a range of from 5:1 to 10:1, optionally about 7.5:1. In some embodiments, a weight ratio of protease inhibitor to therapeutically active agent is in a range of from 10:1 to 20:1, optionally about 15:1. In some embodiments, a weight ratio of protease inhibitor to therapeutically active agent is in a range of from 20:1 to 30:1, optionally about 25:1. In some embodiments, a weight ratio of protease inhibitor to therapeutically active agent is in a range of from 30:1 to 40:1, optionally about 35:1. In some embodiments, a weight ratio of protease inhibitor to therapeutically active agent is in a range of from 40:1 to 50:1, optionally about 45:1. In some embodiments, a weight ratio of protease inhibitor to therapeutically active agent is in a range of from 50:1 to 75:1, optionally about 62.5:1. In some embodiments,
a weight ratio of protease inhibitor to therapeutically active agent is in a range of from 75:1 to 100:1, optionally about 87.5:1. In some embodiments, a weight ratio of protease inhibitor to therapeutically active agent is in a range of from 100:1 to 200:1, optionally about 150:1. In some embodiments, a weight ratio of protease inhibitor to therapeutically active agent is in a range of from 200:1 to 300:1, optionally about 250:1. In some embodiments, a weight ratio of protease inhibitor to therapeutically active agent is in a range of from 300:1 to 400:1, optionally about 350:1. In some embodiments, a weight ratio of protease inhibitor to therapeutically active agent is in a range of from 400:1 to 500:1, optionally about 450:1. In some embodiments, the protease inhibitor is soybean trypsin inhibitor.

In some embodiments of any one of the embodiments described herein, a weight ratio of SNAC to therapeutically active agent in a composition described herein or in a core of a unit dosage form described herein is in a range of from 30:1 to 50:1 (SNAC: therapeutically active agent). In some embodiments, the ratio is about 40:1. In some embodiments, the composition or core further comprises a protease inhibitor. In some of the aforementioned embodiments wherein the composition comprises a protease inhibitor, a weight ratio of protease inhibitor to therapeutically active agent is in a range of from 1:1 to 5:1 (protease inhibitor: therapeutically active agent), optionally about 3:1. In some embodiments, a weight ratio of protease inhibitor to therapeutically active agent is in a range of from 5:1 to 10:1, optionally about 7.5:1. In some embodiments, a weight ratio of protease inhibitor to therapeutically active agent is in a range of from 10:1 to 20:1, optionally about 15:1. In some embodiments, a weight ratio of protease inhibitor to therapeutically active agent is in a range of from 20:1 to 30:1, optionally about 25:1. In some embodiments, a weight ratio of protease inhibitor to therapeutically active agent is in a range of from 30:1 to 40:1, optionally about 35:1. In some embodiments, a weight ratio of protease inhibitor to therapeutically active agent is in a range of from 40:1 to 50:1, optionally about 45:1. In some embodiments, a weight ratio of protease inhibitor to therapeutically active agent is in a range of from 50:1 to 75:1, optionally about 62.5:1. In some embodiments, a weight ratio of protease inhibitor to therapeutically active agent is in a range of from 75:1 to 100:1, optionally about 87.5:1. In some embodiments, a weight ratio of protease inhibitor to therapeutically active agent is in a range of from 100:1 to 200:1, optionally about 150:1. In some embodiments, a weight ratio of protease inhibitor to therapeutically active agent is in a range of from 200:1 to 300:1, optionally about 250:1. In some embodiments, a weight ratio of protease inhibitor to therapeutically active agent is in a range of from 300:1 to 400:1, optionally about 350:1. In some embodiments, a weight ratio of protease inhibitor to therapeutically active agent is in a range of from 400:1 to 500:1, optionally about 450:1. In some embodiments, the protease inhibitor is soybean trypsin inhibitor.

In some embodiments of any one of the embodiments described herein, a weight ratio of SNAC to therapeutically active agent in a composition described herein or in a core of a unit dosage form described herein is in a range of from 50:1 to 100:1 (SNAC: therapeutically active agent). In some embodiments, the ratio is about 75:1. In some embodiments, the composition or core further comprises a protease inhibitor. In some of the aforementioned embodiments wherein the composition comprises a protease inhibitor, a weight ratio of protease inhibitor to therapeutically active agent is in a range of from 1:1 to 5:1 (protease inhibitor: therapeutically active agent), optionally about 3:1. In some embodiments, a weight ratio of protease inhibitor to therapeutically active agent is in a range of from 5:1 to 10:1, optionally about 7.5:1. In some embodiments, a weight ratio of protease inhibitor to therapeutically active agent is in a range of from 10:1 to 20:1, optionally about 15:1. In some embodiments, a weight ratio of protease inhibitor to therapeutically active agent is in a range of from 20:1 to 30:1, optionally about 25:1. In some embodiments, a weight ratio of protease inhibitor to therapeutically active agent is in a range of from 30:1 to 40:1, optionally about 35:1. In some embodiments, a weight ratio of protease inhibitor to therapeutically active agent is in a range of from 40:1 to 50:1, optionally about 45:1. In some embodiments, a weight ratio of protease inhibitor to therapeutically active agent is in a range of from 50:1 to 75:1, optionally about 62.5:1. In some embodiments, a weight ratio of protease inhibitor to therapeutically active agent is in a range of from 75:1 to 100:1, optionally about 87.5:1. In some embodiments, a weight ratio of protease inhibitor to therapeutically active agent is in a range of from 100:1 to 200:1, optionally about 150:1. In some embodiments, a weight ratio of protease inhibitor to therapeutically active agent is in a range of from 200:1 to 300:1, optionally about 250:1. In some embodiments, a weight ratio of protease inhibitor to therapeutically active agent is in a range of from 300:1 to 400:1, optionally about 350:1. In some embodiments, a weight ratio of protease inhibitor to therapeutically active agent is in a range of from 400:1 to 500:1, optionally about 450:1. In some embodiments, the protease inhibitor is soybean trypsin inhibitor.

In some embodiments of any one of the embodiments described herein, a weight ratio of SNAC to therapeutically active agent in a composition described herein or in a core of a unit dosage form described herein is in a range of from 100:1 to 200:1 (SNAC: therapeutically active agent). In some embodiments, the ratio is about 150:1. In some embodiments, the composition or core further comprises a protease inhibitor. In some of the aforementioned embodiments wherein the composition comprises a protease inhibitor, a weight ratio of protease inhibitor to therapeutically active agent is in a range of from 1:1 to 5:1 (protease inhibitor: therapeutically active agent), optionally about 3:1. In some embodiments, a weight ratio of protease inhibitor to therapeutically active agent is in a range of from 5:1 to 10:1, optionally about 7.5:1. In some embodiments, a weight ratio of protease inhibitor to therapeutically active agent is in a range of from 10:1 to 20:1, optionally about 15:1. In some embodiments, a weight ratio of protease inhibitor to therapeutically active agent is in a range of from 20:1 to 30:1, optionally about 25:1. In some embodiments, a weight ratio of protease inhibitor to therapeutically active agent is in a range of from 30:1 to 40:1, optionally about 35:1. In some embodiments, a weight ratio of protease inhibitor to therapeutically active agent is in a range of from 40:1 to 50:1, optionally about 45:1. In some embodiments, a weight ratio of protease inhibitor to therapeutically active agent is in a range of from 50:1 to 75:1, optionally about 62.5:1. In some embodiments, a weight ratio of protease inhibitor to therapeutically active agent is in a range of from 75:1 to 100:1, optionally about 87.5:1. In some embodiments, a weight ratio of protease inhibitor to therapeutically active agent is in a range of from 100:1 to 200:1, optionally about 150:1. In some embodiments, a weight ratio of protease inhibitor to therapeutically active agent is in a range of from 200:1 to 300:1, optionally about 250:1. In some embodiments, a weight ratio of protease inhibitor to therapeutically active agent is in a range of from 300:1 to 400:1, optionally about 350:1. In some embodiments, a weight ratio of protease inhibitor to therapeutically active agent is in a range of from 400:1 to 500:1, optionally about 450:1. In some embodiments, the protease inhibitor is soybean trypsin inhibitor.

In some embodiments of any one of the embodiments described herein, a weight ratio of SNAC to therapeutically active agent in a composition described herein or in a core of a unit dosage form described herein is in a range of from 200:1 to 300:1 (SNAC: therapeutically active agent). In some embodiments, the ratio is about 250:1. In some embodiments, the composition or core further comprises a protease inhibitor. In some of the aforementioned embodiments wherein the composition comprises a protease inhibitor, a weight ratio of protease inhibitor to therapeutically active agent is in a range of from 1:1 to 5:1 (protease inhibitor: therapeutically active agent), optionally about 3:1. In some embodiments, a weight ratio of protease inhibitor to therapeutically active agent is in a range of from 5:1 to 10:1, optionally about 7.5:1. In some embodiments, a weight ratio of protease inhibitor to therapeutically active agent is in a range of from 10:1 to 20:1, optionally about 15:1. In some embodiments, a weight ratio of protease inhibitor to therapeutically active agent is in a range of from 20:1 to 30:1, optionally about 25:1. In some embodiments, a weight ratio of protease inhibitor to therapeutically active agent is in a range of from 30:1 to 40:1, optionally about 35:1. In some embodiments, a weight ratio of protease inhibitor to therapeutically active agent is in a range of from 40:1 to 50:1, optionally about 45:1. In some embodiments, a weight ratio of protease inhibitor to therapeutically active agent is in a range of from 50:1 to 75:1, optionally about 62.5:1. In some embodiments, a weight ratio of protease inhibitor to therapeutically active agent is in a range of from 75:1 to 100:1, optionally about 87.5:1. In some embodiments, a weight ratio of protease inhibitor to therapeutically active agent is in a range of from 100:1 to 200:1, optionally about 150:1. In some embodiments, a weight ratio of protease inhibitor to therapeutically active agent is in a range of from 200:1 to 300:1, optionally about 250:1. In some embodiments, a weight ratio of protease inhibitor to therapeutically active agent is in a range of from 300:1 to 400:1, optionally about 350:1. In some embodiments, a weight ratio of protease inhibitor to therapeutically active agent is in a range of from 400:1 to 500:1, optionally about 450:1. In some embodiments, the protease inhibitor is soybean trypsin inhibitor.

In some embodiments of any one of the embodiments described herein, a weight ratio of SNAC to therapeutically active agent in a composition described herein or in a core of a unit dosage form described herein is in a range of from 300:1 to 500:1 (SNAC: therapeutically active agent). In some embodiments, the ratio is about 400:1. In some embodiments, the composition or core further comprises a protease inhibitor. In some of the aforementioned embodiments wherein the composition comprises a protease inhibitor, a weight ratio of protease inhibitor to therapeutically active agent is in a range of from 1:1 to 5:1 (protease inhibitor: therapeutically active agent), optionally about 3:1. In some embodiments, a weight ratio of protease inhibitor to therapeutically active agent is in a range of from 5:1 to 10:1, optionally about 7.5:1. In some embodiments, a weight ratio of protease inhibitor to therapeutically active agent is in a range of from 10:1 to 20:1, optionally about 15:1. In some embodiments, a weight ratio of protease inhibitor to therapeutically active agent is in a range of from 20:1 to 30:1, optionally about 25:1. In some embodiments, a weight ratio of protease inhibitor to therapeutically active agent is in a range of from 30:1 to 40:1, optionally about 35:1. In some embodiments, a weight ratio of protease inhibitor to therapeutically active agent is in a range of from 40:1 to 50:1, optionally about 45:1. In some embodiments, a weight ratio of protease inhibitor to therapeutically active agent is in a range of from 50:1 to 75:1, optionally about 62.5:1. In some embodiments, a weight ratio of protease inhibitor to therapeutically active agent is in a range of from 75:1 to 100:1, optionally about 87.5:1. In some embodiments, a weight ratio of protease inhibitor to therapeutically active agent is in a range of from 100:1 to 200:1, optionally about 150:1. In some embodiments, a weight ratio of protease inhibitor to therapeutically active agent is in a range of from 200:1 to 300:1, optionally about 250:1. In some embodiments, a weight ratio of protease inhibitor to therapeutically active agent is in a range of from 300:1 to 400:1, optionally about 350:1. In some embodiments, a weight ratio of protease inhibitor to therapeutically active agent is in a range of from 400:1 to 500:1, optionally about 450:1. In some embodiments, the protease inhibitor is soybean trypsin inhibitor.

In some embodiments of any one of the embodiments described herein, a weight ratio of SNAC to therapeutically active agent in a composition described herein or in a core of a unit dosage form described herein is in a range of from 500:1 to 1000:1 (SNAC: therapeutically active agent). In some embodiments, the ratio is about 750:1. In some embodiments, the composition or core further comprises a protease inhibitor. In some of the aforementioned embodiments wherein the composition comprises a protease inhibitor, a weight ratio of protease inhibitor to therapeutically active agent is in a range of from 1:1 to 5:1 (protease inhibitor: therapeutically active agent), optionally about 3:1. In some embodiments, a weight ratio of protease inhibitor to therapeutically active agent is in a range of from 5:1 to 10:1, optionally about 7.5:1. In some embodiments, a weight ratio of protease inhibitor to therapeutically active agent is in a range of from 10:1 to 20:1, optionally about 15:1. In some embodiments, a weight ratio of protease inhibitor to therapeutically active agent is in a range of from 20:1 to 30:1, optionally about 25:1. In some embodiments, a weight ratio of protease inhibitor to therapeutically active agent is in a range of from 30:1 to 40:1, optionally about 35:1. In some embodiments, a weight ratio of protease inhibitor to therapeutically active agent is in a range of from 40:1 to 50:1, optionally about 45:1. In some embodiments, a weight ratio of protease inhibitor to therapeutically active agent is in a range of from 50:1 to 75:1, optionally about 62.5:1. In some embodiments, a weight ratio of protease inhibitor to therapeutically active agent is in a range of from 75:1 to 100:1, optionally about 87.5:1. In some embodiments, a weight ratio of protease inhibitor to therapeutically active agent is in a range of from 100:1 to 200:1, optionally about 150:1. In some embodiments, a weight ratio of protease inhibitor to therapeutically active agent is in a range of from 200:1 to 300:1, optionally about 250:1. In some embodiments, a weight ratio of protease inhibitor to therapeutically active agent is in a range of from 300:1 to 400:1, optionally about 350:1. In some embodiments, a weight ratio of protease inhibitor to therapeutically active agent is in a range of from 400:1 to 500:1, optionally about 450:1. In some embodiments, the protease inhibitor is soybean trypsin inhibitor.

In some embodiments of any one of the embodiments described herein relating to a unit dosage form, the amount of SNAC in a unit dosage form described herein is at least about 0.1 mg. In some embodiments, the amount of SNAC in a unit dosage form described herein is at least about 0.2 mg. In some embodiments, the amount of SNAC in a unit dosage form described herein is at least about 0.3 mg. In some embodiments, the amount of SNAC in a unit dosage form described herein is at least about 0.4 mg. In some embodiments, the amount of SNAC in a unit dosage form described herein is at least about 0.6 mg. In some embodiments, the amount of SNAC in a unit dosage form described herein is at least about 0.8 mg. In some embodiments, the amount of SNAC in a unit dosage form described herein is at least about 1 mg. In some embodiments, the amount of SNAC in a unit dosage form described herein is at least about 1.5 mg. In some embodiments, the amount of SNAC in a unit dosage form described herein is at least about 2 mg. In some embodiments, the amount of SNAC in a unit dosage form described herein is at least about 2.5 mg. In some embodiments, the amount of SNAC in a unit dosage form described herein is at least about 3 mg. In some embodiments, the amount of SNAC in a unit dosage form described herein is at least about 5 mg. In some embodiments, the amount of SNAC in a unit dosage form described herein is at least about 7 mg. In some embodiments, the amount of SNAC in a unit dosage form described herein is at least about 10 mg. In some embodiments, the amount of SNAC in a unit dosage form described herein is at least about 12 mg. In some embodiments, the amount of SNAC in a unit dosage form described herein is at least about 15 mg. In some embodiments, the amount of SNAC in a unit dosage form described herein is at least about 20 mg. In some embodiments, the amount of SNAC in a unit dosage form described herein is at least about 30 mg. In some embodiments, the amount of SNAC in a unit dosage form described herein is at least about 50 mg. In some embodiments, the amount of SNAC in a unit dosage form described herein is at least about 70 mg. In some embodiments, the amount of SNAC in a unit dosage form described herein is at least about 100 mg.

In some embodiments of any one of the embodiments described herein relating to a unit dosage form, the amount of SNAC in a unit dosage form described herein is in a range of from 0.1 to 1 mg. In some embodiments, the amount of SNAC in a unit dosage form described herein is in a range of from 0.2 to 1 mg. In some embodiments, the amount of SNAC in a unit dosage form described herein is in a range of from 0.3 to 1 mg. In some embodiments, the amount of SNAC in a unit dosage form described herein is in a range of from 0.5 to 1 mg.

In some embodiments of any one of the embodiments described herein relating to a unit dosage form, the amount of SNAC in a unit dosage form described herein is in a range of from 0.1 to 2 mg. In some embodiments, the amount of SNAC in a unit dosage form described herein is in a range of from 0.2 to 2 mg. In some embodiments, the amount of SNAC in a unit dosage form described herein is in a range of from 0.3 to 2 mg. In some embodiments, the amount of SNAC in a unit dosage form described herein is in a range of from 0.5 to 2 mg. In some embodiments, the amount of SNAC in a unit dosage form described herein is in a range of from 1 to 2 mg.

In some embodiments of any one of the embodiments described herein relating to a unit dosage form, the amount of SNAC in a unit dosage form described herein is in a range of from 1 to 10 mg. In some embodiments, the amount of SNAC in a unit dosage form described herein is in a range of from 2 to 10 mg. In some embodiments, the amount of SNAC in a unit dosage form described herein is in a range of from 3 to 10 mg. In some embodiments, the amount of SNAC in a unit dosage form described herein is in a range of from 5 to 10 mg.

In some embodiments of any one of the embodiments described herein relating to a unit dosage form, the amount of SNAC in a unit dosage form described herein is in a range of from 1 to 20 mg. In some embodiments, the amount of SNAC in a unit dosage form described herein is in a range of from 2 to 20 mg. In some embodiments, the amount of SNAC in a unit dosage form described herein is in a range of from 3 to 20 mg. In some embodiments, the amount of SNAC in a unit dosage form described herein is in a range of from 5 to 20 mg. In some embodiments, the amount of SNAC in a unit dosage form described herein is in a range of from 10 to 20 mg.

In some embodiments of any one of the embodiments described herein relating to a unit dosage form, the amount of SNAC in a unit dosage form described herein is in a range of from 10 to 100 mg. In some embodiments, the amount of SNAC in a unit dosage form described herein is in a range of from 20 to 100 mg. In some embodiments, the amount of SNAC in a unit dosage form described herein is in a range of from 30 to 100 mg. In some embodiments, the amount of SNAC in a unit dosage form described herein is in a range of from 50 to 100 mg.

In some embodiments of any one of the embodiments described herein relating to a unit dosage form, the amount of SNAC in a unit dosage form described herein is in a range of from 10 to 200 mg. In some embodiments, the amount of SNAC in a unit dosage form described herein is in a range of from 20 to 200 mg. In some embodiments, the amount of SNAC in a unit dosage form described herein is in a range of from 30 to 200 mg. In some embodiments, the amount of SNAC in a unit dosage form described herein is in a range of from 50 to 200 mg. In some embodiments, the amount of SNAC in a unit dosage form described herein is in a range of from 100 to 200 mg.

In some embodiments of any one of the embodiments described herein relating to a unit dosage form, the amount of SNAC in a unit dosage form described herein is in a range of from 10 to 500 mg. In some embodiments, the amount of SNAC in a unit dosage form described herein is in a range of from 20 to 500 mg. In some embodiments, the amount of SNAC in a unit dosage form described herein is in a range of from 30 to 500 mg. In some embodiments, the amount of SNAC in a unit dosage form described herein is in a range of from 50 to 500 mg. In some embodiments, the amount of SNAC in a unit dosage form described herein is in a range of from 100 to 500 mg. In some embodiments, the amount of SNAC in a unit dosage form described herein is in a range of from 200 to 500 mg.

In some embodiments of any one of the embodiments described herein relating to a unit dosage form, the amount of SNAC in a unit dosage form described herein is in a range of from 10 to 1000 mg. In some embodiments, the amount of SNAC in a unit dosage form described herein is in a range of from 20 to 1000 mg. In some embodiments, the amount of SNAC in a unit dosage form described herein is in a range of from 30 to 1000 mg. In some embodiments, the amount of SNAC in a unit dosage form described herein is in a range of from 50 to 1000 mg. In some embodiments, the amount of SNAC in a unit dosage form described herein is in a range of from 100 to 1000 mg. In some embodiments, the amount of SNAC in a unit dosage form described herein is in a range of from 200 to 1000 mg. In some embodiments, the amount of SNAC in a unit dosage form described herein is in a range of from 500 to 1000 mg.

In some embodiments of any one of the embodiments described herein relating to a unit dosage form, the amount of SNAC in a unit dosage form described herein is in a range of from 10 to 1000 mg. In some embodiments, the amount of SNAC in a unit dosage form described herein is in a range of from 20 to 1000 mg. In some embodiments, the amount of SNAC in a unit dosage form described herein is in a range of from 30 to 1000 mg. In some embodiments, the amount of SNAC in a unit dosage form described herein is in a range of from 50 to 1000 mg. In some embodiments, the amount of SNAC in a unit dosage form described herein is in a range of from 100 to 1000 mg. In some embodiments, the amount of SNAC in a unit dosage form described herein is in a range of from 200 to 1000 mg. In some embodiments, the amount of SNAC in a unit dosage form described herein is in a range of from 500 to 1000 mg.

In some embodiments of any one of the embodiments described herein relating to a unit dosage form, the amount of SNAC in a unit dosage form described herein is in a range of from 10 to 2000 mg. In some embodiments, the amount of SNAC in a unit dosage form described herein is in a range of from 20 to 2000 mg. In some embodiments, the amount of SNAC in a unit dosage form described herein is in a range of from 30 to 2000 mg. In some embodiments, the amount of SNAC in a unit dosage form described herein is in a range of from 50 to 2000 mg. In some embodiments, the amount of SNAC in a unit dosage form described herein is in a range of from 100 to 2000 mg. In some embodiments, the amount of SNAC in a unit dosage form described herein is in a range of from 200 to 2000 mg. In some embodiments, the amount of SNAC in a unit dosage form described herein is in a range of from 500 to 2000 mg. In some embodiments, the amount of SNAC in a unit dosage form described herein is in a range of from 1000 to 2000 mg.

In some embodiments of any one of the embodiments described herein relating to an amount of SNAC in a unit dosage form, the amount of therapeutically active agent is in accordance with any one of the ratios of SNAC to therapeutically active agent described herein. In some embodiments, the unit dosage form further comprises at least one protease inhibitor in an amount which is in accordance with any one of the ratios of protease inhibitor to therapeutically active agent described herein.

Therapeutically Active Agent:

In some embodiments of any one of the embodiments described herein, the unit dosage form according to any one of the aspects described herein comprises at least 50 µg of therapeutically active agent. In some embodiments, the unit dosage form comprises at least 100 µg of therapeutically active agent. In some embodiments, the unit dosage form comprises at least 200 µg of therapeutically active agent. In some embodiments, the unit dosage form comprises at least 500 µg of therapeutically active agent. In some embodiments, the amount of SNAC is in accordance with any one of the ratios of SNAC to therapeutically active agent described herein. In some embodiments, the unit dosage form further comprises at least one protease inhibitor in an amount which is in accordance with any one of the ratios of protease inhibitor to therapeutically active agent described herein.

In some embodiments of any one of the embodiments described herein, the unit dosage form according to any one of the aspects described herein comprises 2000 µg or less of therapeutically active agent. In some embodiments, the unit dosage form comprises 1000 µg or less of therapeutically active agent. In some embodiments, the amount of SNAC is in accordance with any one of the ratios of SNAC to therapeutically active agent described herein. In some embodiments, the unit dosage form further comprises at least one protease inhibitor in an amount which is in accordance with any one of the ratios of protease inhibitor to therapeutically active agent described herein.

In some embodiments of any one of the embodiments described herein, the unit dosage form comprises from 200 to 2000 µg of therapeutically active agent. In some embodiments, the unit dosage form comprises from 500 to 1000 µg of therapeutically active agent. In some embodiments, the unit dosage form comprises about 750 µg of therapeutically active agent. In some embodiments, the therapeutically active agent is a parathyroid hormone or a fragment thereof. In some embodiments, the therapeutically active agent is teriparatide. In some embodiments, the amount of SNAC is in accordance with any one of the ratios of SNAC to therapeutically active agent described herein. In some embodiments, the unit dosage form further comprises at least one protease inhibitor in an amount which is in accordance with any one of the ratios of protease inhibitor to therapeutically active agent described herein.

Compositions described herein are particularly suitable for enhancing the absorption of therapeutically active agents whose absorption upon oral administration is limited, for example, by a large molecular weight, strong hydrophilicity (e.g., which inhibits crossing of lipid membranes in the gastrointestinal tract), strong lipophilicity (e.g., which reduces diffusion in the gastrointestinal tract, inhibits permeation of hydrophilic layers such as intestinal mucus linings and/or results in accumulation in lipid membranes), and/or degradation in the gastrointestinal tract (e.g., by proteolysis).

In some embodiments of any one of the embodiments described herein, the therapeutically active agent included in any of the compositions (including composition unit dosage forms) described herein has a molecular weight of at least 0.5 kDa. In some embodiments, the molecular weight is in a range of from 0.5 to 150 kDa. In some embodiments, the molecular weight is in a range of from 0.5 to 100 kDa. In some embodiments, the molecular weight is in a range of from 0.5 to 75 kDa. In some embodiments, the molecular weight is in a range of from 0.5 to 50 kDa. In some embodiments, the molecular weight is in a range of from 0.5 to 30 kDa. In some embodiments, the molecular weight is in a range of from 0.5 to 20 kDa. In some embodiments, the molecular weight is in a range of from 0.5 to 10 kDa. In some embodiments, the molecular weight is in a range of from 0.5 to 7.5 kDa. In some embodiments, the molecular weight is in a range of from 0.5 to 5 kDa.

In some embodiments of any one of the embodiments described herein, the therapeutically active agent has a molecular weight of at least 1 kDa. In some embodiments, the molecular weight is in a range of from 1 to 150 kDa. In some embodiments, the molecular weight is in a range of from 1 to 100 kDa. In some embodiments, the molecular weight is in a range of from 1 to 75 kDa. In some embodiments, the molecular weight is in a range of from 1 to 50 kDa. In some embodiments, the molecular weight is in a range of from 1 to 30 kDa. In some embodiments, the molecular weight is in a range of from 1 to 20 kDa. In some embodiments, the molecular weight is in a range of from 1 to 10 kDa. In some embodiments, the molecular weight is in a range of from 1 to 7.5 kDa. In some embodiments, the molecular weight is in a range of from 1 to 5 kDa.

In some embodiments of any one of the embodiments described herein, the therapeutically active agent has a molecular weight of at least 2 kDa. In some embodiments, the molecular weight is in a range of from 2 to 150 kDa. In some embodiments, the molecular weight is in a range of from 2 to 100 kDa. In some embodiments, the molecular weight is in a range of from 2 to 75 kDa. In some embodiments, the molecular weight is in a range of from 2 to 50 kDa. In some embodiments, the molecular weight is in a range of from 2 to 30 kDa. In some embodiments, the molecular weight is in a range of from 2 to 20 kDa. In some embodiments, the molecular weight is in a range of from 2 to 10 kDa. In some embodiments, the molecular weight is in a range of from 2 to 7.5 kDa. In some embodiments, the molecular weight is in a range of from 2 to 5 kDa.

In some embodiments of any one of the embodiments described herein, the therapeutically active agent has a molecular weight of at least 3 kDa. In some embodiments, the molecular weight is in a range of from 3 to 150 kDa. In some embodiments, the molecular weight is in a range of from 3 to 100 kDa. In some embodiments, the molecular weight is in a range of from 3 to 75 kDa. In some embodiments, the molecular weight is in a range of from 3 to 50 kDa. In some embodiments, the molecular weight is in a range of from 3 to 30 kDa. In some embodiments, the molecular weight is in a range of from 3 to 20 kDa. In some embodiments, the molecular weight is in a range of from 3 to 10 kDa. In some embodiments, the molecular weight is in a range of from 3 to 7.5 kDa. In some embodiments, the molecular weight is in a range of from 3 to 5 kDa.

In some embodiments of any one of the embodiments described herein, the therapeutically active agent has a molecular weight of at least 4 kDa. In some embodiments, the molecular weight is in a range of from 4 to 150 kDa. In some embodiments, the molecular weight is in a range of from 4 to 100 kDa. In some embodiments, the molecular weight is in a range of from 4 to 75 kDa. In some embodiments, the molecular weight is in a range of from 4 to 50 kDa. In some embodiments, the molecular weight is in a range of from 4 to 30 kDa. In some embodiments, the molecular weight is in a range of from 4 to 20 kDa. In some embodiments, the molecular weight is in a range of from 4 to 10 kDa. In some embodiments, the molecular weight is in a range of from 4 to 7.5 kDa. In some embodiments, the molecular weight is in a range of from 4 to 5 kDa.

In some embodiments of any one of the embodiments described herein, the therapeutically active agent has a molecular weight of at least 5 kDa. In some embodiments, the molecular weight is in a range of from 5 to 150 kDa. In some embodiments, the molecular weight is in a range of from 5 to 100 kDa. In some embodiments, the molecular weight is in a range of from 5 to 75 kDa. In some embodiments, the molecular weight is in a range of from 5 to 50 kDa. In some embodiments, the molecular weight is in a range of from 5 to 30 kDa. In some embodiments, the molecular weight is in a range of from 5 to 20 kDa. In some embodiments, the molecular weight is in a range of from 5 to 10 kDa. In some embodiments, the molecular weight is in a range of from 5 to 7.5 kDa.

In some embodiments of any one of the embodiments described herein, the therapeutically active agent has a molecular weight of at least 10 kDa. In some embodiments, the molecular weight is in a range of from 10 to 150 kDa. In some embodiments, the molecular weight is in a range of from 10 to 100 kDa. In some embodiments, the molecular weight is in a range of from 10 to 75 kDa. In some embodiments, the molecular weight is in a range of from 10 to 50 kDa. In some embodiments, the molecular weight is in a range of from 10 to 30 kDa. In some embodiments, the molecular weight is in a range of from 10 to 20 kDa.

In some embodiments of any one of the embodiments described herein, the therapeutically active agent has a molecular weight of at least 20 kDa. In some embodiments, the molecular weight is in a range of from 20 to 150 kDa. In some embodiments, the molecular weight is in a range of from 20 to 100 kDa. In some embodiments, the molecular weight is in a range of from 20 to 75 kDa. In some embodiments, the molecular weight is in a range of from 20 to 50 kDa. In some embodiments, the molecular weight is in a range of from 20 to 30 kDa.

In some embodiments of any one of the embodiments described herein, the therapeutically active agent has a molecular weight of at least 50 kDa. In some embodiments, the molecular weight is in a range of from 50 to 150 kDa. In some embodiments, the molecular weight is in a range of from 50 to 100 kDa. In some embodiments, the molecular weight is in a range of from 50 to 75 kDa.

Without being bound by any particular theory, it is believed that agents having a relatively high molecular weight (e.g., at least 0.5 kDa, at least 1 kDa, at least 2 kDa, at least 3 kDa, at least 4 kDa) tend to be less efficiently absorbed upon oral administration than relatively small molecules (e.g., molecules having a molecular weight of less than 0.5 kDa, or less than 1 kDa) and therefore, their absorption is particularly susceptible to enhancement by SNAC activity.

In some embodiments of any one of the embodiments described herein, the therapeutically active agent included in any of the compositions (including composition unit dosage forms) described herein is a hormone and/or cytokine (e.g., a hormone). In some embodiments, the polypeptide is a polypeptide hormone and/or cytokine, or a fragment thereof (e.g., a fragment exhibiting an activity of the hormone and/or cytokine), or a homolog of a polypeptide hormone and/or cytokine or fragment thereof.

Examples of polypeptides which may be utilized (per se or as fragments thereof and/or homologs thereof) as therapeutically active agents according to embodiments of the invention include, without limitation, insulin, a glucagon, a parathyroid hormone, an interferon, a growth hormone, an erythropoietin, a calcitonin, an omentin, a motilin, a leptin, a peptide YY, a GLP-1 (glucagon-like peptide-1), a GLP-2 (glucagon-like peptide-2), granulocyte-colony stimulating factor (G-CSF), an antibody (e.g., monoclonal antibody), an interleukin, an erythropoietin, a vasopressin, a vasoactive intestinal peptide, a pituitary adenylate cyclase-activating peptide (PACAP), a blood clotting factor, an endomorphin (e.g., endomorphin-1, endomorphin-2), a TNF inhibitor (e.g., infliximab, adalimumab, certolizumab, golimumab, etanercept), disitertide, octreotide (a somatotropin analog), davunetide, icatibant, glucocerebrosidase, a gonadotropin releasing hormone (GnRH), acyline (a GnRH antagonist), and a GLP-1 agonist such as exendin-4 (including exenatide and lixisenatide). Examples of growth hormones, include, without limitation, somatotropin (growth hormone 1), growth hormone 2, and growth factors (e.g., insulin-like growth factor 1 (IGF-1), fibroblast growth factor (FGF), ciliary neurotrophic factor).

Insulin, glucagon, parathyroid hormone, erythropoietin, calcitonin, motilin, leptin, peptide YY, GLP-1 (including derivatives thereof such as liraglutide, taspoglutide, albiglutide and dulaglutide), GLP-2, GnRH (including derivatives thereof such as leuprorelin, buserelin, histrelin, goserelin, deslorelin, nafarelin and triptorelin), vasopres sin (including derivatives thereof such as desmopres sin), vasoactive intestinal peptide (including aviptadil), pituitary adenylate cyclase-activating peptide (PACAP), growth hormones (including axokine, a homolog of a fragment of ciliary neurotrophic factor) and G-CSF are non-limiting examples of polypeptide hormones.

Interferons, interleukins, erythropoietin and analogs thereof (e.g., darbepoetin), omentin and G-CSF are non-limiting examples of polypeptide cytokines.

In some embodiments of any one of the embodiments described herein, the therapeutically active agent is parathyroid hormone (PTH) or a fragment thereof (e.g., a fragment exhibiting an activity of PTH). In some embodiments, the polypeptide is teriparatide (i.e., a PTH fragment having amino acid residues 1-34 of PTH).

Herein, the term "parathyroid hormone" or its abbreviation "PTH" encompasses parathyroid hormone (having a naturally occurring amino acid sequence, e.g., in humans) and homologs of the parathyroid hormone. A "fragment" of parathyroid hormone encompasses fragments of parathyroid hormone having a naturally occurring amino acid sequence (e.g., in humans) and homologs of such fragments.

Without being bound by any particular theory, it is believed that agents which are polypeptides tend to be poorly absorbed upon oral administration, for example, due to their polarity and/or relatively large molecular weight; and therefore, their absorption is particularly susceptible to enhancement by SNAC activity.

In some embodiments of any one of the embodiments described herein wherein the therapeutically active agents is a polypeptide, the composition further comprises at least one protease inhibitor, for example, according to any one of the embodiments described herein relating to a protease inhibitor.

It has been reported that therapeutically active agents which exhibit more than one of the following criteria tend to be poorly absorbed upon oral administration (when administered alone), a phenomenon referred to in the art as "Lipinski's rule of 5":

(i) a total number of nitrogen-hydrogen bonds and oxygen hydrogen bonds (which are typically hydrogen bond donors) which is more than 5;

(ii) a total number of nitrogen and oxygen atoms (which are typically hydrogen bond acceptors) which is more than 5;

(iii) an octanol-water partition coefficient (log P) which is greater than 5; and/or (iv) a molecular weight of at least 500 Da (0.5 kDa).

The abovementioned criteria (i) and (ii) are associated with hydrogen bonding and hydrophilicity; whereas criteria (iii) is associated with lipophilicity.

As described herein, therapeutically active agents poorly absorbed upon oral administration when administered alone are particularly suitable for being included in compositions described herein, in order to enhance their absorption.

In some embodiments of any one of the embodiments described herein, the therapeutically active agent meets at least one of the abovementioned criteria (i), (ii), (iii) and (iv). In some embodiments, the therapeutically active agent meets at least two of the abovementioned criteria (i), (ii), (iii) and (iv). In some embodiments, the therapeutically active agent meets at least three of the abovementioned criteria (i), (ii), (iii) and (iv). In some embodiments, the therapeutically active agent meets all four of the abovementioned criteria (i), (ii), (iii) and (iv).

In some embodiments of any one of the embodiments described herein, the therapeutically active agent has a molecular weight of at least 0.5 kDa, in accordance with any one of the embodiments described herein relating to a molecular weight of at least 0.5 kDa, and further meets at least one of the abovementioned criteria (i), (ii) and (iii). In some such embodiments, the therapeutically active agent meets at least two of the abovementioned criteria (i), (ii) and (iii).

Dihydroergotamine and fondaparinux are non-limiting examples of non-peptidic agents having a molecular weight of at least 0.5 kDa, which are poorly absorbed upon oral administration.

In some embodiments of any one of the embodiments described herein, the therapeutically active agent has a molecular weight of less than 0.5 kDa, and meets at least one of the abovementioned criteria (i), (ii) and (iii). In some such embodiments, the therapeutically active agent meets at least two of the abovementioned criteria (i), (ii) and (iii). In some such embodiments, the therapeutically active agent meets all three of the abovementioned criteria (i), (ii) and (iii).

In addition, ionic molecules tend to be poorly absorbed upon oral administration, generally due to a considerably reduced ability to cross lipid membranes. Whether a molecule is ionic or non-ionic often depends on pH, which varies according to location in the gastrointestinal tract. In general, it is believed that the more a therapeutically active agent is in ionic form in the gastrointestinal tract, the more likely it is to be poorly absorbed upon oral administration.

In some embodiments of any one of the embodiments described herein, the therapeutically active agent is ionic in an aqueous solution at a pH of 7.0.

In some embodiments of any one of the embodiments described herein, the therapeutically active agent is ionic in an aqueous solution at a pH of 6.0.

In some embodiments of any one of the embodiments described herein, the therapeutically active agent is ionic in an aqueous solution at a pH of 5.0.

In some embodiments of any one of the embodiments described herein, the therapeutically active agent is ionic in an aqueous solution at a pH of 4.0.

In some embodiments of any one of the embodiments described herein, the therapeutically active agent is ionic in an aqueous solution at a pH of 3.0.

In some embodiments of any one of the embodiments described herein, the therapeutically active agent is ionic in an aqueous solution at a pH of 2.0.

In some embodiments of any one of the embodiments described herein, the therapeutically active agent is ionic in an aqueous solution at a pH of 1.0.

Examples of such agents include, without limitation, compounds comprising at least one basic group (e.g., amine group) which is positively charged at a pH of 7.0 (or less).

Herein, a compound is considered "ionic" when it comprises at least one functional group which is charged in at least 50% of the molecules in a population of molecules of the compound under designated conditions (e.g., in an aqueous solution at a designated pH value or range of pH values). The skilled person will be readily capable of determining whether a functional group is charged in at least 50% of the molecules, for example, by determining a pKa value associated with the functional group. An ionic compound, as defined herein, may optionally have a net negative charge, optionally a net positive charge, and optionally an equal number of negatively charged functional groups and positively functional groups, resulting in no net charge.

In some embodiments of any one of the embodiments described herein, the therapeutically active agent is ionic in an aqueous solution at all pH values within a range of from 5.0 to 7.0. In some embodiments, the therapeutically active agent is ionic in an aqueous solution at all pH values within a range of from 5.0 to 8.0. In some embodiments, the therapeutically active agent is ionic in an aqueous solution at all pH values within a range of from 4.0 to 9.0. In some embodiments, the therapeutically active agent is ionic in an aqueous solution at all pH values within a range of from 3.0 to 10.0. In some embodiments, the therapeutically active agent is ionic in an aqueous solution at all pH values within a range of from 2.0 to 11.0.

In some embodiments of any one of the embodiments described herein, the therapeutically active agent is ionic at a pH value and/or range according to any one of the abovementioned embodiments, and further has a molecular weight of at least 0.5 kDa, in accordance with any one of the embodiments described herein relating to a molecular weight of at least 0.5 kDa.

In some embodiments of any one of the embodiments described herein, the therapeutically active agent is ionic at a pH value and/or range according to any one of the abovementioned embodiments, and further has a molecular weight of less than 0.5 kDa.

Examples of ionic therapeutically active agents which tend to have a molecular weight of less than 0.5 kDa, and which tend to exhibit poor absorption upon oral administration, include, without limitation, bisphosphonates (e.g., for use in treating osteoporosis and related conditions) such as alendronate, clodronate, etidronate, ibandronate, neridronate, olpadronate, pamidronate, risedronate, tiludronate and zoledronate; and cromolyn (e.g., cromolyn sodium).

In some embodiments of any one of the embodiments described herein, the therapeutically active agent is a Class III agent according to the Biopharmaceutics Classification System (BCS), as provided by the U.S. FDA, that is, the therapeutically active agent is characterized by low permeability and high solubility.

In the context of the BCS, the phrase "low permeability" refers herein and in the art to absorption of less than 90% of a given agent upon oral administration in humans (in the absence of SNAC), as determined by mass-balance determination and/or in comparison to an intravenous dose.

In some embodiments, absorption of a Class III therapeutically active agent is less than 50% upon oral administration (in the absence of SNAC). In some embodiments, absorption is less than 20% upon oral administration (in the absence of SNAC). In some embodiments, absorption is less than 10% upon oral administration (in the absence of SNAC). In some embodiments, absorption is less than 5% upon oral administration (in the absence of SNAC). In some embodiments, absorption is less than 2% upon oral administration (in the absence of SNAC). In some embodiments, absorption is less than 1% upon oral administration (in the absence of SNAC).

In the context of the BCS, the phrase "high solubility" refers herein and in the art to an amount of therapeutically active agent in an administered dose being soluble in 250 ml or less of water over a pH range of 1 to 7.5.

Formulation of Compositions:

Each of the compositions and unit dosage forms described herein, including cores and external layers described herein (individually or in combination), optionally consist essentially of the functional ingredients described hereinabove (e.g., a therapeutically active agent, SNAC, protease inhibitor(s) and/or antacid compound(s)), or alternatively, the composition further comprises suitable pharmaceutically acceptable carriers and/or excipients.

Hereinafter, the phrases "physiologically acceptable carrier" and "pharmaceutically acceptable carrier", which may be interchangeably used, refer to a carrier or a diluent that does not cause significant irritation to an organism and does not abrogate the activity (e.g., biological activity) and properties of the functional ingredient (e.g., a therapeutically active agent). An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

The term "unit dosage form", as used herein, describes physically discrete units, each unit containing a predetermined quantity of one or more active ingredient(s) calculated to produce the desired therapeutic effect, in association with at least one pharmaceutically acceptable carrier, diluent, excipient, or combination thereof.

In some embodiments of any one of the embodiments described herein, the composition is formulated as a solid composition. In some embodiments, the composition is formulated as a tablet.

Techniques for formulation and administration of drugs may be found in "Remington's Pharmaceutical Sciences," Mack Publishing Co., Easton, Pa., latest edition, which is incorporated herein by reference.

Pharmaceutical compositions and unit dosage forms of some embodiments of the invention, including cores and external layers described herein (individually or in combination), may be manufactured by processes well known in the art, e.g., by means of conventional mixing, dissolving, granulating, dragee-making, levigating, emulsifying, encapsulating, entrapping or lyophilizing processes.

Pharmaceutical compositions and unit dosage forms for use in accordance with some embodiments of the invention, including cores and external layers described herein (individually or in combination), may thus be formulated in conventional manner using one or more physiologically acceptable carriers comprising excipients and auxiliaries, which facilitate processing of the active ingredients into preparations which, can be used pharmaceutically.

The pharmaceutical composition and unit dosage forms can be formulated readily by combining the active compounds with pharmaceutically acceptable carriers well known in the art as being suitable for oral administration. Such carriers optionally facilitate formulation of the pharmaceutical composition as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores.

Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate; and/or lubricants such as talc or magnesium stearate.

In some embodiments of any one of the embodiments described herein, any one of the compositions or unit dosage forms described herein (e.g., formulated as a tablet) further comprises a lubricant. In some embodiments, the lubricant is included in a concentration of 5 weight percents or less, optionally 2 weight percents or less, and optionally about 1 weight percent. In some embodiments, the composition or unit dosage form described herein (e.g., formulated as a tablet) consists essentially of the therapeutically active agent (as described herein), SNAC, lubricant and least one protective agent (as described herein). In some embodiments, the lubricant is magnesium stearate.

Dragee cores are optionally provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added.

Pharmaceutical compositions suitable for use in context of some embodiments of the invention include compositions wherein the therapeutically active agent is contained in an amount effective to achieve the intended purpose. More specifically, the composition preferably comprises a therapeutically effective amount of therapeutically active agent, that is, an amount of therapeutically active agent effective to prevent, alleviate or ameliorate symptoms of a disorder or prolong the survival of the subject being treated. Furthermore, an amount of SNAC is preferably effective for enhancing absorption of the therapeutically active agent (e.g., in a manner described herein); and an amount of protease inhibitor is preferably effective for inhibiting degradation of the therapeutically active agent (e.g., a polypeptide agent) by a protease.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the therapeutically active agent described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide levels (e.g., plasma levels) of the therapeutically active agent sufficient to induce or suppress a biological effect (minimal effective concentration, MEC). The MEC will vary for each preparation, but can be estimated from in vitro data. Dosages necessary to achieve the MEC will depend on individual characteristics. Detection assays can be used to determine plasma concentrations.

Depending on the severity and responsiveness of the condition to be treated, dosing can be of a single or a plurality of administrations, with course of treatment lasting from several hours to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention may also be prepared (e.g., as described herein), placed in an appropriate container, and labeled for treatment of an indicated condition, as is further detailed herein.

Miscellaneous Definitions:

Herein, the term "polypeptide" refers to a polymer comprising at least 4 amino acid residues linked by peptide bonds or analogs thereof (as described herein), and optionally only by peptide bonds per se. In some embodiments, the polypeptide comprises at least 10 amino acid residues or analogs thereof. In some embodiments, the polypeptide comprises at least 20 amino acid residues or analogs thereof. In some embodiments, the polypeptide comprises at least 30 amino acid residues or analogs thereof. In some embodiments, the polypeptide comprises at least 50 amino acid residues or analogs thereof. The term "polypeptide" encompasses native polypeptides (e.g., degradation products, synthetically synthesized polypeptides and/or recombinant polypeptides), including, without limitation, native proteins, fragments of native proteins and homologs of native proteins and/or fragments thereof; as well as peptidomimetics (typically, synthetically synthesized polypeptides) and peptoids and semipeptoids which are polypeptide analogs, which may have, for example, modifications rendering the polypeptides more stable while in a body or more capable of penetrating into cells. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided herein.

Peptide bonds (—CO—NH—) within the polypeptide may be substituted, for example, by N-methylated amide bonds (—N(CH$_3$)—CO—), ester bonds (—C(=O)—O—), ketomethylene bonds (—CO—CH$_2$—), sulfinylmethylene bonds (—S(=O)—CH$_2$—), α-aza bonds (—NH—N(R)—CO—), wherein R is any alkyl (e.g., methyl), amine bonds (—CH$_2$—NH—), sulfide bonds (—CH$_2$—S—), ethylene bonds (—CH$_2$—CH$_2$—), hydroxyethylene bonds (—CH(OH)—CH$_2$—), thioamide bonds (—CS—NH—), olefinic double bonds (—CH=CH—), fluorinated olefinic double bonds (—CF=CH—), retro amide bonds (—NH—CO—), peptide derivatives (—N(R)—CH$_2$—CO—), wherein R is the "normal" side chain, naturally present on the carbon atom.

These modifications can occur at any of the bonds along the polypeptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The polypeptides of some embodiments of the invention (e.g., a therapeutically active agent and/or a protease inhibitor described herein) may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1), and non-conventional or modified amino acids (e.g., synthetic, Table 2) which can be used with some embodiments of the invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| ornithine | Orn | hydroxyproline | Hyp |
| α-aminobutyric acid | Abu | aminonorbornyl-carboxylate | Norb |
| D-alanine | Dala | | |
| D-arginine | Darg | aminocyclopropane-carboxylate | Cpro |
| D-asparagine | Dasn | | |
| D-aspartic acid | Dasp | N-(3-guanidinopropyl)glycine | Narg |
| D-cysteine | Dcys | | |

TABLE 2-continued

| Non-conventional amino acid | Code | Non-conventional amino acid | Code |
|---|---|---|---|
| D-glutamine | Dgln | N-(carbamylmethyl)glycine | Nasn |
| D-glutamic acid | Dglu | N-(carboxymethyl)glycine | Nasp |
| D-histidine | Dhis | N-(thiomethyl)glycine | Ncys |
| D-isoleucine | Dile | N-(2-carbamylethyl)glycine | Ngln |
| D-leucine | Dleu | N-(2-carboxyethyl)glycine | Nglu |
| D-lysine | Dlys | N-(imidazolylethyl)glycine | Nhis |
| D-methionine | Dmet | N-(1-methylpropyl)glycine | Nile |
| D-ornithine | Dorn | N-(2-methylpropyl)glycine | Nleu |
| D-phenylalanine | Dphe | N-(4-aminobutyl)glycine | Nlys |
| D-proline | Dpro | N-(2-methylthioethyl)glycine | Nmet |
| D-serine | Dser | N-(3-aminopropyl)glycine | Norn |
| D-threonine | Dthr | N-benzylglycine | Nphe |
| D-tryptophan | Dtrp | N-(hydroxymethyl)glycine | Nser |
| D-tyrosine | Dtyr | N-(1-hydroxyethyl)glycine | Nthr |
| D-valine | Dval | N-(3-indolylethyl)glycine | Nhtrp |
| D-N-methylalanine | Dnmala | N-(p-hydroxyphenyl)glycine | Ntyr |
| D-N-methylarginine | Dnmarg | N-(1-methylethyl)glycine | Nval |
| D-N-methylasparagine | Dnmasn | N-methylglycine | Nmgly |
| D-N-methylasparatate | Dnmasp | L-N-methylalanine | Nmala |
| D-N-methylcysteine | Dnmcys | L-N-methylarginine | Nmarg |
| D-N-methylglutamine | Dnmgln | L-N-methylasparagine | Nmasn |
| D-N-methylglutamate | Dnmglu | L-N-methylaspartic acid | Nmasp |
| D-N-methylhistidine | Dnmhis | L-N-methylcysteine | Nmcys |
| D-N-methylisoleucine | Dnmile | L-N-methylglutamine | Nmgln |
| D-N-methylleucine | Dnmleu | L-N-methylglutamic acid | Nmglu |
| D-N-methyllysine | Dnmlys | L-N-methylhistidine | Nmhis |
| D-N-methylmethionine | Dnmmet | L-N-methylisolleucine | Nmile |
| D-N-methylornithine | Dnmorn | L-N-methylleucine | Nmleu |
| D-N-methylphenyl-alanine | Dnmphe | L-N-methyllysine | Nmlys |
| | | L-N-methylmethionine | Nmmet |
| D-N-methylproline | Dnmpro | L-N-methylornithine | Nmorn |
| D-N-methylserine | Dnmser | L-N-methylphenylalanine | Nmphe |
| D-N-methylthreonine | Dnmthr | L-N-methylproline | Nmpro |
| D-N-methyltryptophan | Dnmtrp | L-N-methylserine | Nmser |
| D-N-methyltyrosine | Dnmtyr | L-N-methylthreonine | Nmthr |
| D-N-methylvaline | Dnmval | L-N-methyltryptophan | Nmtrp |
| L-norleucine | Nle | L-N-methyltyrosine | Nmtyr |
| L-norvaline | Nva | L-N-methylvaline | Nmval |
| L-ethylglycine | Etg | L-N-methylnorleucine | Nmnle |
| L-t-butylglycine | Tbug | L-N-methylnoryaline | Nmnva |
| L-homophenylalanine | Hphe | L-N-methyl-ethylglycine | Nmetg |
| α-naphthylalanine | Anap | L-N-methyl-t-butylglycine | Nmtbug |
| penicillamine | Pen | L-N-methyl-homophenylalanine | Nmhphe |
| γ-aminobutyric acid | Gabu | | |
| cyclohexylalanine | Chexa | N-methyl-α-naphthylalanine | Nmanap |
| cyclopentylalanine | Cpen | N-methylpenicillamine | Nmpen |
| α-amino-α-methylbutyrate | Aabu | N-methyl-γ-aminobutyrate | Nmgabu |
| | | N-methyl-cyclohexylalanine | Nmchexa |
| α-aminoisobutyric acid | Aib | | |
| | | N-methyl-cyclopentylalanine | Nmcpen |
| D-α-methylarginine | Dmarg | N-methyl-α-amino-α-methylbutyrate | Nmaabu |
| D-α-methylasparagine | Dmasn | | |
| D-α-methylaspartate | Dmasp | N-methyl-α-aminoisobutyrate | Nmaib |
| D-α-methylcysteine | Dmcys | | |
| D-α-methylglutamine | Dmgln | L-α-methylarginine | Marg |
| D-α-methylglutamic acid | Dmglu | L-α-methylasparagine | Masn |
| | | L-α-methylaspartate | Masp |
| D-α-methylhistidine | Dmhis | L-α-methylcysteine | Mcys |
| D-α-methylisoleucine | Dmile | L-α-methylglutamine | Mgln |
| D-α-methylleucine | Dmleu | L-α-methylglutamate | Mglu |
| D-α-methyllysine | Dmlys | L-α-methylhistidine | Mhis |
| D-α-methylmethionine | Dmmet | L-α-methylisoleucine | Mile |
| D-α-methylornithine | Dmorn | L-α-methylleucine | Mleu |
| D-α-methylphenyl-alanine | Dmphe | L-α-methyllysine | Mlys |
| | | L-α-methylmethionine | Mmet |
| D-α-methylproline | Dmpro | L-α-methylornithine | Morn |
| D-α-methylserine | Dmser | L-α-methylphenylalanine | Mphe |
| D-α-methylthreonine | Dmthr | L-α-methylproline | Mpro |
| D-α-methyltryptophan | Dmtrp | L-α-methylserine | Mser |
| D-α-methyltyrosine | Dmtyr | L-α-methylthreonine | Mthr |
| D-α-methylvaline | Dmval | L-α-methyltryptophan | Mtrp |
| N-cyclobutylglycine | Ncbut | L-α-methyltyrosine | Mtyr |
| N-cycloheptylglycine | Nchep | L-α-methylvaline | Mval |
| N-cyclohexylglycine | Nchex | L-α-methylnorvaline | Mnva |
| N-cyclodecylglycine | Ncdec | L-α-methylethylglycine | Metg |
| N-cyclododecyl-glycine | Ncdod | L-α-methyl-t-butylglycine | Mtbug |
| | | L-α-methyl- | Mhphe |
| N-cyclooctylglycine | Ncoct | homophenylalanine | |
| N-cyclopropylglycine | Ncpro | α-methyl-α-naphthylalanine | Manap |
| N-cycloundecyl-glycine | Ncund | α-methylpenicillamine | Mpen |
| | | α-methyl-γ-aminobutyrate | Mgabu |
| N-(2-aminoethyl) glycine | Naeg | α-methyl-cyclohexylalanine | Mchexa |
| | | α-methyl-cyclopentylalanine | Mcpen |
| N-(2,2-diphenylethyl)glycine | Nbhm | N-(N-(2,2-diphenylethyl) carbamylmethyl-glycine | Nnbhm |
| N-(3,3-diphenyl-propyl)glycine | Nbhe | N-(N-(3,3-diphenylpropyl) carbamylmethyl-glycine | Nnbhe |
| 1-carboxy-1-(2,2-diphenylethylamino) cyclopropane | Nmbc | 1,2,3,4-tetrahydroisoquinoline-3-carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

The polypeptides of some embodiments of the invention (e.g., a therapeutically active agent and/or a protease inhibitor described herein) are preferably utilized in a linear form, although it will be appreciated that in cases where cyclicization does not severely interfere with polypeptide characteristics, cyclic forms of the polypeptide can also be utilized.

In some embodiments of any one of the embodiments described herein, the polypeptide is water-soluble.

Herein, the term "water-soluble" refers to a compound having a solubility of at least 1 gram per liter in an aqueous solution at pH 7.

Water-soluble polypeptides preferably include one or more non-natural or natural polar amino acids, including but not limited to serine and threonine which are capable of increasing polypeptide water-solubility due to their hydroxyl-containing side chain. Optionally, a homolog of a polypeptide is selected so as to be more water-soluble than the parent polypeptide, for example, by replacing one or more amino acids in the polypeptide with polar amino acids.

The polypeptides of some embodiments of the invention (e.g., a therapeutically active agent and/or a protease inhibitor described herein) may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing polypeptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the polypeptide compounds of some embodiments of the invention (e.g., a therapeutically active agent and/or a protease inhibitor described herein) involves solid phase peptide synthesis.

Large scale polypeptide synthesis is described by Andersson et al. [*Biopolymers* 2000; 55:227-250].

Herein, a "homolog" of a given polypeptide refers to a polypeptide that exhibits at least 80% homology, preferably at least 90% homology, and more preferably at least 95% homology, and more preferably at least 98% homology to the given polypeptide. In some embodiments, a homolog of a given polypeptide further shares a therapeutic activity with the given polypeptide. The percentage of homology refers to the percentage of amino acid residues in a first polypeptide sequence which match a corresponding residue of a second polypeptide sequence to which the first polypeptide is being compared. Generally, the polypeptides are aligned to give maximum homology. A variety of strategies are known in the art for performing comparisons of amino acid or nucleotide sequences in order to assess degrees of identity, including, for example, manual alignment, computer assisted sequence alignment and combinations thereof. A number of algorithms (which are generally computer implemented) for performing sequence alignment are widely available, or can be produced by one of skill in the art. Representative algorithms include, e.g., the local homology algorithm of Smith and Waterman (Adv. Appl. Math., 1981, 2: 482); the homology alignment algorithm of Needleman and Wunsch (J. Mol. Biol., 1970, 48: 443); the search for similarity method of Pearson and Lipman (Proc. Natl. Acad. Sci. (USA), 1988, 85: 2444); and/or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.). Readily available computer programs incorporating such algorithms include, for example, BLASTN, BLASTP, Gapped BLAST, PILEUP, CLUSTALW etc. When utilizing BLAST and Gapped BLAST programs, default parameters of the respective programs may be used. Alternatively, the practitioner may use non-default parameters depending on his or her experimental and/or other requirements (see for example, the Web site having URL www(dot)ncbi(dot)nlm(dot)nih(dot)gov).

It is expected that during the life of a patent maturing from this application many relevant therapeutically active agents and many relevant treatments of conditions by therapeutically active agents will be developed, and the scope of the phrases "therapeutically active agent" and "condition treatable by . . . therapeutically active agent" are intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a therapeutically active agent" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

In some embodiments of any one of the embodiments described herein, the unit dosage form and/or composition according to any of the aspects described herein is for use in the treatment of a condition treatable by oral administration of the therapeutically active agent (e.g., a condition described herein).

According to another aspect of embodiments of the invention, there is provided a use of a unit dosage form and/or composition according to any of the aspects described herein in the preparation of a medicament for use in the treatment of a condition treatable by oral administration of the therapeutically active agent (e.g., a condition described herein).

According to another aspect of embodiments of the invention, there is provided a method of treating a condition treatable by oral administration of a therapeutically active agent in a subject in need thereof (e.g., a condition and therapeutically active agent described herein), the method comprising orally administering to the subject a unit dosage form and/or composition according to any of the aspects described herein which comprises the therapeutically active agent.

Examples of conditions treatable according to embodiments of the invention include, without limitation, hyperglycemia, for example, in diabetes (e.g., wherein the therapeutically active agent is an insulin or a GLP-1, or another agent which reduces blood glucose levels); hypoglycemia (e.g., wherein the therapeutically active agent is a glucagon, or another agent which increases blood glucose levels); osteoporosis (e.g., wherein the therapeutically active agent is a PTH or fragment thereof); and hypoparathyroidism (e.g., wherein the therapeutically active agent is a PTH or fragment thereof).

The skilled person will be capable of determining which conditions are treatable by oral administration of any given therapeutically active agent.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials:

8-Aminocaprylic acid was obtained from Alfa-Aesar.

O-acetylsalicyloyl chloride was obtained from Sigma-Aldrich.

Soybean trypsin inhibitor was obtained from Sigma-Aldrich.

Teriparatide was obtained from Bachem.

Sodium bicarbonate was obtained from Merck.

SNAC (sodium 8-N-(2-hydroxybenzoyl)aminocaprylate) was prepared by reacting O-acetylsalicyloyl chloride with 8-aminocaprylic acid.

Example 1

Effect of Antacid on Release of SNAC

Two tablet formulations were prepared, having the same amounts of SNAC, trypsin inhibitor and teriparatide (parathyroid hormone (1-34)), wherein one formulation further contained 100 mg sodium bicarbonate and the other formulation did not contain sodium bicarbonate. The tablets were in a form of a homogeneous mixture.

Each tablet formulation was subjected to a dissolution test in 100 ml of simulated gastric buffer (without pepsin), pH 2.0, at 37° C., according to USP 23 Apparatus 2 (paddle) with 50 rotations per minute. The amount of released SNAC in each sample was determined chromatographically, using an HPLC apparatus with Cosmosil™ 5 C18-MS-II (4.6 ID×250 mm) column. Mobile phase consisted of 50% acetonitrile and 50% phosphoric acid solution (0.1%). Flow rate was 1 ml/minute and injection volume was 25 μl. Amount of released SNAC was calculated as a percentage of the amount of SNAC in the formulation.

As shown in FIG. 8, sodium bicarbonate considerably enhanced the dissolution of SNAC in tablets, and preserved the soluble fraction of SNAC.

These results indicate that formulation with an antacid such as sodium bicarbonate can considerably enhance the effect of the absorption enhancer SNAC.

Example 2

Effect of Antacid on Pharmacokinetic Profile of Orally Administered Parathyroid Hormone (PTH)

An open label comparative pharmacokinetic study was performed on ten healthy volunteers. On different visits, each volunteer received the same oral tablet containing 0.75 mg of teriparatide, a recombinant form of parathyroid hormone (1-34) (PTH(1-34)). In the first visit, the tablet was administered with 150 ml water, whereas in the second visit the tablet was administered with 150 ml of 3 mg/ml sodium bicarbonate aqueous solution.

The formulation was composed of teriparatide (0.75 mg), SNAC (sodium 8-N-(2-hydroxybenzoyl)aminocaprylate), soybean trypsin inhibitor (SBTI) and a small amount of magnesium stearate.

Tablets were administered in the morning after an 8-hour overnight fast. At each visit a standard meal was provided 3 hours after drug administration. Patients did not eat nor drink alcoholic or caffeinated beverages. There was a two week period between the two visits.

To determine PTH(1-34) concentrations, blood samples (4 ml each) were drawn via an indwelling catheter from the forearm vein at predetermined time points during each visit. The cannula was flushed with 1.5 ml normal saline after each sampling. In addition, to avoid sample dilution, 1 ml of blood was drawn and discarded before the next sample. The blood samples were taken at the following times points: baseline (predose), 10 minutes, 15 minutes, 20 minutes, 30 minutes, 45 minutes, 60 minutes, 75 minutes, 90 minutes, 105 minutes, 2 hours, 3 hours, 4 hours and 5 hours post-administration. Each blood sample was collected into a single tube containing EDTA (ethylenediaminetetraacetic acid) and placed on ice. Within 15 minutes of blood collection, samples were centrifuged for 10 minutes at 4° C. (2500 rotations per minute) and the plasma was separated and divided into two or three aliquots. Each aliquot was transferred into appropriately labeled polypropylene tubes and stored at approximately −20° C. pending analysis. PTH(1-34) levels were measured using an IDS-iSYS automated assay for the measurement of intact PTH(1-34) in human plasma or serum. The results of the assay do not include levels of PTH(1-84) such as endogenous PTH. Relative absorption was determined based on the AUC (area under curve) parameter.

As shown in FIG. 9, co-administration with sodium bicarbonate solution increased absorption of PTH(1-34)

from an orally administered formulation by about 35%, in comparison with co-administration of the formulation with water.

These results indicate that co-administration with an antacid enhances the ability of SNAC to promote absorption of therapeutically active agents.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A pharmaceutical composition for oral administration of a therapeutic active agent, the composition comprising a therapeutically active agent, SNAC (sodium 8-N-(2-hydroxybenzoyl)aminocaprylate), and at least one antacid compound selected from the group consisting of calcium citrate, calcium gluconate, sodium gluconate, sodium citrate, sodium hydroxide, potassium gluconate, potassium citrate, potassium hydroxide, magnesium gluconate, magnesium citrate, magnesium hydroxide, magnesium oxide, aluminum gluconate, aluminum citrate, and aluminum hydroxide, wherein said therapeutically active agent has a molecular weight in a range of 0.5 kDa to 150 kDa, and wherein said at least one antacid compound is in a total amount of at least 1 mg.

2. The composition of claim 1, further comprising at least one protease inhibitor.

3. The composition of claim 1, wherein at least 90 weight percents of the composition consists of ingredients selected from the group consisting of said therapeutically active agent, SNAC, and said at least one antacid compound.

4. The composition of claim 1, wherein said therapeutically active agent is a polypeptide.

5. The composition of claim 4, wherein said polypeptide is selected from the group consisting of a parathyroid hormone, insulin, a glucagon, an interferon, a growth hormone, an erythropoietin, a calcitonin, an omentin, a motilin, a leptin, a peptide YY, a GLP-1, a GLP-2, a granulocyte colony stimulating factor (G-CSF), an antibody, an interleukin, an erythropoietin, a vasopressin, a vasoactive intestinal peptide, a pituitary adenylate cyclase-activating peptide (PACAP), a blood clotting factor, an endomorphin, a TNF inhibitor, disitertide, octreotide, davunetide, icatibant, glucocerebrosidase, a gonadotropin releasing hormone, acyline, and a GLP-1 agonist.

6. The composition of claim 1, being formulated as a unit dosage form.

7. The composition of claim 6, wherein said unit dosage form comprises at least 20 mg of SNAC.

8. A method of treating a condition treatable by oral administration of a therapeutically active agent in a subject in need thereof, the method comprising orally administering to the subject the composition of claim 1, to a subject in need thereof.

9. A method of treating a condition treatable by oral administration of a therapeutically active agent in a subject in need thereof, the method comprising co-administering to the subject, by oral administration, an antacid composition comprising at least one antacid compound in a total amount of at least 0.003 molar equivalent of base and/or at least one gastric acid secretion inhibitor, and a composition comprising said therapeutically active agent and SNAC (sodium 8-N-(2-hydroxybenzoyl)aminocaprylate), wherein said therapeutically active agent has a molecular weight in a range of 0.5 kDa to 150 kDa.

10. The method of claim 9, wherein said co-administering comprises administering said antacid composition prior to or concomitantly with said composition comprising said therapeutically active agent and SNAC.

11. The method of claim 9, wherein said therapeutically active agent is a polypeptide.

12. A pharmaceutical composition unit dosage form for oral administration of a therapeutically active agent which has a molecular weight in a range of 0.5 kDa to 150 kDa, the unit dosage form comprising:
   a core comprising the therapeutically active agent and SNAC (sodium 8-N-(2-hydroxybenzoyl)aminocaprylate); and
   an external layer comprising at least one protective agent selected from the group consisting of an antacid compound in an amount of at least 1 mg and a protease inhibitor, wherein said antacid compound is selected from the group consisting of calcium citrate, calcium gluconate, sodium gluconate, sodium citrate, sodium hydroxide, potassium gluconate, potassium citrate, potassium hydroxide, magnesium gluconate, magnesium citrate, magnesium hydroxide, magnesium oxide, aluminum gluconate, aluminum citrate, and aluminum hydroxide.

13. The unit dosage form of claim 12, wherein said external layer is devoid of SNAC.

14. The unit dosage form of claim 12, wherein said external layer comprises at least one protease inhibitor.

15. The unit dosage form of claim 12, being coated with an enteric coating.

16. The unit dosage form of claim 12, wherein said external layer and/or core comprises at least one of said antacid compound.

17. The unit dosage form of claim 12, being soluble in gastric fluid.

18. The unit dosage form of claim 12, being in a form of a tablet comprising said core and said external layer.

19. The unit dosage form of claim 12, comprising at least 20 mg of SNAC.

20. The unit dosage form of claim 12, wherein said therapeutically active agent is a polypeptide.

21. The unit dosage form of claim 20, wherein said polypeptide is selected from the group consisting of a parathyroid hormone, insulin, a glucagon, an interferon, a growth hormone, an erythropoietin, a calcitonin, an omentin, a motilin, a leptin, a peptide YY, a GLP-1, a GLP-2, a granulocyte colony stimulating factor (G-CSF), an antibody, an interleukin, an erythropoietin, a vasopressin, a vasoactive intestinal peptide, a pituitary adenylate cyclase-activating peptide (PACAP), a blood clotting factor, an endomorphin, a TNF inhibitor, disitertide, octreotide, davunetide, icatibant, glucocerebrosidase, a gonadotropin releasing hormone, acyline, and a GLP-1 agonist.

22. The unit dosage form of claim 12, wherein said core and/or said external layer further comprises a pharmaceutically acceptable carrier.

23. A method of treating a condition treatable by oral administration of a therapeutically active agent in a subject in need thereof, the method comprising orally administering to the subject the unit dosage form of claim 12, to a subject in need thereof.

\* \* \* \* \*